US010796782B2

(12) United States Patent
Shelton

(10) Patent No.: US 10,796,782 B2
(45) Date of Patent: Oct. 6, 2020

(54) SYSTEM, METHOD AND APPARATUS TO ENHANCE PRIVACY AND ENABLE BROAD SHARING OF BIOINFORMATIC DATA

(71) Applicants: PRIVATE ACCESS, INC., Irvine, CA (US); Robert Shelton, Irvine, CA (US)

(72) Inventor: Robert Shelton, Irvine, CA (US)

( * ) Notice: Subject to any disclaimer, the term of this patent is extended or adjusted under 35 U.S.C. 154(b) by 0 days.

(21) Appl. No.: 15/560,562

(22) PCT Filed: Mar. 23, 2016

(86) PCT No.: PCT/US2016/023687
§ 371 (c)(1),
(2) Date: Sep. 22, 2017

(87) PCT Pub. No.: WO2016/154254
PCT Pub. Date: Sep. 29, 2016

(65) Prior Publication Data
US 2018/0046753 A1  Feb. 15, 2018

Related U.S. Application Data

(60) Provisional application No. 62/136,700, filed on Mar. 23, 2015.

(51) Int. Cl.
*G16B 20/00* (2019.01)
*G16B 30/00* (2019.01)
(Continued)

(52) U.S. Cl.
CPC ......... *G16B 20/00* (2019.02); *G06F 21/6245* (2013.01); *G16B 30/00* (2019.02);
(Continued)

(58) Field of Classification Search
CPC ........ G16B 20/00; G16B 50/00; G16B 30/00; G16H 80/00; G16H 50/70; G16H 10/60; G06F 21/6245
See application file for complete search history.

(56) References Cited

U.S. PATENT DOCUMENTS 10,013,575 B2 * 7/2018 Hubaux .............. G06F 21/6245
2004/0122704 A1    6/2004 Sabol et al.
(Continued)

FOREIGN PATENT DOCUMENTS

WO    2013049420 A1    4/2013
WO    2014202615 A2    12/2014
WO    2016003660 A1    1/2016

OTHER PUBLICATIONS

Tharapel (Human Chromosome Nomenclature, The Principles of Clinical Cytogenetics, Second Edition, 2005, pp. 27-57) (Year: 2005).*
(Continued)

*Primary Examiner* — Oleg Korsak
(74) *Attorney, Agent, or Firm* — Burns & Levinson LLP; John C. Serio

(57) ABSTRACT

A system and apparatus for enabling individuals to control the sharing and disclosure of their bioinformatic data, including whole genome sequence data over a network. In combination with a privacy preference repository and policy repository for expressing legal and institutional criteria for accessing such bioinformatic information, a private access bureau enables such privacy and policy requirements to be applied while simultaneously enabling sharing of such bioinformatics data by properly authorized parties or applications. Through the use of various forms of metadata, encryption, and unique IDs that accompany such data elements, discrete segments of said bioinformatic data can be queried; and where permissible discovered, analyzed and linked with other health data based on pertinent privacy laws, institutional policies, and the individual's preferences that are associated with, and dynamically controlled through, an intuitive user interface.

11 Claims, 24 Drawing Sheets

(51) Int. Cl.
*G16B 50/00* (2019.01)
*G06F 21/62* (2013.01)
*G16H 80/00* (2018.01)
*G16H 50/70* (2018.01)
*G16H 10/60* (2018.01)

(52) U.S. Cl.
CPC ............ *G16B 50/00* (2019.02); *G16H 10/60* (2018.01); *G16H 50/70* (2018.01); *G16H 80/00* (2018.01)

(56) References Cited

U.S. PATENT DOCUMENTS

| | | |
|---|---|---|
| 2011/0247081 A1* | 10/2011 | Shelton ............... G06F 21/6218 726/28 |
| 2012/0233201 A1 | 9/2012 | Ganeshalingam et al. |
| 2012/0331567 A1 | 12/2012 | Shelton |
| 2013/0096943 A1 | 4/2013 | Carey et al. |
| 2014/0289001 A1 | 9/2014 | Shelton |

OTHER PUBLICATIONS

Lehne et al (From SNPs to Genes: Disease Association at the Gene Level, PLoS One 6(6):, Jun. 30, 2011, 10 pages) (Year: 2011).*

* cited by examiner

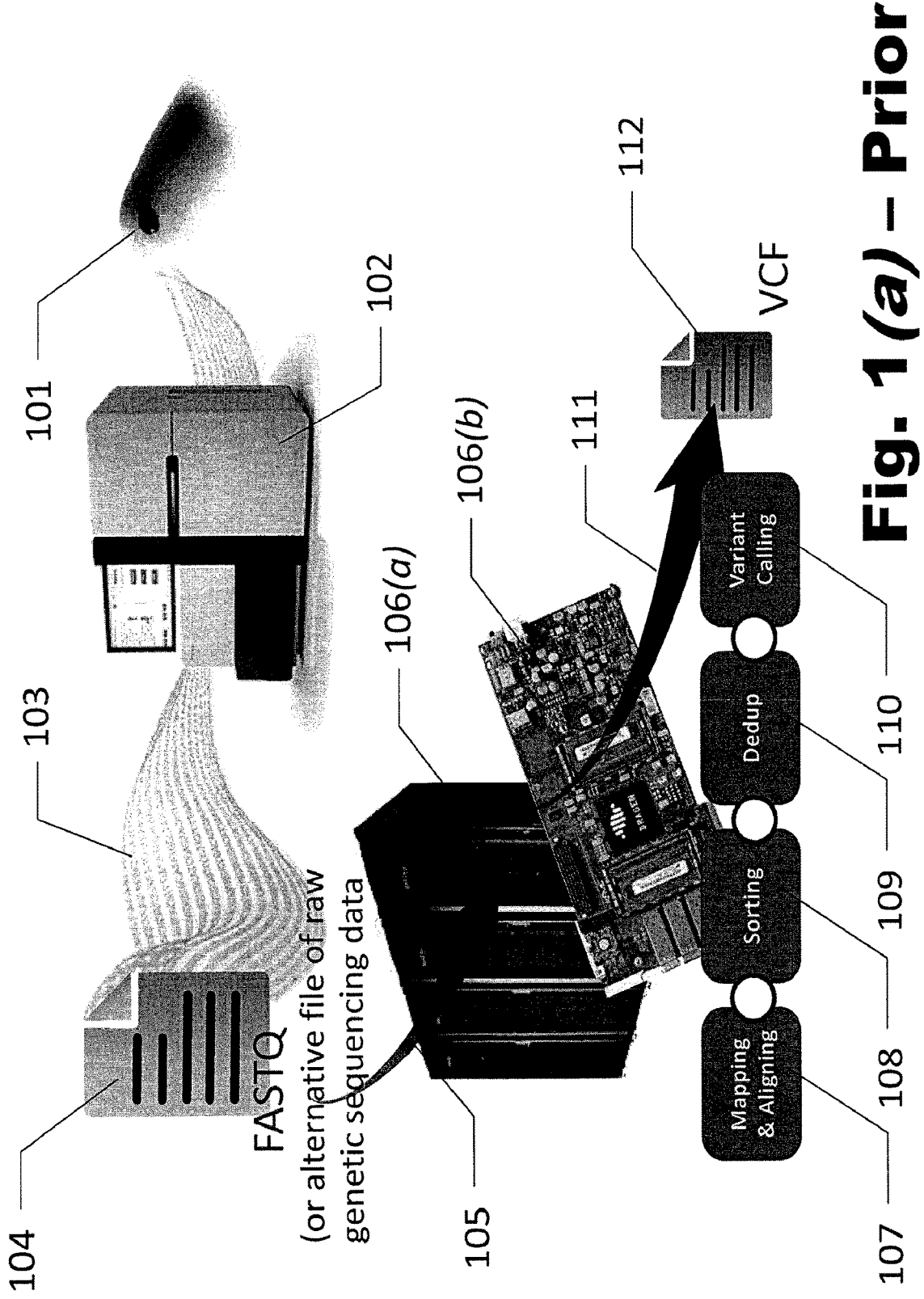
Fig. 1(a) – Prior Art

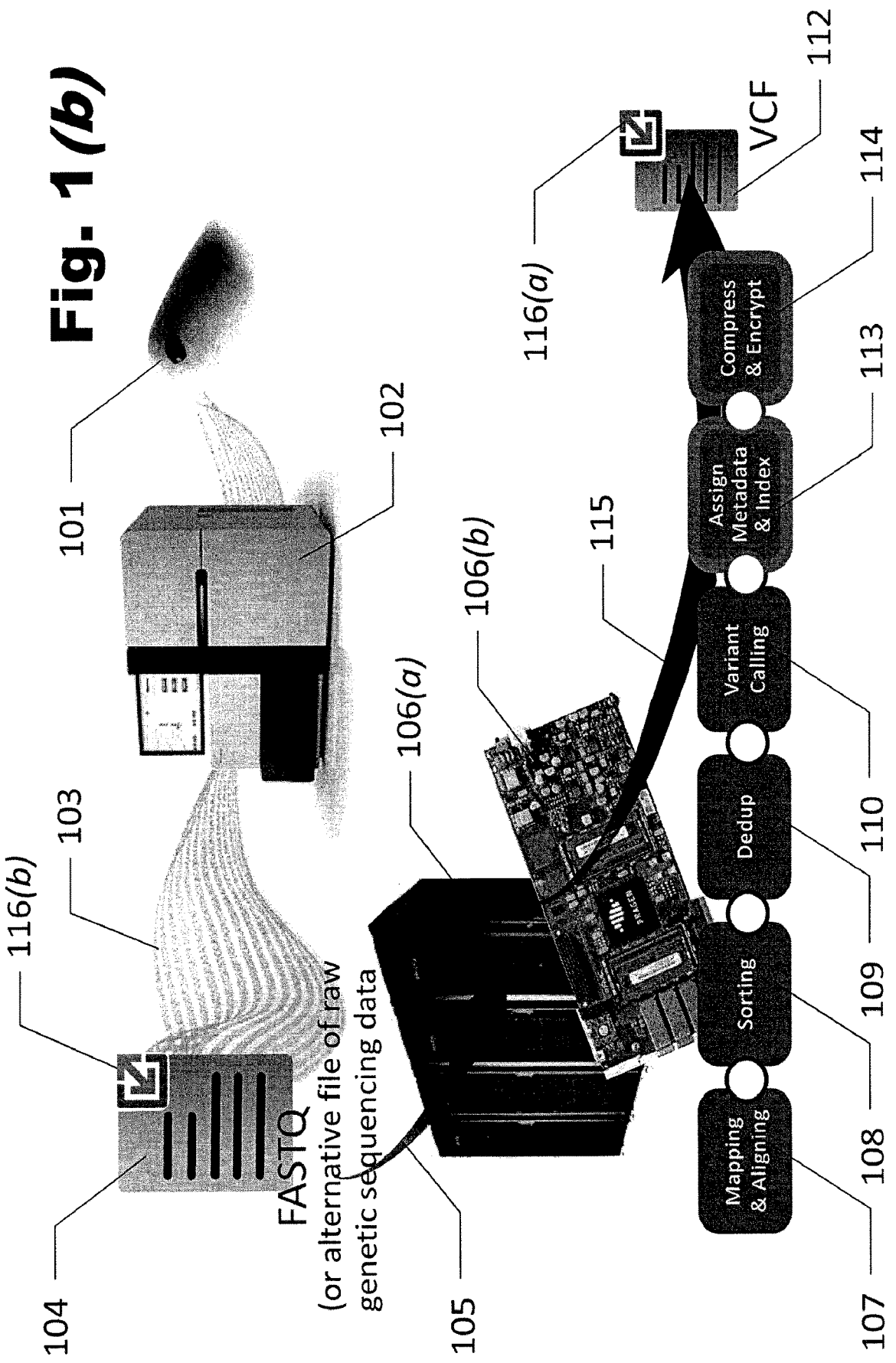

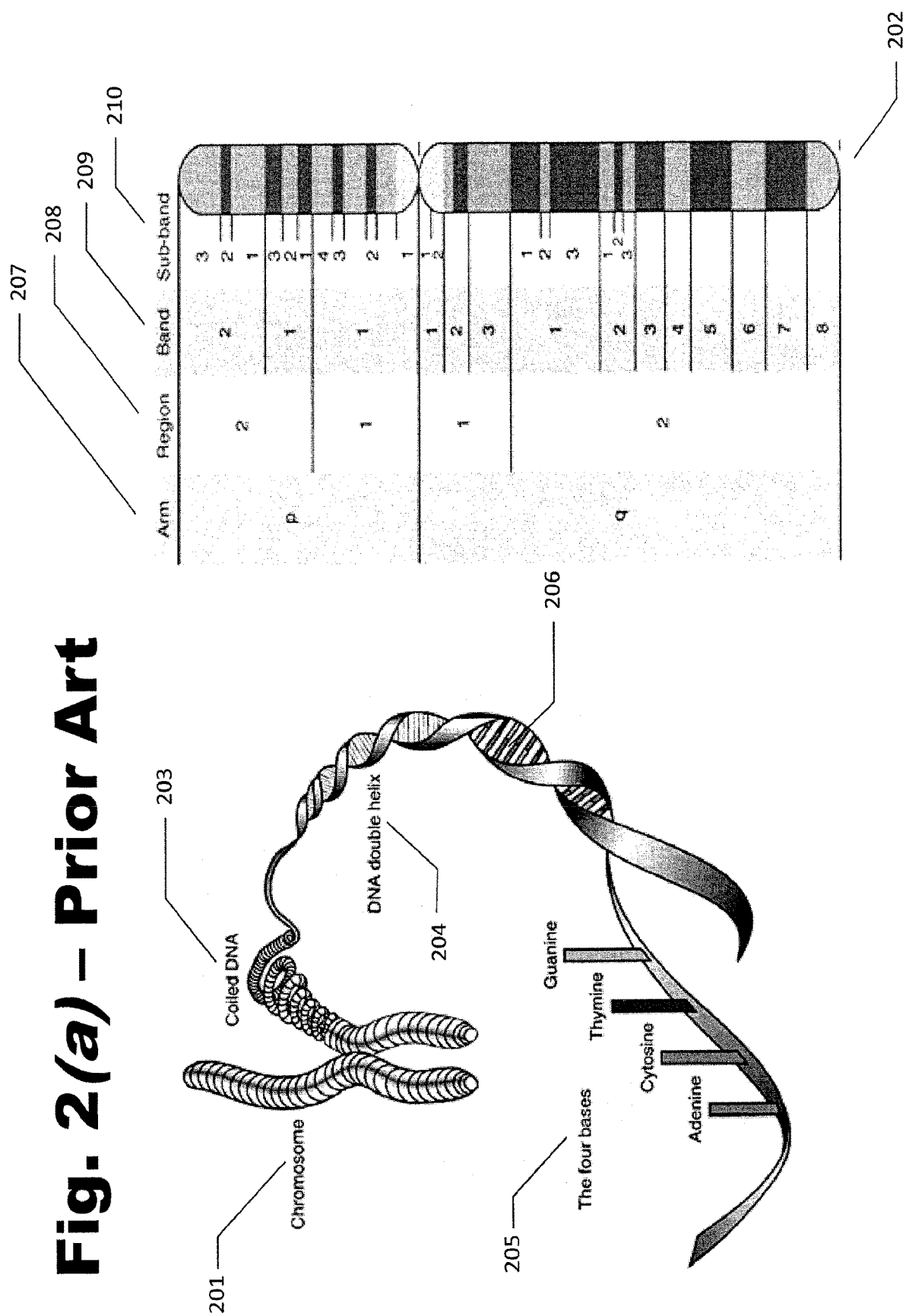
Fig. 2(a) – Prior Art

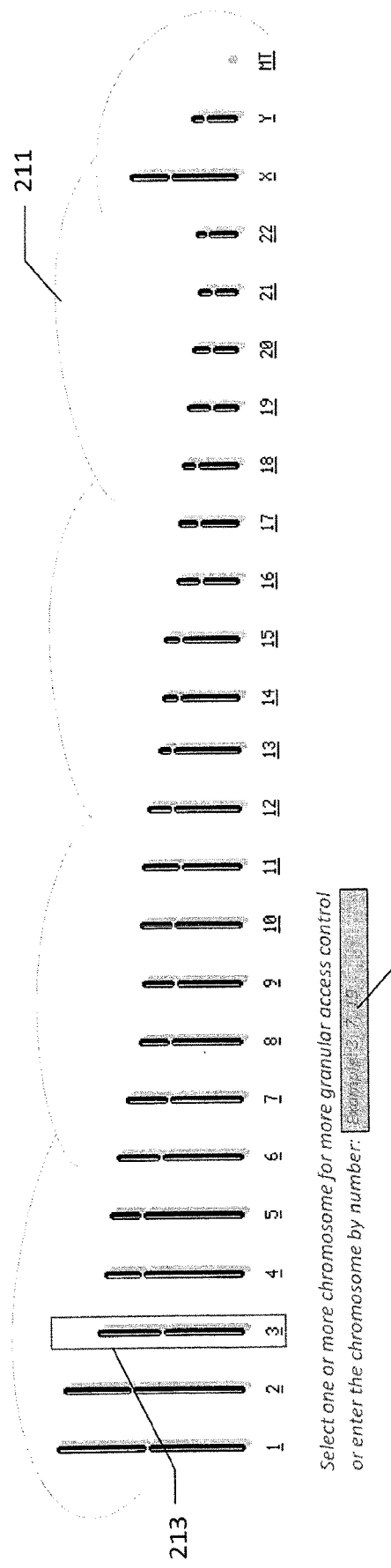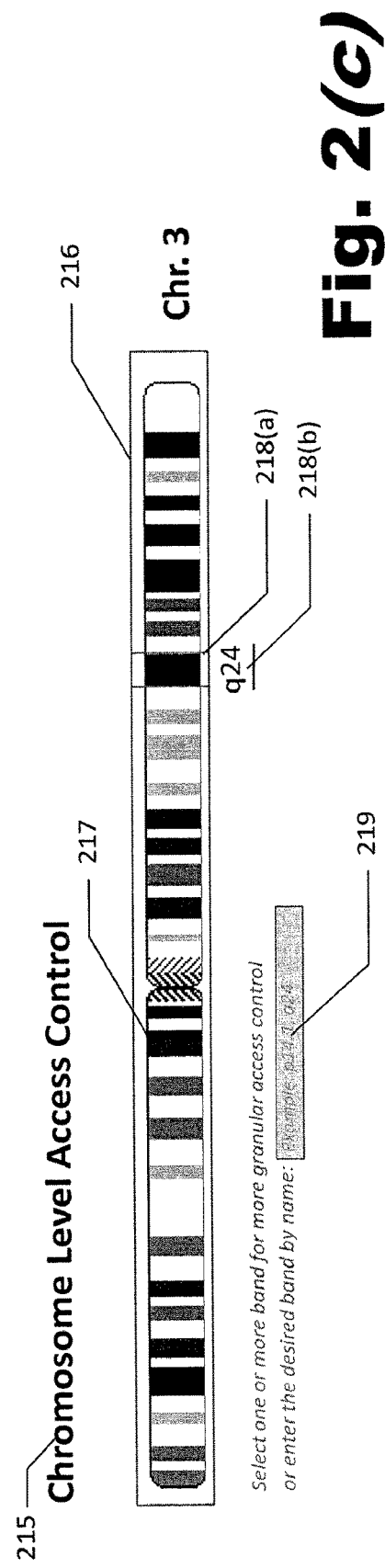

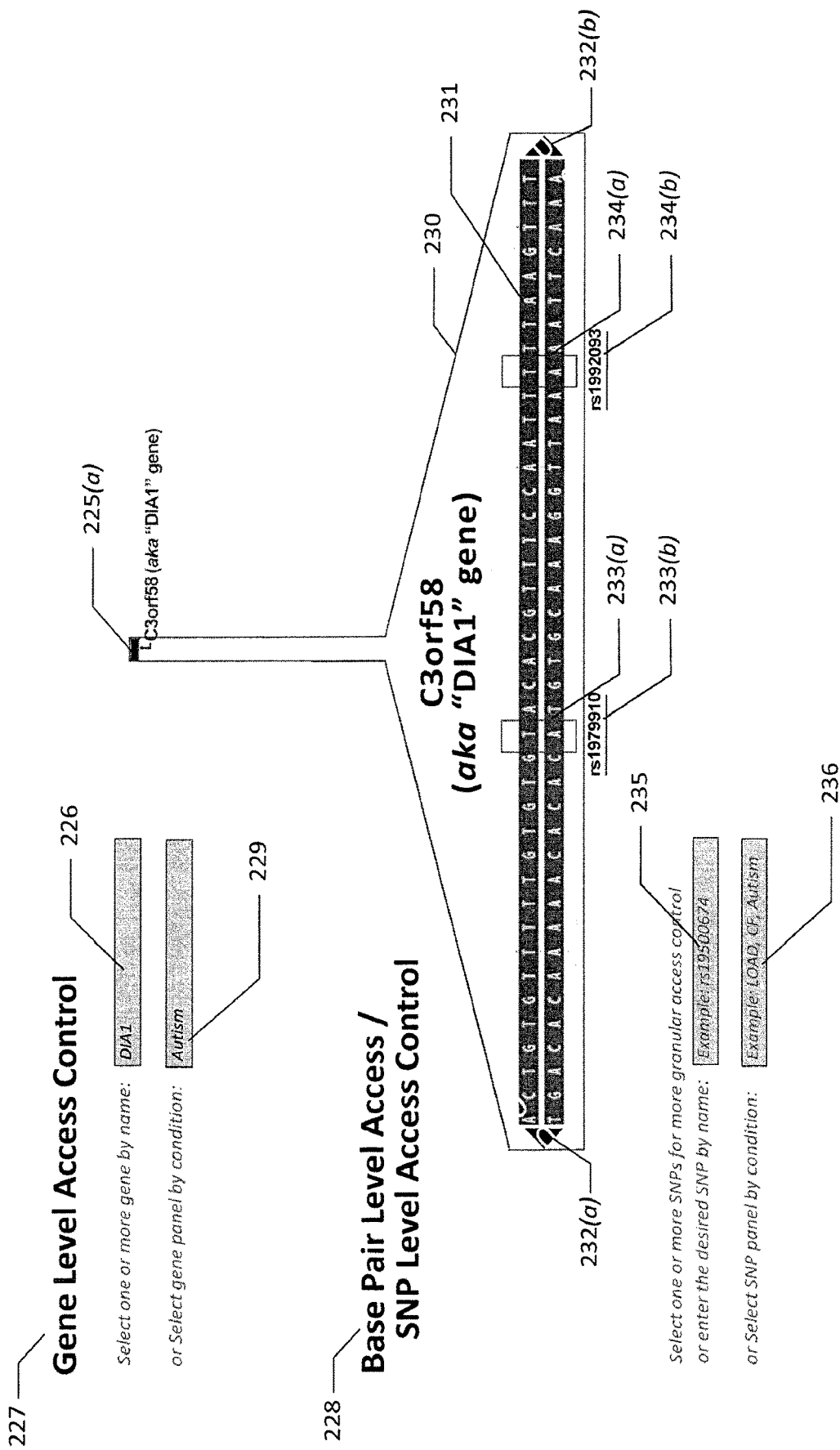

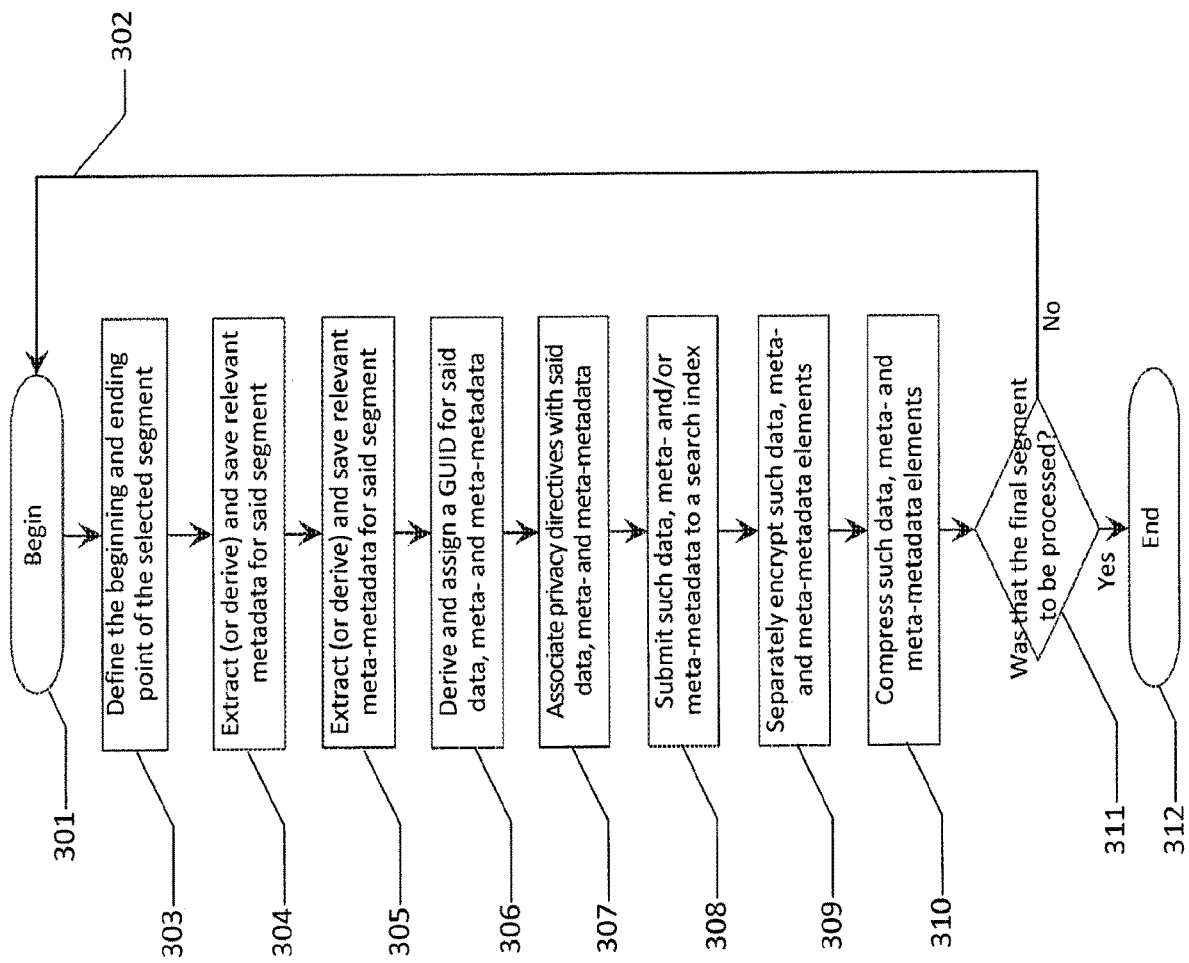

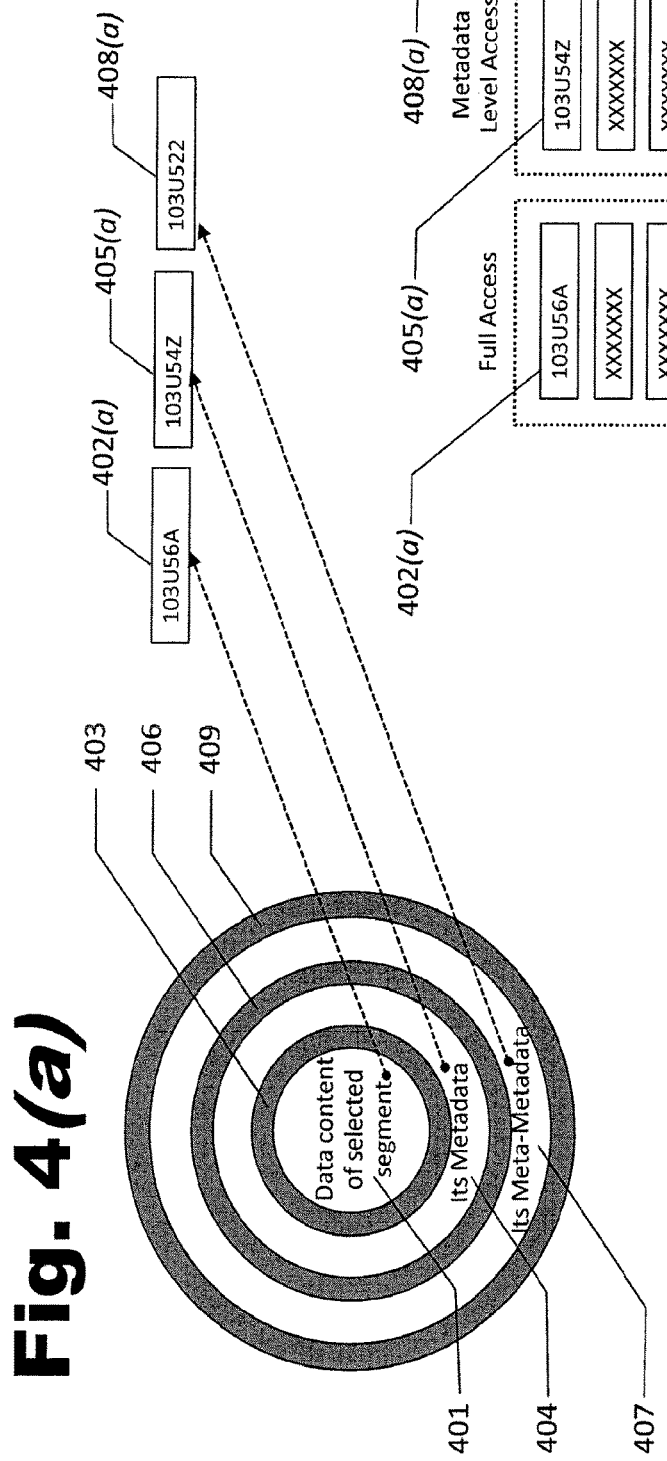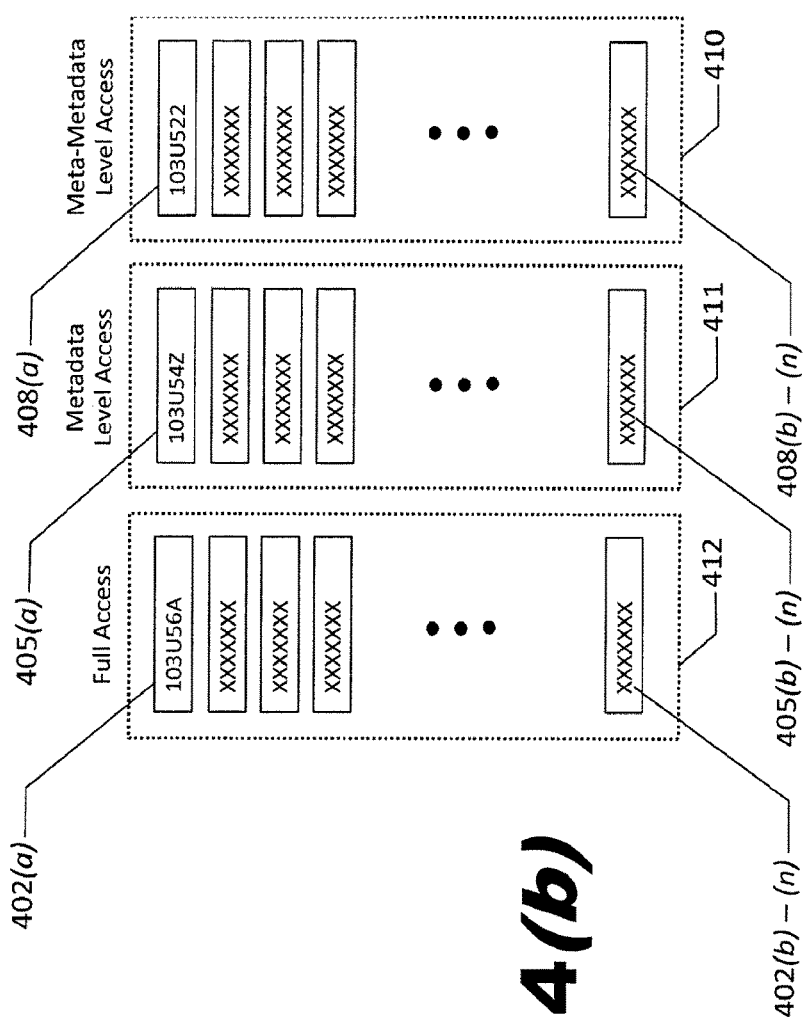
Fig. 4(a)
Fig. 4(b)

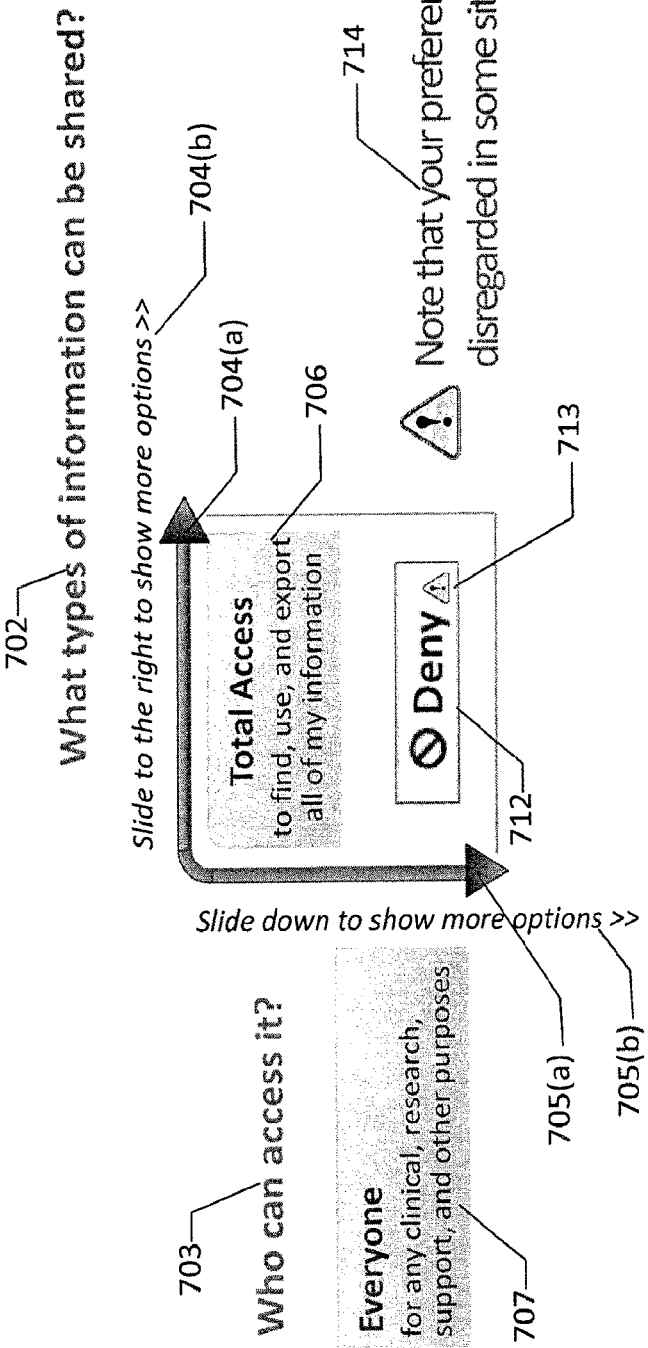

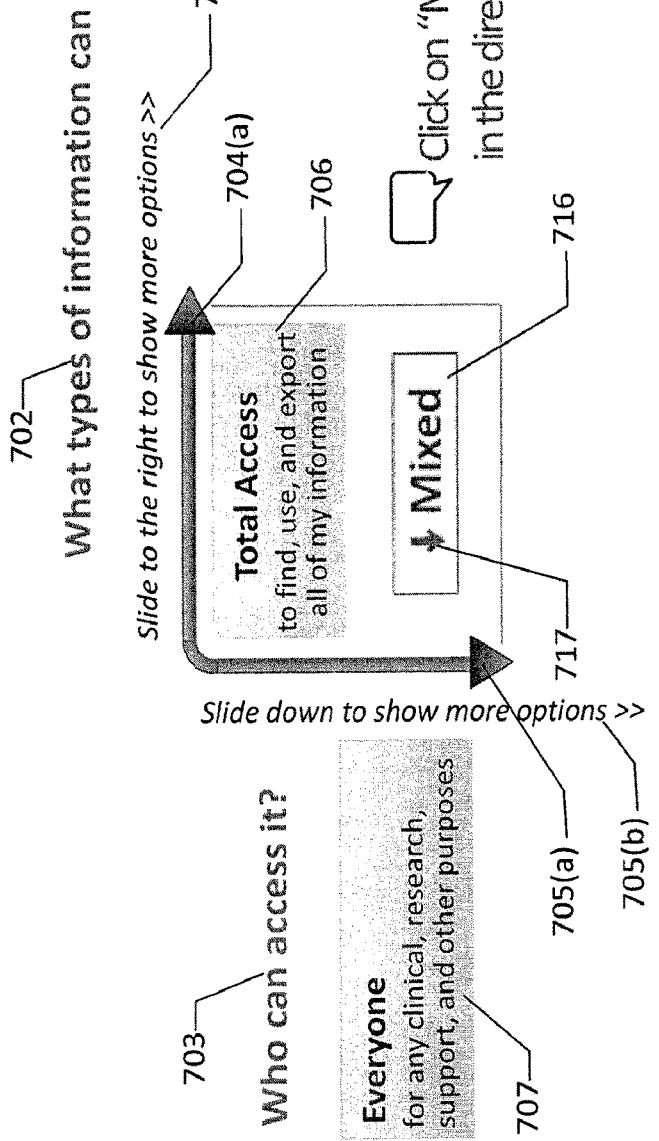

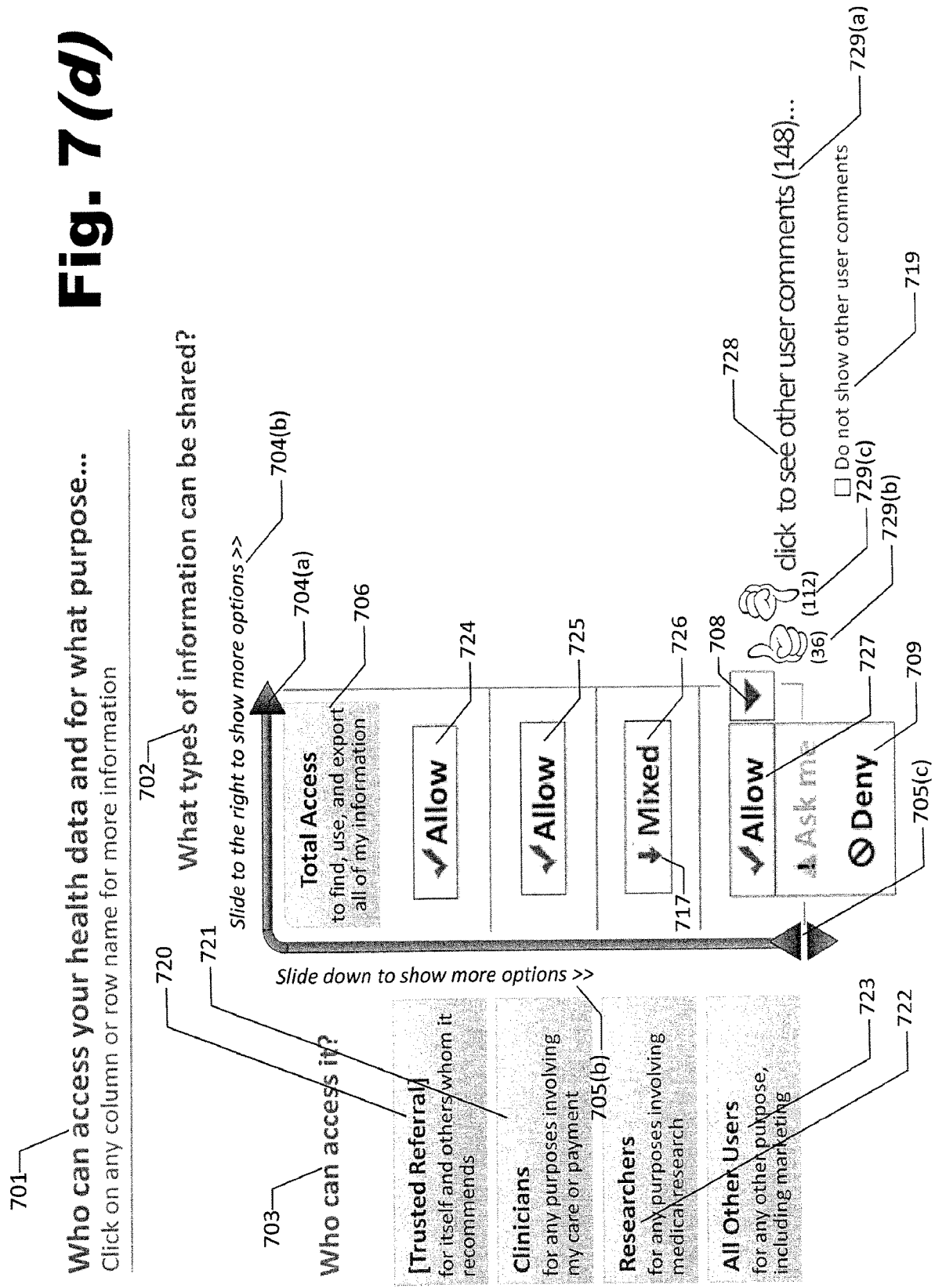

Fig. 7(g)

701 — Who can access your health data and for what purpose...
Click on any column or row name for more information 702 — What types of information can be shared?

704(a), 704(b) — *Slide to the right to show more options >>*

706 — Total Access to find, use, and export all of my information

716

758 — Mixed

718 — Click on "Mixed" to see more detailed settings in the direction shown by the arrow.

719 — ☑ Do not show this hint again

703 — Who can access it?

707 — Everyone for any clinical, research, support, and other purposes

705(a), 705(b) — *Slide down to show more options >>*

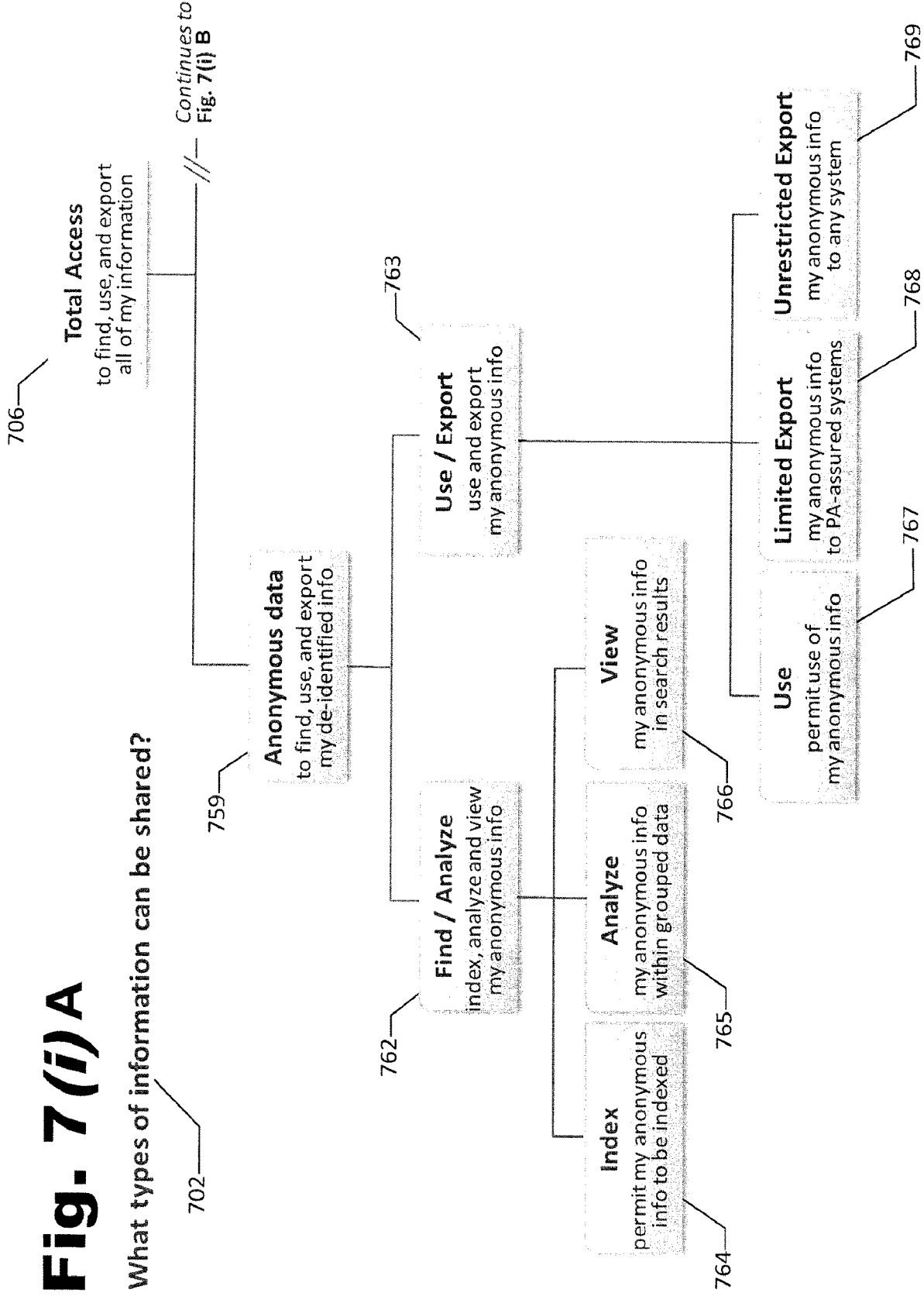

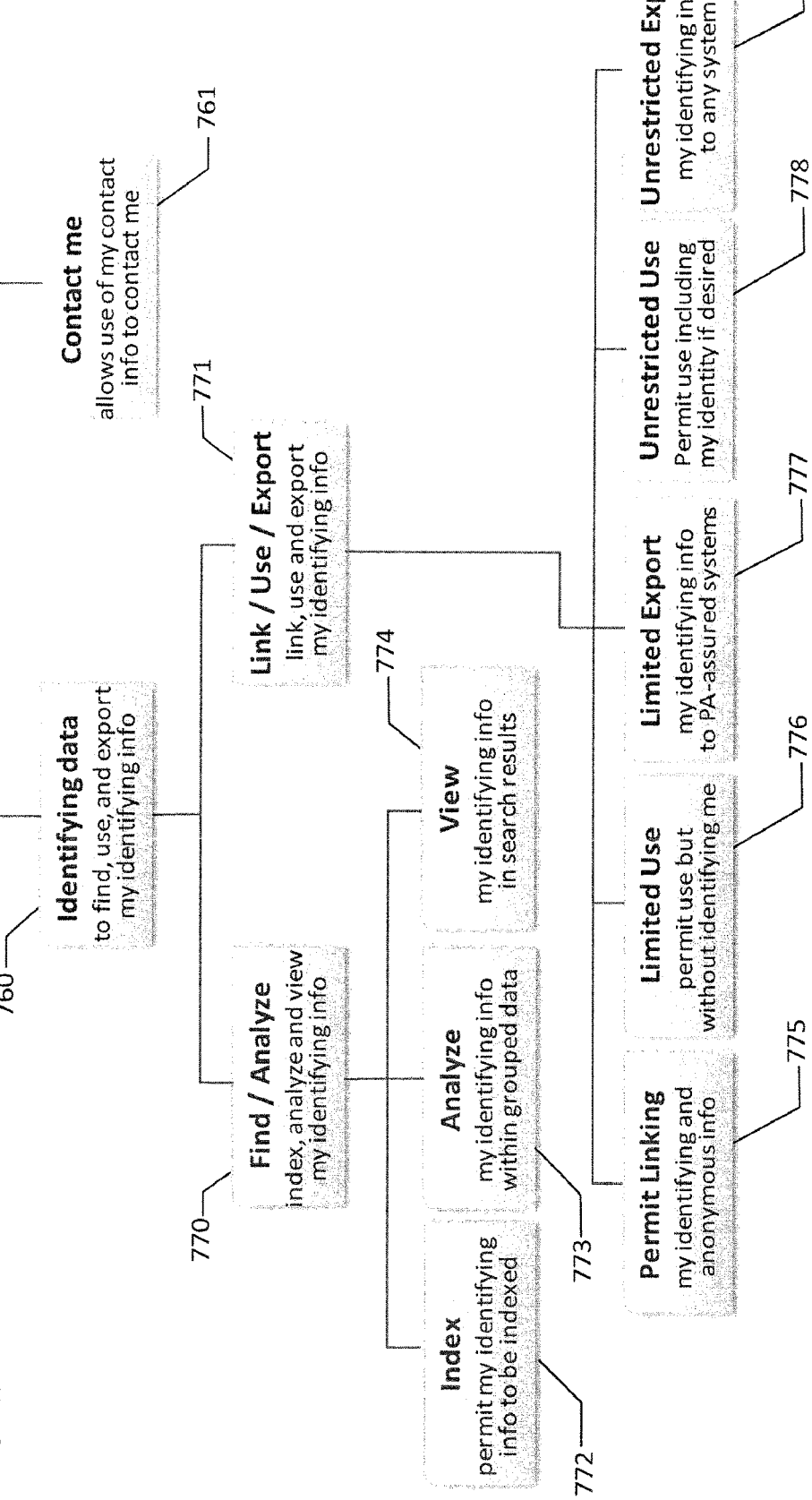

SYSTEM, METHOD AND APPARATUS TO ENHANCE PRIVACY AND ENABLE BROAD SHARING OF BIOINFORMATIC DATA

CROSS-REFERENCE TO RELATED APPLICATIONS

This application is a U.S. national stage application under 35 U.S.C. 371 of co-pending International Application No. PCT/US2016/023687, filed on Mar. 23, 2016, which in turn claims priority to and benefit of U.S. Provisional Patent Application Ser. No. 62/136,700, entitled: "SYSTEM, METHOD AND APPARATUS TO ENHANCE PRIVACY AND ENABLE BROAD SHARING OF BIOINFORMATIC DATA," filed Mar. 23, 2015, the contents of which is incorporated herein by reference in its entirety.

TECHNICAL FIELD

This disclosure relates to segmenting and controlling the flow of a wide variety of sensitive data including bioinformatic information over a network such as the Internet or an intranet, in communication with user preference repositories and policy repositories to enhance privacy protections for, and simultaneously to enable broad sharing and analysis of, such information.

BACKGROUND

Recent advances in Whole Genome Sequencing (WGS) and Next-Generation Sequencing (NGS) have dramatically improved the speed and throughput, reduced the costs, and improved the accuracy and richness of detail accessible through genetic sequencing. In just over a decade since completing (in 2003) the first full sequencing of a human genome at the cost of over a billion dollars, the cost of WGS dropped in 2014, with the release of Illumina's new HiSeq X™ system, to $1,000 for 30× coverage of a human genome, inclusive of instrument depreciation, sequencing consumables, DNA extraction, library preparation, and estimated labor for a typical high-throughput genomics laboratory. Reductions in cost and improvements in quality are forecast to continue, prompting a number of observers to predict that conducting a genetic test will in the future become as common as a urinalysis and blood test are today in the practice of medicine.

In order to increase the predictive value of such tests, and to discover new and better ways to improve health outcomes, diagnose and relieve chronic disease, and treat illness, there exists widespread interest in correlating longitudinal clinical detail, lifestyle choices, environmental exposure, and phenotypic information with the results from genomic sequencing. Researchers in public health agencies, academic, and commercial settings such as pharmaceutical firms, insurers, and governments are among the many parties located in countries all around the world who foresee the prospect for considerable benefit in accelerating innovation, reducing costs, and improving both their services and their profitability, through improved access to and use of such information.

The willingness to make ones' information broadly accessible is also relatively common among individuals who are affected by some complex conditions for which traditional diagnostic procedures and treatment modalities are today inadequate, their family members, and affinity groups which represent them. In addition to the general notion that generally healthy medical altruists feel about being among the first to do something new and the prospect of advancing scientific discovery, individuals who are affected by disease and their loved ones frequently are motivated by the hope that genetic analysis will be useful in ascertaining the source of unexplained symptoms, and thereby useful in reducing the "diagnostic odyssey" that is frequently experienced by patients with rare or exceedingly complex conditions, as well as in helping to identify more or less beneficial treatment regimes for their particular conditions. Indeed, such benefits are beginning to be demonstrated in various sub-specialties, including oncology for some forms of cancer, pediatric neurology, and with respect to some heritable disorders. And yet, proponents of the science—of which there are many—believe we have barely scratched the surface and that the contributions of these early adopters must be combined within hundreds of thousands, perhaps millions of others' equally detailed information to discover the playbook this blueprint contains.

As the price for WGS continues to decline and number of proven uses for exome testing and NGS increase, these early applications to help advance research and reduce the diagnostic odyssey for some rare conditions are anticipated to pave the way to so called "precision medicine" where the selection, dosage, and specific titration of a medication or treatment is custom tailored to what will be most effective to the individual patient. Getting to this point will require better ways to rapidly identify the appropriate (and increasingly, genetically appropriate) research cohorts for clinical trials, and once a personalized treatment has been sufficiently demonstrated as being efficacious, instituting faster and more cost effective ways to analyze the results of NGS and derive such conclusions, as well as improved means to disseminate such results broadly to treating professionals so that recommendations can be timely employed at the point of care or dispensing medication, and being appropriately remunerated.

Additionally, the trends of increased speed, ease of use, and rapidly declining cost of acquiring, analyzing, storing, and disseminating NGS data have greatly enhanced the prospects for broad "population genetics." Thus, what less than a decade ago would have been a prohibitively expensive and time-consuming process, has moved to the verge of being widespread, with major projects already announced and/or underway in a number of countries around the world. One example of these is the initiative by Genomics England to provide whole-genome sequencing by 2018 for up to 100,000 patients with genetically driven disease in the UK. Other significant initiatives are being considered literally all around the world, as research scientists, political leaders, commercial interests, and affected individuals and their families seek to take part in, and derive benefit from the explosive field.

By using data from these sorts of large population-wide initiatives (alone and in combination with information derived from clinical encounters and initiatives taking place in other countries), researchers hope to better correlate genotype, phenotype, lifestyle, and environmental exposure, and from such larger data sets and better analyzed and documented information within them, hope to accelerate and improve overall health outcomes and simultaneously reduce health care costs. Among the objectives that are frequently mentioned are reducing serious problems through better and more widespread carrier analyses, and assuring more timely interventions in the case of serious illness through non-invasive prenatal testing (NIPT), more comprehensive newborn screening panels, and tests conducted on DNA fragments ascertained in circulating blood that might someday become part of standard clinical protocols for preventative healthcare.

Some experts go so far as to express optimism that as the number of accessible genome sequences increases, and are subjected to analysis and the data shared, that researchers (and eventually practicing physicians) will increasingly be able to proceed from genotype to phenotype (rather than, as has heretofore commonly been the case, from phenotype to genotype) in developing and employing interventions that are of benefit to individuals with a predisposition to particular health problems. Others are optimistic this will result in identifying uncommon individuals—what some have called "accidents of nature"—who are, due to some yet-to-be-discovered mechanism, "protected" from adverse phenotypic consequences of otherwise problematic genetic variants, and from which observations and analyses, new treatments may be developed in the future.

The decline in cost and simultaneous gains in the speed and accuracy of NGS have to date exceeded the levels of improvement forecast by Moore's Law. And as experts look to the future, there is optimism that the field will similarly experience the kinds of exponential increase ($n^2$ or $n \times \log n$, etc) in overall value predicted by Metcalf's Law (or one of its corollaries) as the number of users sharing information as part of a network increases. Such gains inherently depend on the extent to which higher levels of participation in data sharing are practiced. And yet it is widely understood that openly sharing genomic information (particularly when such information is combined with detailed family health history) is not embraced by everyone. In point of fact, there exists substantial concern—and given the nature of genomic information, perhaps more so than any other form of health data—that such sharing be done with complete knowledge of the risks this entails and greater protections against misuse of the information that could be detrimental to the individual (as well, conceivably, as non-consenting blood relatives of the individual) from which the information is derived.

A 2009 article by Duke University professor and bioethics policy researcher, Misha Angrist, describes the vulnerability of genomic data, and its sensitivity to changing conditions due to continually improving data analysis technologies. Angrist observes:

Participant privacy and confidentiality considerations are mainstays of human subjects research involving genetics and genomics. Perhaps the most salient illustration of this can be found in the [ ] turbulence surrounding the NIH policy regarding genome-wide association studies (GWAS) data. In implementing its data-sharing policy in 2007, the NIH's expectation was that unless they could offer a compelling reason not to, NIH grantees would share their human genomic data with other investigators. It was also made clear that the decision to share or not to share could have tangible consequences: 'The ability to share, and the richness of the data for maximizing the usefulness of future research, may be considered . . . as part of award decisions'.

In 2011, the National Research Council under a contract between the National Academy of Sciences and the NIH convened a prestigious group of experts to consider the requirements and impediments of developing the sort of "Knowledge Network" required for advancing precision medicine. The final report, entitled "Toward Precision Medicine: Building a Knowledge Network for Biomedical Research and a New Taxonomy of Disease" identified privacy issues as a material impediment, stating in part:

The HIPAA required the federal government to develop regulations for protecting the privacy of personal health information. The HIPAA privacy regulations, which are intended to protect patient privacy, inhibit research that requires widespread sharing and multi-purpose use of data on individual patients in several ways (IOM 2009): First, rich molecular data about an individual (particularly whole-genome sequencing) could be considered a unique biological identifier under HIPAA, even if overt identifiers are removed. Although a waiver of authorization to use identifiable health information may be granted under certain circumstances, many health-care organizations are reluctant to participate. Secondly, because HIPAA does not allow authorization for unspecified future research or for several projects at one time, authorization must be given for each specific use of patient data. Thirdly, requirements for "accounting" to patients for research uses of data are burdensome and discourage data sharing. These regulations are strong deterrents to [precision medicine initiatives].

On Aug. 27, 2014, the National Institutes of Health (NIH) issued a new policy regarding genomic data sharing (see http://grants.nih.gov/grants/guide/notice-files/NOT-OD-14-124.html, accessed online on Jan. 19, 2015). The new policy (GDS Policy) provided an attempt to balance the benefit to be derived from more broadly sharing of this information; and yet as a prerequisite to such use, the decision to require more extensive participant consent that some researchers and institutions had treated as being unnecessary. The NIH's new GDS Policy establishes an expectation that all investigators generating genomic data should seek consent from participants for future research uses that enable "the broadest possible sharing to the greatest extent possible [ . . . including] for future unspecified use of their genomic data." (Emphasis added) And while the new policy expressly acknowledges that current forms of consent for future research uses and broad sharing of this data may not be adequate or obtainable in all circumstances, the GDS Policy indicates that the policy applies to all research regardless of whether it occurs in a clinical setting or involves data generated from deceased individuals; and says that "[t]he breadth of the sharing permitted by the consent may be taken into consideration during program priority review by the ICs [Institute/Centers]."

As explained on the Department of Health and Human Services' website, "The HIPAA Privacy Rule provides a Federal floor of privacy protections for individuals' individually identifiable health information. . . . State laws that are contrary to the Privacy Rule are preempted by the Federal requirements, unless [ . . . ] the State law [ ] relates to the privacy of individually identifiable health information and provides greater privacy protections or privacy rights with respect to such information." A similar deference to state law is contained in the Common Rule, which addresses data sharing in a research rather than clinical context, and that expressly states that "[the Rule] does not affect any State or local laws or regulations which may otherwise be applicable and which provide additional protections for human subjects." Moreover, the Common Rule expressly recognizes additional state requirements for informed consent, stating: "The informed consent requirements in this policy are not intended to preempt any applicable Federal, State, or local laws which require additional information to be disclosed in order for informed consent to be legally effective." Identical language appears in the regulations of the Food and Drug Administration.

As one example of the kinds of challenges that such preemptive rights present, in the State of New York, the legislature enacted a data sharing law specifically to protect the privacy of genomic information. Under the New York State Civil Rights Law, "all records, findings and results of any genetic test" may not be disclosed without the written informed consent of the person to whom the test relates, and the subject of the test must specifically identify any person or organizations to whom such information may be released. Referring to *N.Y. Civ. Rights Law §*79-I(2)(a). Moreover, the statute provides that "any further disclosure of genetic test results to persons or organizations not named on the informed consent require the further informed consent of the subject of the test." Referring to §79-I(2)(d). (Emphasis added)

Some individuals are fearful that WGS information may be used for racial discrimination, the denial of services due to genetic predispositions, and the disclosure of intimate familial relationships such as non-paternity. While some view such risks as being moot in contemporary society, others see these as palpable risks and cite to recent examples of capital punishment for infidelity in the Middle East, and ethnic cleansing in Eastern Europe, Africa and India, as palpable grounds for concern. Experts also warn that risks of retribution and adverse consequences conceivably could extend well beyond the person who is actually consented to being tested, including all of that individual's blood relatives such as siblings, children and grandchildren. Undoubtedly, such concerns arouse strong sentiments and, at times, quite extreme (and potentially counter-productive) reactions. Citing to concerns over the lack of adequate protections against misuse, millions of dried blood spots collected over a period of several decades through the nation's newborn screening program were permanently destroyed in several states as the result of court proceedings and lawsuits initiated by activists. Given the forensic value of genetic information (and the prospect that information acquired in a health context could make its way to law enforcement), concerns are often greater among ethnic and minority religious groups that have historically been the subject of discrimination.

Even where individuals are willing to share their information, there are presently a number of practical challenges. Current models for protecting health care data generally impose a legal obligation on the party receiving and/or holding the information (variously herein referred to as the "data holder", "resource holder" or "record holder", which terms are used interchangeably) to protect the information entrusted to them by patients in the clinical context, or subjects in the research context. This focus is codified in the legal and ethical frameworks that govern clinical practice and research activities in most countries, and impose financial and reputational penalties for violating such rules. The obligation does not extend to entities to which a covered entity or business associate might disclose personal health information (i.e., there is a lack of persistence of these privacy obligations). As a result, each entity with which the individual interacts (each doctor, hospital, insurance carrier, lab, pharmacy, etc.) effectively controls access to a different slice (both in substance and time) of a person's information. In turn, this leads to data "silos" because each institution separately administers only the data it receives and/or generates; and sharing this information broadly is not only challenging from a privacy perspective, but also contrary to the present incentive model in which control over large quantities of health data frequently has both direct and indirect economic and competitive value.

Privacy law differs substantially between the United States and Europe, beginning in its underlying philosophy. Generally speaking, in the United States, privacy laws focus on redressing consumer harm and attempting to balance privacy with efficient commercial transactions and the public interest; whereas in the European Union, privacy is treated as a "fundamental right" that can take precedence over other interests. In the United States "personally identifiable information" (PII) involves multiple and at times inconsistent definitions of PII that are often particularly narrow; whereas in EU, PII encompasses all information identifiable to a person.

In Europe, the data protection law is currently under review to take into account important considerations such as globalization and technological developments like social networks and cloud computing. Presently, it is expected to result in adoption of the General Data Protection Regulation (GDPR) in 2015, with enforcement expected beginning in 2017. While still under discussion, it seems likely that the GDPR will contain a number of aspects that create challenges for traditional biobanking activity and other bioinformatic data acquired with prospective approvals that are not explicit as to the intended purpose, recipients, third-country transfers, and type of data and consequences of processing at the time such consent is sought. And moreover, even the prospect that this will be the case has a chilling effect on development activity with regard to any form of traditional consent under the current state of the art. For a review, see "Open consent, biobanking and data protection law: Can open consent be 'informed' under the forthcoming data protection regulation?" (available online at http://www.lsspjournal.com/content/pdf/s40504-014-0020-9.pdf, accessed Mar. 2, 2015)

Similar to the challenges of variability of laws between states in the U.S., the disharmony in legislation between different countries carries repercussions for businesses attempt to function across disparate rules regimes. While popular and trade media has focused on the critical nature of this with respect to the Safe Harbor Rules, there exist potentially formidable challenges for medical researchers wishing to undertake broad comparative studies of bioinformatic data, and who are compelled to navigate multiple laws and regulations (each in flux from time-to-time) with different standards for access to and use of data.

Privacy challenges surrounding the research uses of clinical data have long been recognized; and the advent of genetic information has further exacerbated such concerns. WGS data is itself a "biometric identifier"—one of the 18 data elements the HIPAA Privacy Rule requires to be removed in order to render clinical data "de-identified". Law enforcement agencies utilize genetic data, and there have been striking examples of how easy it is to re-identify individuals using just a few elements of genetic information in combination with readily-accessible public data sets. As a consequence, clinical and research oversight bodies such as Institutional Review Boards (IRBs) and medical ethics committees—which generally focus on "protecting patients" by means of de-identifying and disconnecting data sets from patient identifiers as much as possible—are understandably confused about how to regulate genetic data sharing and genomic tests that rely upon access to such information.

Even in the clinical context, where applicable laws concerning treatment-related uses of information permit including NGS results in the electronic health record, significant problems are being encountered. Clinicians are increasingly concerned that if a specific variant is revealed—but that was not part of the intended use of the order and yet that has clinical significance (even later on)—they may be liable for that finding should it manifest in the tested individual in the future. Recent guidance released by the FDA and OHRP (Office of Human Rights Protection) further muddy the waters and limit innovation and novel research. Some experts question if including the WGS in the health record obligates a provider to take it into account (for example, when prescribing medications). Absent sophisticated decision support systems (DSS) to alert practitioners to the contents and potential applicability of such data, doing so could add materially to the time required to see patients, and highlight the lack of adequate training of most providers to properly assess and employ such information. In a risk adverse, litigious climate with the inability to better predict regulatory and judicial direction (let alone the speed of change taking place in medical knowledge in genomics, pharmacogenomics, and related fields), the "prudent" course is frequently to exclude the WGS from the patient's record, and to treat the information exceptionally.

In February 2009, the *European Journal of Human Genetics* published an article describing concerns about privacy, confidentiality, discriminatory and defamatory use of genetic data, and the complexities of informed consent for both research participants and their close genetic relatives in the era of personalized genomics due to, among other things, the potential for indirect estimation of genetic risk in an otherwise fully disclosed genome sequence. The authors described that they contacted Dr. Watson and his colleagues in December 2007 and February 2008 to "inform them of the possibility of inferring his risk for LOAD conveyed by APOE risk alleles using surrounding SNP data. As a consequence, the online James Watson Genome Browser (JWGB) has nominally removed all data from the 2-Mb region surrounding APOE." See Dale Nyholt et al. On Jim Watson's APOE status: Genetic information is hard to hide in European Journal of Human Genetics, February 2009, 17(2): 147-149 (Accessed online on Jan. 19, 2015 at http://www.ncbi.nlm.nih.gov/pmc/articles/PMC2986051/).

There are also a number of very practical considerations involved. The average raw genetic sequence file contains several hundred gigabytes of data, which must be processed to make sense of the data and identify the subset of functionally important variants. This process includes mapping, aligning, de-duplicating, merging, and comparing the observed variants to a reference genomic sequence, and from which annotation and medical recommendations may be derived. Whereas historically, brute-force computing has been employed to organize and make the sequenced data useful, this is both costly and slow, even with high-speed cloud-based computing centers.

Various methods have been proposed through which to expedite and reduce the cost of this pre-analytic step, with the prospect today of reducing the overall time required by handling the processing using a specialized integrated circuit chip and/or through gains in the speed of processing the data using software that is in turn realizing the benefit of Moore's Law sorts of efficiencies. While these recent innovations make it possible to now produce a file of several hundred megabytes in size that serves as the starting point for most variant analyses and diagnosis or treatment recommendations in a much shorter period, there remains a critical limiting factor in both cost and time required to analyze the raw sequence data.

A number of proprietary and open source based software tools have been proposed and are increasingly being employed through which to transform the data in the variant file or its equivalent from an output list of variants to an interpretation of the sequencing data. Generally speaking, these tools perform gene, region and filter based analyses and annotations, pull from reference data by numerous published and proprietary systems and annotations to identify individual variants, prioritize the identification of disease genes in an individual, family or population, and offer the knowledge of corresponding clinical implications and/or treatment recommendations in a summary report.

While privacy of the information is widely understood as being of critical importance, to date, relatively little has been produced in terms of privacy protective technologies. On the contrary, until relatively recently, most practitioners within the field have generally worked under the assumption that the biological samples and genomic information could be "de-identified" by removing references to the individual's name or any one or more of approximately two dozen expressly identifying characteristics (e.g., address, phone number, social security number, etc). However, relatively recently through the work of several leading researchers, this presumption has been irrefutably found to be erroneous.

Confounding the foregoing problems, almost all data sharing protocols chose a single point solution in what is commonly presented simply as the dichotomous option to either 'opt in' or 'opt out' of participating. Even in the few systems that move beyond this binary selection, a menu of narrow, static options is commonly offered. These consent systems generally produce fixed and unalterable choices, unmindful that personal and public context is highly changeable even over short periods, and devoid of the other essential elements that are addressed in the system and method disclosed in Applicant's U.S. Pat. No. 9,032,544 (System and method for controlling communication of private information on a network), herein the '544 patent, the teachings of which are incorporated herein by reference.

Genomic data is considered by many, if not most, people to be "intrinsically private" (as has been held by the European Court of Human Rights, or ECtHR) inasmuch as a massive number of traits can potentially be analyzed from any given sample. These include physical attributes (such as blue eyes, brown hair, detached ear lobes, etc), as well as current or future medical (has condition A, does not have condition A, is X% likely to contract condition A in the future) and/or social status (has genetic predisposition toward social characteristic S), and may be held in common with others (for example blood relatives). Moreover the content and amount of information that can be extracted from the genome is increasing at an exceptionally fast pace, such that all anyone can predict with relative assurance at this point is that the content, form and specificity of information about an individual that can be extracted from a sample will be greater in the future than it is currently. The foregoing has led the ECtHR to opine that "the Court cannot discount the possibility that in the future the private-life interests bound up in genetic information may be adversely affected in novel ways or in a manner which cannot be anticipated with precision today."

Although a modest number of genes are required for lead validation and pharmaceutical genotyping, a large number of compounds and patient samples are required to obtain meaningful statistics to support the derived linkage information. Similarly, although DNA diagnostics and clinical genotyping commonly require only a modest number of genes, identification and refinement of these techniques relies upon very large sample populations. And whereas high levels of confidence in diagnosing mutation and infectious diseases rely on a modest number of genes or SNPs, a great number of individual samples must be tested and analyzed to achieve widespread application. Whereas ultimately, clinical genotyping to support personalized medicine will likely require very small gene sets to indicate such attributes as toxicological and treatment response, high throughput must be achieved in order for this to be meaningful to large populations. An improved means to address privacy considerations and build trust, and that overcomes the limitations in the current approaches to privacy and security is critical to attaining such goals.

SUMMARY

This disclosure provides a system, method, and optional apparatus for overcoming the limitations described in the Background discussion; enabling on the one hand, substantially greater protections for the privacy of bioinformatic data including whole genome sequencing data, while simultaneously broadening access to such data and increasing its usefulness in clinical, diagnostic, research and other market contexts. Contrasted with existing methods for protecting the privacy of such sensitive data (which dramatically reduce the accessibility and/or degrade the data's utility) and traditional methods for making the information more accessible and its uses (which are accompanied by an increase in privacy risk), the disclosed system, method and apparatus represent a material improvement over the current state of the art.

These improvements accrue through the disclosed system and method of segmenting and controlling the flow of the data over a network such as the Internet or an intranet, in communication with user preference repositories and policy repositories to enhance privacy protections for, and simultaneously to enable broad sharing, analysis and use of, such information. The system and method may be performed using specially programmed computer processors or, in one preferred embodiment, may be executed through use of a hardware processing platform, such as an integrated circuit, to locate key regions within such data, to assign metadata and index such information, and to implement privacy-aware access controls with respect thereto. In each case, such steps can be employed either as a standalone process, or preferably as an integral part of performing one or more functions that are already required in analyzing and processing such data. These steps may be performed locally (meaning at the same location where the sequence is produced), or in the cloud or other virtual private network. And in one optional preferred embodiment, some or conceivably all of these steps may be performed using homomorphic encryption to protect the content about which the function pertains while simultaneously enabling the functional step to be processed and a meaningful result provided.

In the one preferred embodiment, the disclosed preparation and specialized processing enables said data set to be incorporated in a searchable public index from which it can be queried, accessed, used, and/or made accessible to being shared with others pursuant to robust privacy protective protocols that optionally accompany such data elements. The preparation preferably also enables maintaining data provenance and audit reports, eliminating undesired duplication of records, and for verifying downstream conduct of those who receive access to the data, while simultaneously enabling the parties or entities that are the source or author of the privacy directives (or their representatives, collectively herein "grantors") to change their direction over time, as circumstances, associated consequences, and perceived needs arise. In yet another one preferred embodiment, the disclosed system and method enables calculation and distribution of fees, attribution, and other value produced through sharing such information with others, as and when permissible in accordance with such privacy protocols.

Although these steps may be performed through specialized software, in one preferred embodiment, such processing is performed using a hardware accelerator, such as an integrated circuit, to enable the steps to be performed in one or more hardwired digital logic circuits that may be interconnected by a plurality of physical electrical interconnects, and that can be arranged as a set of processing engines, wherein each processing engine is capable of being configured to perform one or more steps in segmenting, assigning various metadata elements, indexing, compressing, encrypting, and assigning one or more codes that associate directly or indirectly to the then current instantiation of the privacy directives (in law, local institutional policy and patient privacy preferences) governing such data element.

BRIEF DESCRIPTION OF THE DRAWINGS

FIG. 3 is a system block flow diagram for segmenting, assigning metadata, indexing, compressing, encrypting, and associating one or more unique codes that associate directly or indirectly to the then current instantiation of the privacy directives governing access to such data element at the time access thereto is sought by a data seeker, in accordance with an illustrative embodiment of the invention;

FIG. 4 is a simplified illustration showing one preferred arrangement of such one or more indexable metadata, encryption, and assignment of globally unique identifiers for such data and metadata elements, in accordance with an illustrative embodiment of the invention;

DETAILED DESCRIPTION

Figure 1C:
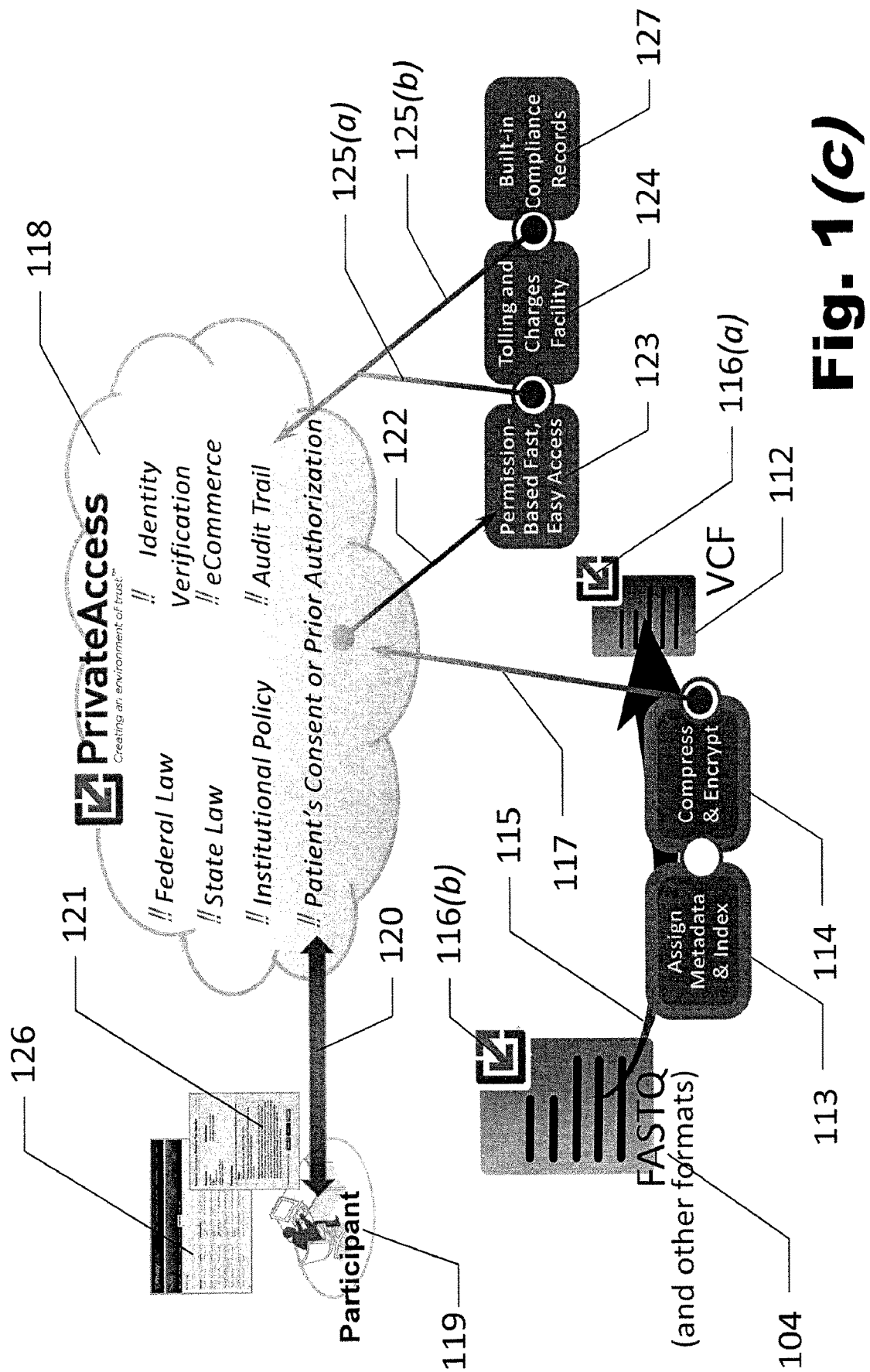
FIG. 1, consisting of three subparts, illustrates the major steps involved in practicing the invention, including in subpart 1(a) the phases of information processing that are currently involved in producing an individual digital genetic code from a sample and identifying variants therein, and in subparts 1(b) and 1(c), the additional steps involved in practicing the system and method disclosed herein in accordance with the teachings of the invention, including through use of the apparatus.

Detailed embodiments of the present invention are disclosed herein, however, it is to be understood that the disclosed embodiments are merely exemplary of the invention, which may be embodied in various forms. Therefore, specific functional details disclosed herein are not to be interpreted as limiting, but merely as a basis for the claims and as a representative basis for teaching one skilled in the art to variously employ the present invention.

In an illustrative embodiment of the invention that is described herein with reference to FIG. 1, subpart 1(a) illustrates the current state of the art involved in generating digital genetic code for an individual and determining the variants present in that individual's genetic makeup compared with a reference genome. As shown in FIG. 1(a), the process begins with collection of a biological sample 101, consisting of blood (as shown for illustrative purposes), or alternatively any number of acceptable materials such as saliva, hair, tissue, or the like.

This sample is then prepared using established laboratory techniques and loaded into a sequencing device, 102. In a non-limiting example, FIG. 1(a) shows use of Illumina's HiSeq® X device, which was released in February 2014 and advertised as being the world's first sequencing platform to break the $1000 barrier for 30× coverage of a human genome. Persons of ordinary skill in the art will be aware there are a number of competing devices; Illumina itself offers a line of machines of different speeds, cost and throughput capacity; and there are in development next-generation machines that may be used in the future. Any such machines performing the function of converting an individual's genetic code into machine-readable digital code, 103, are suited to employ the practices of this invention. Similarly, a wide variety of machines and other devices that produce other types of bioinformatic data may employ the teachings of the invention and are thus encompassed by this illustrative case; and the output thereof is expressly intended within the reference to machine-readable digital code 103.

In the present example, such machine-readable code is saved to a FASTQ file 104, whose size is commonly in the range of several hundred gigabytes or larger depending on the levels of coverage applied. The identification of a particular file format is intended solely for illustrative and not limiting purposes, as this disclosure is intended as broadly as possible to pertain to any file or intermediate work product (such as a FASTA, BCL, BAM or SAM file, etc.) comprising the data 103 educed during the process of sequencing sample 101, now or in the future.

During the next processing phase, such generated digital genetic code is used in determining the individual's genetic makeup, e.g., in determining the individual's genomic nucleotide sequence. Under the current state of the art, during the processing that typically comprises this phase, the raw data contained in the FASTQ file 104 is sent using known conventional means 105 for file access (if the work will be performed locally) or transport (if, for example, the processing will be performed at a different location or using cloud-based processors) to one or more computers 106(a) or to a hardware platform such as a specially designed integrated circuit chip 106(b).

The data from the millions of reads stored in file 104 is then mapped and aligned, sorted, and de-duplicated. Rectangular boxes 107, 108 and 109, respectively, represent these steps. As part of sorting, arranging and/or de-duplicating the data so that it appears in the proper alignment, or after the data is arranged to be in the proper alignment through such steps, the processing also identifies differences (i.e., variants) between the assembled genome of the individual and a reference genome. This process is represented by rectangular box 110, entitled "variant calling", and identifies how the individual's genetic makeup differs from that of the referent(s). Persons of ordinary skill in the art will understand that this description of the prior art represents a simplified explanation that highlights the major steps involved in such processing of the raw data that will be useful in this disclosure, and that there are other functions such as local realignment, duplicate marking, base quality score recalibration, compression, decompression, and other functions that may take place as part of these steps and which, depending on the methods and objectives of the sponsor of such work may take place during the course of such intermediate processing.

Under the prior art, once the variant calling process is completed (inclusive of such additional functions), the data is written to a file, indicated by arrow 111, in "Variant Calling Format", to produce VCF file, 112, employing a standard that lists and annotates the entire collection of human variants. The VCF in its basic form is a list of locations of variants and their type: e.g., chromosome 3, at position X, an "A" is substituted for a "T", etc. As the field develops, such file may be modified, supplemented or replaced with one or more other formats that incorporate additional aspects of the genome. For the purposes of this disclosure, any such file that serves as a predicate for analysis and so called tertiary processing of such information is intended to be encompassed within the meaning of VCF file 112, as used herein.

As previously noted, this intermediate processing may be performed using specialized software such as Illumina's HiSeq® Analysis Software (HAS) or other open source and/or proprietary software running on computer server(s) to provide a full spectrum of variant types. Such variants include single nucleotide variants (SNVs), indels (inversions and deletions), structural variants (SVs), and copy number variants (CNVs). Depending on the sequencing equipment and the preferences of the laboratory or sponsor for the work, this processing may take place within the sequencer equipment itself, or may take place using computer hardware that is located on-site, computers located at another location, or within a cloud-computing environment such as Amazon Web Services, Google's Genomics platform, Illumina's BaseSpace® genomics cloud-computing environment, or the like. All of these alternative means are represented by servers 106(a) shown in FIG. 1(a).

Various methods have been proposed through which to expedite and reduce the cost of these pre-analytic steps, including through optimized pipeline software and the prospect of reducing the overall time required by handling the processing using a specialized integrated circuit chip. U.S. patent application Ser. No. 14/180,248 (Bio-informatics systems, apparatuses, and methods executed on an integrated circuit processing platform), filed on Feb. 13, 2014, by Pieter Van Rooyen et al., and assigned to Edico Genome, Inc. (herein the '248 application), discloses processing such data within a hardware platform such as a specially designed integrated circuit containing technologies for performing one or more of such mapping, aligning, sorting, local realignment, duplicate marking, base quality score recalibration, variant calling, compression, and/or decompression functions. Such hardware is represented by computer card and specially programmed integrated circuit chip 106(b).

The '248 application also describes that in various embodiments, a bioinformatics processing regime may be employed within such apparatus for the purpose of creating one or more masks, such as a genome reference mask, a default mask, a disease mask, and/or an iterative feedback mask, that may be added to the mapper and/or aligner, e.g., along with a reference, wherein the mask set is configured so as to identify a particular area or object of interest. And as described therein, in one embodiment of the methods and apparatuses disclosed, the mask set is configured so as to identify areas of high importance and/or relevance, e.g., to the practitioner or subject, and/or so as to identify areas having increased susceptibility to errors.

It is well understood that once a VCF file has been generated, the data it contains may be subjected to various forms of tertiary processing and analyses to interrogate, interpret, and draw conclusions concerning the individual to whom such digital code pertains. Such tertiary analyses may be performed for a variety of useful purposes, including assisting in diagnosis, targeting treatment (perhaps even in advance of any adverse health problems), advancing research, and for forensic uses. And yet, like most powerful tools, such tertiary analyses also can be misused and/or abused, for example as a means to re-identify data that was intended to be kept anonymous, as the basis for various discriminatory practices, stigmatization, termination of otherwise viable fetuses, and at its extreme, retribution, eugenics and ethnic cleansing.

Given the potential both for beneficial uses as well as highly detrimental misuse, the importance of ethical uses of such information has been emphasized since the inception of the genomics age. Ethicists have long appreciated that the widespread ability to uncover genetic predispositions and one's very identity through analysis of ones genomic sequence has significant implications for individuals, their families, and society as a whole. Because genes are considered highly significant (and in some cases central) in determining who a person is and what challenges or strengths he or she is likely to exhibit, information about genetic mutations may cause a person to change his or her self-image, and may alter the way others treat that person.

The prospect for such information to be misused or misunderstood has lead to legal and ethical expectations designed to assure (with the exception of the criminal context) the rights of individuals to determine for themselves whether or not to pursue genetic information, and allowing those who choose to do so to derive benefit from the new genomic tools free from fear of the negative uses of such information. Nevertheless, as described in the Background section, there has heretofore been no viable means by which to assure the privacy of the information without simultaneously reducing its broad accessibility and/or utility; and no means by which to maximize its use and dissemination, without simultaneously increasing such privacy concerns. One of the primary objectives of the instant system, method, and apparatus is to enable faster, more effective, and broader attainment of the positive aspects; and simultaneously to minimize the risk of the negative ones.

Turning to FIG. 1(b), in a preferred embodiment of the invention, two additional processing steps are introduced as part of the aforementioned intermediate processing phase. Rectangular box 113, entitled "Assign Metadata & Index", refers to identifying and associating various structures (i.e., segments) within the individual's genome, and associating these with metadata as more particularly described in connection with FIGS. 2, 3 and 4 hereof. And rectangular box 114, entitled "Compress & Encrypt", refers to optionally compressing and encrypting each such segment, so that in a preferred embodiment, these segments may be separately located and access to such data contained therein controlled in accordance with the principles of the invention and Applicant's related prior inventions.

As persons of ordinary skill in the art are aware, a number of well known means exist for identifying the beginning and end points of particular genomic structures; and once so identified, creating or deriving metadata associating therewith, compressing, and encrypting such data segments and/or metadata. Such steps may be undertaken through the use of specially programmed software (or updates made to existing software) run on servers 106(a); and in a preferred embodiment, would be performed through the use of hardware such as a specially programmed integrated circuit chip 106(b), wherein masks such as those described within the '248 application or their equivalent are utilized in accordance with the principles of this invention.

In various embodiments, as seen with respect to FIG. 1(b), said processing chip may be part of a circuit board, such as part of an expansion card, for instance, a peripheral component interconnect (PCI) card, including a PCIe card, which in various embodiments may be associated, such as, communicably coupled, e.g., electrically connected, with an automated sequencer device so as to function part and parcel with the sequencer, such as where the data files, e.g., FASTQ files, generated by the sequencer are transferred directly over to the chip, such as for secondary genomic processing, such as immediately subsequent to the FASTQ file generation and/or primary processing, e.g., immediately after the sequencing function has been performed.

In an optional embodiment, such processes could also be performed after writing VCF file 112, although in a preferred embodiment these steps would be performed coincident with the processing involved in the aforementioned mapping, sorting, and variant calling steps. This preference is indicated by the substitution of arrow 115 in FIG. 1(b) for arrow 111 under the prior art, representing such processing pipeline in whatever order, whether sequential as shown or iterative in its nature, best suits the objectives of the invention, culminating in writing said data to VCF file 112, which in one preferred embodiment would also be associated with appropriate metadata, indexed, compressed, and encrypted.

The addition of private access symbol 116(a) in association with said document is intended as a means for distinguishing a traditional VCF file 112 such as shown in FIG. 1(a) from one that incorporates, as described in relation to FIG. 1(b), the foregoing at least two or more segmented and preferably separately encrypted elements. Additionally, in another one preferred embodiment of practicing the invention, during the course of such intermediate processing, data contained on the foregoing FASTQ file 104 would simultaneously be segmented, associated with the appropriate metadata, indexed, compressed and preferably separately encrypted in a number of logically organized packets of data preferably corresponding to said at least two or more separately encrypted elements in said VCF file 112. The addition of private access symbol 116(b) in association with said document indicates such enhancements.

Finally, FIG. 1(c) illustrates how in a preferred embodiment, these additional features are integrated with Applicant's previous teachings, and some of the functional utility of such integration over the prior art. As shown thereon, arrow 117 indicates incorporating data elements (or references to said data elements) produced during the foregoing process of associating the appropriate metadata with privacy directives associated therewith and indexing said information. In this regard, Applicant's '544 patent teaches the use of unique data element identifiers "such as GUIDs (globally unique identifiers), DOIs (digital object identifiers), 'Handles' and the like to represent this data" and associate it with one or more privacy directives provided through a private access bureau 118, while leaving, in a preferred embodiment, such data at the location and under the immediate control of the data holder such as the laboratory where the sequencing is performed, a provider receiving the results of such testing protocol, a researcher, and any number of other parties and applications who hold the data. In said '544 patent, the contents of which are incorporated herein by this reference, Applicant teaches:

> ... a system and method for regulating the flow of data including private information over a network, and more particularly for establishing and operating a privacy decision point, authorization manager, bureau or the like (collectively referred to herein as a "private access bureau") in communication with user preference repositories and policy repositories for controlling access to private information over one or more networks, including the Internet.
>
> While a private access bureau may be established for a single enterprise, geographic area, network, or market segment, in one illustrative embodiment, the private access bureau is established as a consumer-centric, cross-industry facility such that its user preference repositories and policy repositories are utilized by multiple entities, enterprises, websites, online services, networks, and other data holders, data seekers and data subjects. Also, in another illustrative embodiment, the private access bureau (or a few such competing bureaus as is the case for consumer credit ratings bureaus) is independent and privacy policy-agnostic (meaning that it takes no position on whether data that its systems and services help to regulate should be shared widely or maintained as being strictly confidential) so that consumers and data holders have less reason to doubt that the actions of the private access bureau [will be] tainted by an agenda beyond fulfilling its intended purpose of regulating the flow of such data in accordance with then applicable policies and personal privacy preferences. Any systems that confer and to the extent applicable, base their actions to control access to or sharing of data they are holding based on privacy directives received from the private access bureau are collectively referred to herein as being "privacy-enabled," and the applications and services employed by them as being "privacy-assured".

Thus, by employing the teachings of the instant invention, any parties holding, accessing, and using genomic information can become privacy-enabled, as more particularly described within said '544 patent. By way of summary and not limitation of such detailed disclosure, cloud 118 shown in FIG. 1(c), preferably includes the ability for disclosures of such genomic information (and in one preferred embodiment, specific segments thereof and/or in another one preferred embodiment wherein said information disclosures are processed in said cloud 118 using homomorphic encryption techniques to ensure that the processor is unable itself to know the nature of the content data about which it calculates such permissions directives) to take into account jurisdictional rules such as federal and state law (in the US and other countries, including treaties between nations, to the extent applicable); institutional policy (including how conservatively or aggressively the data holder wishes to interpret issues such as de-identification, the risk for re-identification, and the imposition of financial charges applicable to gain access to and/or release of such information); and the wishes of the individual about whom such information pertains (including through prior authorization and/or dynamic consent, i.e., at the time access to such information is requested by a data seeker). Additionally, such private access bureau functionality can, in one illustrative embodiment, address in a federated manner the needs for identity verification (e.g., with respect to the data holder, data seeker, the party (or parties) whose information is being sought, and the data element in question); electronic commerce (thereby enabling transactional charges to be assessed and revenues from such transactions to be distributed in accordance with terms established by the parties involved therein or consenting thereto); and for maintaining an independent audit trail of the foregoing activities and in one preferred embodiment a record of data provenance.

As more fully described in said '544 patent, the private access bureau enables integration of participant 119, who it will be understood represents the individual who is the subject of said genomic data, non-limiting examples of which include a patient, a healthy volunteer in a research study, or anyone who elects to have their genome sequenced. Although not pictured, in certain optional cases, a participant may also be a blood relative of said individual to the extent that the then applicable law or public policy, institutional policy, or an individual grantor's wishes result in needing such party's express approval for certain types of disclosures, or in the event an individual wishes to designate a person to act as a proxy on his or her behalf. In a preferred embodiment of the bureau, the participant may also be an individual designated by the institution or jurisdiction to act on that entity's behalf in expressing the laws or policies of said enterprise or jurisdiction within the rules database employed by the bureau, and/or over-riding such rules should an exception be dictated or in instances where an instruction to "Ask Grantor" reflects that such law or policy to "allow" or "deny" access or sharing is to be based solely on a case-by-case determination being made.

Two-way arrow 120 illustrates the bureau's ability for such participant 119 to enter his or her personal privacy preferences (and in the other instances referred to herein, in accordance with their respective authority to do so, to enter rules reflecting such jurisdictional laws and/or institutional policies). Said two-way arrow also reflects said participant's ability to revise or update these entries from time-to-time, and to receive notifications where appropriate, and respond thereto with specific consent. In a preferred embodiment, such entry would be expressed using a standards-based ontology and communication means that reflects the semantic elements taught in the '544 patent, and further described in connection with FIG. 5 hereof. An illustrative example of such communication supporting dynamic consent is provided in message 121, which may employ any standards-compliant web browser, phone, or mobile device to convey information regarding a proposed action and such otherwise protected data, and as shown, to provide various options that a properly authenticated recipient of such notification may take with respect thereto.

Arrow 122 illustrates communication to said data holder of advisory information regarding the applicable law, institutional policies, the affected participant's wishes, and prospective remuneration (if any) for granting access to the protected data (or in some cases, mere metadata) to which such privacy directives pertain. In a preferred embodiment, the private access bureau 118 serves as a policy mediation point (PMP) and the data holder continues to function as a policy enforcement point (PEP). Nevertheless, persons of ordinary skill in the art will appreciate that having ready access to the then current instantiation of such potentially changing information upon which to base such enforcement decision enhances data liquidity, as reflected by rectangular box 123, entitled "Permission-based, fast, easy access" (e.g., when and as permissible). Persons of ordinary skill in the art will also appreciate that where, in one preferred embodiment, the information that is uploaded to the private access bureau 118 is first encrypted by the data holder using a technique such as homographic encryption, that said guidance by said private access bureau may be processed and returned in communication 122 in an encrypted form that is decrypted upon receipt by said data holder, and thereby permitting the private access bureau to process its decisions that take into account all of the information described with respect to FIG. 5 hereof without ever knowing any thing about the content of such attributes except that the data holder processed a request and received an answer to allow or deny [some action], or alternatively that triggering a pre-programmed ask grantor process. Persons of ordinary skill in the art will appreciate that by use of such specialized encryption approach, the need for the private access bureau to be a "business associate" or equivalent of the data holder may be avoided and a number of attendant advantages.

Persons of ordinary skill in the art also will recognize that various standards such as XACML (eXtensible Access Control Markup Language), XSPA (OASIS Cross-Enterprise Security and Privacy Authorization), SAML (Security Assertion Markup Language), WS-Trust and WS-Security, OAuth 2.0, and Open ID Connect; and evolving standards such as HL7's FHIR (Fast Healthcare Interoperability Resources) and the Kantara Initiative's UMA (User-Managed Access) profile based on OAuth 2, may be useful in carrying out various portions of the foregoing principles of the invention. In a preferred embodiment, said private access cloud-based service 118, also includes ecommerce capabilities for enabling charges to be established (for example, on a subscription and/or transactional basis) for such access, as illustrated by rectangular box 124, entitled "Tolling and charges facility".

As shown, arrow 125(*a*) illustrates the capture and reporting of data regarding said data holder's decision to allow access to or share said protected information, and arrow 125(*b*) illustrates the capture and reporting of any charges and payments associated therewith. Such information is captured in said private access bureau 118, and in turn is communicated (or made accessible) to the appropriate participants through audit report 126, reflecting such activity and fulfilling, among other things, the regulatory obligations for maintaining an "accounting of disclosures" of data sharing and a record of the authority and permissions that form the basis for compliance with the underlying laws, policies and participant wishes (or where there is a deviation, i.e., should a data holder elect to "break the glass" and override such policy mediation advisory and act in a different manner, and the basis for such action). This is illustrated by rectangular box 127, entitled "Built-in compliance records". Persons of ordinary skill in the art will be aware that the U.S. Department of Health and Human Services and the U.S. Food and Drug Administration (FDA) recently issued standards concerning the use and processing of electronic informed consent (see http://www.hhs.gov/ohrp/policy/faq/informed-consnet/can-electronic-signture-be-used-to-document-consent.html and http://www.fda.gov/downloads/Drugs/GuidanceComplianceRegulatoryInformation/Guidances/UCM436811.pdf respectively). In one preferred embodiment, said private access bureau activities will additionally incorporate the step of securing the participant's informed consent to one or more proposed medical procedure(s) and/or research protocol(s) as an integral step in the foregoing participant engagement activities, said additional processing being in accordance with said HHS and/or FDA standards from time to time (or the local law equivalent thereof, when in a country other than the United States, or where governed by a different regulatory agency).

Turning next to FIG. 2, which is comprised of five subparts, an illustrative embodiment is presented for the process of segmenting the individual's genomic information, and establishing individually controlled access to selected potions of said segmented genomic information in accordance with the principles of the invention.

The first such subpart, FIG. 2(*a*), provides a graphical illustration of a typical chromosome, 201, and the International System for Cytogenetic Nomenclature (ISCN) mapping system that is used to consistently number and illustrate chromosomes in the form of an ideogram, 202. As shown, each chromosome is comprised of a very tightly wound strand of coiled DNA 203. Unwinding the coiled DNA strand reveals its form as a double helix, 204, comprised of four chemical bases, 205, Adenine (A), Cytosine (C), Thymine (T), and Guanine (G), arranged in a sequence of base pairs (A with T, C with G), 206.

FIG. 2(*a*) also shows the component parts of an ISCN ideogram for a typical chromosome. As illustrated therein, these consist of the so called short (p) and long (q) arms, 207, each of which are comprised of several numbered regions, 208. In turn, these regions are comprised of one or more bands, 209, and in some cases two or more sub-bands, 210, all of which refer in the current state of the art to a particular position within the chromosome, and therefore a particular segment of the DNA strand, 203, and corresponding section of base pairs, 206, located within that chromosome.

It is well understood that in humans, in the absence of a chromosomal abnormality or variation, the genome most often consists of 23 pairs of chromosomes, found in the nucleus of cells, as well as a small chromosome found in the cells' mitochondria. These chromosomes, taken all together, contain approximately 3.1 billion bases of DNA sequence. FIG. 2(*b*) shows an illustration of the ideograms for all 23 chromosomes plus mitochondrial DNA, 211; and indicates that in a preferred embodiment of the invention, there is provided a means for enabling whole genome accessibility, 212, which it will be understood refers to a single permission enabling the entire set of genetic instructions to be revealed or concealed. Thus, allowing access at the whole genome level would open all of this information for the individual's genome to the party, entity or application desiring such access (in each such instance herein a "data seeker"); and prohibiting access at this level would preclude access to any of this content by said data seeker. As disclosed in Applicant's '544 patent, a third option (therein referred to as "Ask Grantor") may also be applied to condition access to said whole genome upon a response by the participant (i.e., commonly referring to the individual to whom the genomic data pertains, although depending on the particular context, someone else such as a parent or legal representative could act on their behalf as the pertinent grantor) to a specific request for access to such information.

In one preferred embodiment, the beginning and end of that portion of the individual's genomic sequence contained on each of such chromosomes 211, is identified as an independent level of access control. As illustrated in FIG. 2(*b*), such identification of the individual chromosomes results in the prospect for selecting one or more chromosomes, such as by clicking on the ideogram for such chromosome of interest to produce rectangular box 213, indicating in such example the selection of Chromosome 3, or by designating the one or more desired chromosomes by entering said chromosome number in field 214. In either the case, such segmentation of the whole genome into chromosome-level elements would enable these segments of an individual genome to be controlled independently from the whole genome.

In a preferred embodiment of the invention, three fundamental system instructions or rules are employed. These are indicated in the table below:

(1) The more specific (i.e., the more granular) instruction should take precedence over the less specific;
(2) The more recent instruction should take precedence over the less recent; and
(3) In the absence of a specific permission to allow access, the default condition should be to deny access.

It is recognized that in some circumstances and for some sponsors, other foundational instructions could optionally be used. Notwithstanding, in a well-ordered system for carrying out the teachings of the invention, it is deemed preferable that the foregoing system rules be employed as creating the best basis for assuring privacy and enabling private access controls; and in turn, the best foundation for establishing and maintaining trust.

Thus, the ability for a data seeker to be permitted access to a single chromosome could be created by an instruction from a grantor to allow access to that one chromosome, 213, which in the absence of any other instruction would deny access to the remainder of the genome. Conversely, an instruction could be given to allow access to the whole genome 211, but deny access to a single chromosome, 213, and thereby application of the foregoing system rules would enable access to the data for the entire genome except for data within that said one chromosome. Persons of ordinary skill in the art will understand that through consistent application of the foregoing teaching, a grantor may be able to fulfill a wide variety of access control objectives, ranging from total concealment to full disclosure of the genomic information; and according to which changes can take place in an orderly manner over time.

The process of specifically identifying and imposing access controls on selected elements of electronic documents is described in Applicant's U.S. Pat. No. 8,904,554, which matured from U.S. patent application Ser. No. 13/075, 344 (System and method for selectively redacting information in electronic documents) (the '554 patent). Such teachings are described with respect to the control of bioinformatic information such as genomic data through the use of the illustrative case associated with FIG. 4 hereof, which employs "unique data element identifiers" that are associated with access control settings for such data elements and the privacy directive ontology described in connection with FIG. 5 hereof.

In the '554 patent, the teachings of which are incorporated herein by this reference, Applicant discloses:

" . . . a computer implemented system and method [] for imposing access controls on selective portions of electronic documents by defining data attributes as conditions for access to particular data in a document. . . . "

"In an illustrative embodiment of the invention an 'electronic document' may comprise all or part of a person's genome or other atomic or molecular structural information. A person using this embodiment may designate certain portions of his or her genomic information as private, other portions as public and certain portions as being authorized for viewing by designated individuals or under designated circumstances, for example. Such selective redaction of a person's genomic information may be appropriate when the information is associated with personal attributes or susceptibilities, which could be the basis of discrimination against the person."

"Although genomic information is referred to herein as an 'electronic document' it should be understood that such information may never be embodied in a hard copy and may typically be stored in a computer readable medium for interpreting or displaying by a computer device. Where such device may interpret or use genomic information or other electronic documents without requiring a display, the embodiments of the present invention may perform redaction by rendering redacted information inaccessible to such devices."

When used in conjunction with the teachings of the aforementioned '544 patent and Applicant's U.S. Pat. No. 8,909,669, which matured from U.S. patent application Ser. No. 13/075,313 (System and method for locating and retrieving private information on a network), herein referred to as the '669 patent, such information that is intended to be accessible may be more readily located and employed by properly authorized parties, and simultaneously excluded from discovery, access, use or inadvertent (or malicious) disclosure in other instances.

Applicant's '669 patent, which is incorporated herein by this reference, teaches a "system and method for controlling access to documents using access control parameters to reduce preliminary search engine hit lists prior to searching the preliminary search hit list for subsequent search terms in a query." Focusing only on the documents, or portions of such documents or data tables, that the searcher is permitted to access, reduces the use of processing resources, transmission bandwidth, and data storage requirements, and simultaneously enhances privacy protections. Given its sheer size and the sensitivity of the information it contains, this approach can be of particular utility for genomic information, where for example, access to an individual's entire genome may not be required in order to provide useful information for an intended purpose, coincidentally saving extensive processing and storage resources and simultaneously precluding any portion of that individual's remaining genomic information from being exposed to privacy risks by virtue of having been removed from the search index prior to the conduct of queries by a data seeker who is not authorized to access such information.

In one illustrative example, a researcher investigating the importance of certain variants occurring on Chromosome 3 in relation to autism may not require access to any information concerning other portions of an individual's genome. Thus, by selectively addressing her inquiry just to this data segment, the data to be processed is reduced by approximately 95%, and any privacy risks associated with that remaining data are simultaneously eliminated. An inquiry for another data seeker, who is for example interested in investigating certain mechanisms associated with cystic fibrosis that are known to be associated with the CTFR gene on Chromosome 7, could pursue his inquiry through access to a similarly small percentage of total resources and the corresponding assurance that privacy risks are materially less than in the case this required whole genome access. By virtue of reducing the dimensionality of the data shared, the formidable challenges of anonymization of the genome and the risk for re-identifiability can be materially reduced, particularly where specific regions of the genome known to introduce privacy risks (for example, access to Y chromosome data from which deducing a surname of the individual to whom the genomic sequence pertains has been shown to be possible) but that may be of no moment whatsoever to a data seeker's particular inquiry are entirely eliminated from being included in returned results.

FIG. 2(c) illustrates the level of whole chromosome access 215. As illustrated, rectangular box 216 corresponds to box 213 of FIG. 2(b); and in one preferred embodiment, would be accessible for more detailed segmentation in the event one or more of said chromosomes 212 were selected. Thus, in such illustrative case, the arms, regions, bands, and sub-bands comprising the chromosome (i.e., in this example, for Chromosome 3) are indicated by ideogram 217.

As the sequencing reads described with reference to FIG. 1(a) are assigned a position, such as relative to the reference genome, and identifying to which chromosome such read belongs and/or its offset from the beginning of that chromosome, the beginning and ending of each such chromosomal arm, region, band, and sub-band may be ascertained. Such identification of the individual arms, regions, bands, and sub-bands on the selected chromosome(s) results in the prospect for identifying one or more such segments of the chromosome, such as by clicking on the corresponding area of the ideogram to produce rectangular box 218(a), and an indication of the identity of such selection (i.e., in this example, for region 2, band 4 on the long (q) arm of Chromosome 3) by a link 218(b) thereto, or by designating the one or more desired areas by entering the name(s) in field 219. By practicing the principles of the invention described previously, such further segmentation of the selected chromosome enables inquiry by a data seeker respecting that one or more selected chromosome arm, region, band, or sub-band; or conversely permits inquiries of data for the entire chromosome (or optionally the entire genome) with the exception of data pertaining to such designated area(s).

Figure 2D:
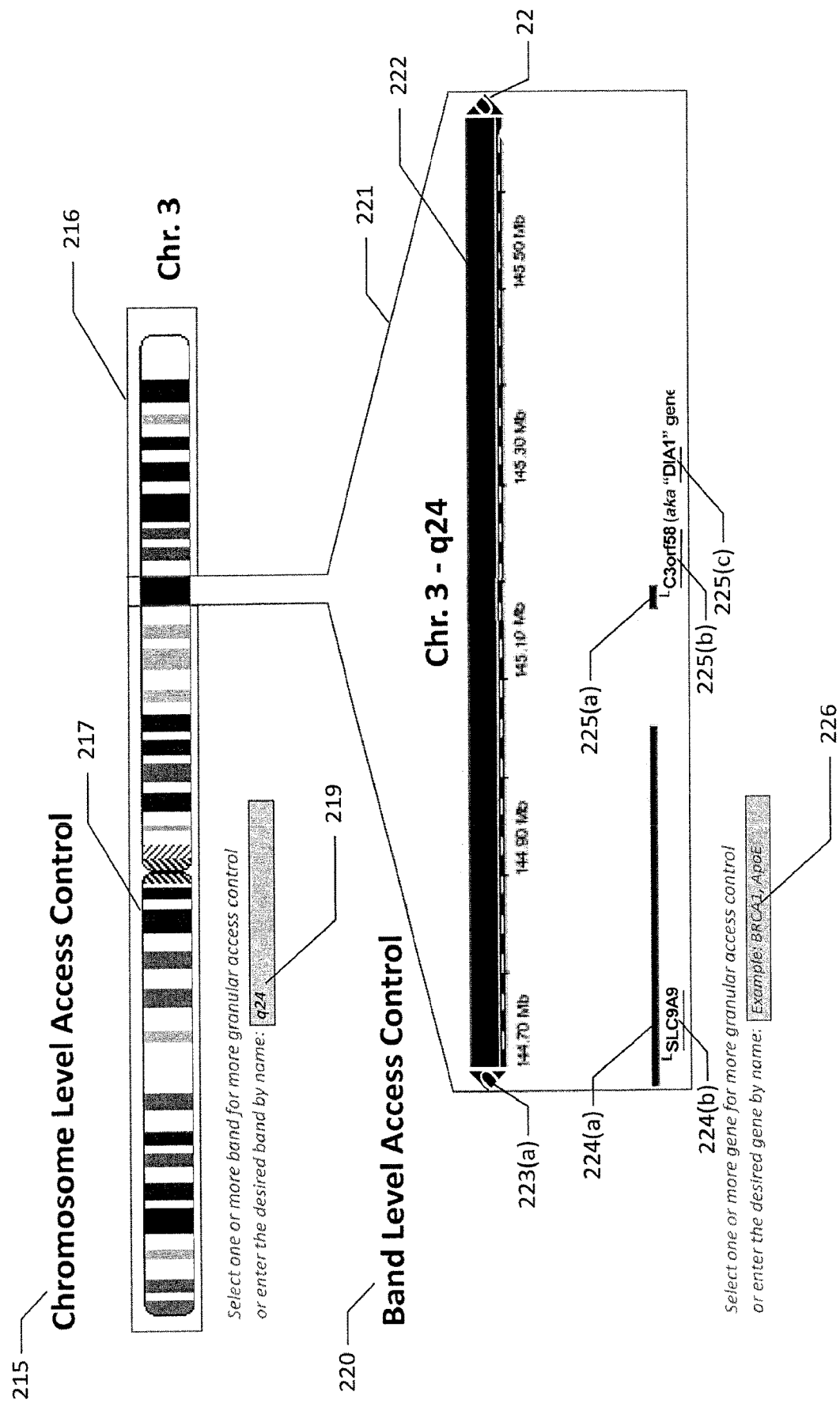
FIG. 2, consisting of subparts 2(a), 2(b), 2(c), 2(d) and 2(e), is a series of simplified illustrations showing the effect of segmenting the genome at various levels of granularity in accordance with the teachings of the invention, and illustrating the effect of such various levels of access controls.

FIG. 2(d) illustrates the level of extending such access controls to band access and control 220. As illustrated, shaded box 221 corresponds to rectangular box 218(a) of FIG. 2(c); and in one preferred embodiment, would be accessible for more detailed segmentation in the event one or more of such chromosome arms, regions, bands, or sub-bands were selected. Thus, in such illustrative case, the selected area (i.e., in this example, band 3q24) is indicated by line 222. As shown, to the extent the line representing the selected area is longer than the width of box 221, forward and back arrows 223(a) and 223(b) permit moving in the direction of said arrow and reveal immediately below the location where in a reference genome said genes are located. In the illustrative example shown in FIG. 2(d), two genes are identified. The size and location of such genes are indicated by line 224(a) and a corresponding link to the name of such gene 224(b); and line 225(a) and links to that gene's corresponding name, 225(b) and 225(c). Alternatively, reference to such genes can be achieved by entering the names of said one or more genes into field 226.

The beginning and end of each of such genes can be identified as the sequencing reads described with reference to FIG. 1(a) are mapped, aligned, de-duplicated, and variants are identified relative to the reference genome. Such segmentation of one or more individual genes, in combination with the teachings of this invention, enables inquires to be made exclusively with respect to such one or more gene (i.e., for example, the DIA1 gene 225(c), which is known to be associated with autism); or conversely to inquire of data for the entire banded region, the entire chromosome, or even the entire genome with the exception of data pertaining to such gene(s). As more particularly discussed with regard to FIGS. 3 and 4, it will be apparent that such granular controls would enable a clinician or researcher interested in autism, as a non-limiting example to inquire into data exclusively with respect to such DIA1 gene or with regard to a collection of genes associated with autism that includes such DIA1 gene; or alternatively, to enable any individual (and not just someone such as Dr. Watson respecting his ApoE gene) to selectively control access to his or her entire genome except for certain genes.

FIG. 2(e) illustrates both gene level access 227 and the level of base pair access and SNP control 228. As illustrated, shaded box 230 corresponds to the span of the selected gene 225(a) of FIG. 2(d); and in one preferred embodiment, would be accessible for more detailed segmentation in the event one or more of such genes were selected. Thus, in such illustrative case, the selected area (i.e., in this example, the DIA1 gene) is indicated by line 225(a), by the entry of such gene name in field 226, or entry in field 229 of a condition or syndrome name, pathway, or other term representing the involvement of a combination of factors for which such gene in commonly associated.

As shown, to the extent the length of the string of base pairs that comprise such gene 231 is longer than the width of box 230, forward and back arrows 232(a) and 232(b) permit moving the base pair string in the direction of said arrow and reveal the corresponding values in a reference genome together with the location of SNPs (Single Nucleotide Polymorphisms) or clusters of SNPs in which variants have been identified in, for example, the dbSNP database maintained by the National Center for Biotechnology Information at the National Library of Medicine.

Persons of ordinary skill in the art will appreciate that access to the molecular variation cataloged within dbSNP, dbGaP, and other databases including those being planned by the National Cancer Institute, aid basic research such as physical mapping, population genetics, and investigations into evolutionary relationships, as well as assist clinicians to quantify the amount of variation at a given site of interest. Application of the teachings of this invention will enable researchers, clinicians and even other individuals who are permitted in accordance with the privacy directives at the time they seek such information to more rapidly identify matches of individuals who have variations in common, which would be useful in more rapidly generating research hypotheses, establishing connections with other individuals who share common genetic traits, identifying potential members for research cohorts focusing on a particular variant and, supporting future precision medicine therapeutic initiatives.

The dbSNP database contains a range of molecular variation including SNPs, short deletion and insertion polymorphisms (indels/DIPs), microsatellite markers or short tandem repeats (STRs), multinucleotide polymorphisms (MNPs), heterozygous sequences, and named variants. In the illustrative example shown in FIG. 2(e), two of the approximately 1050 currently identified variants listed in the dbSNP database are shown that are located within the DIA1 gene. Rectangular boxes 233(a) and 234(a), and a link to their corresponding ID references 233(b) and 234(b), and respectfully, indicate the locations of such variants. Alternatively, the designation of such variants may occur by entering the reference IDs or position in field 235, or entering in field 236 the name of a condition or syndrome name, pathway, or other term representing the involvement of a combination of factors for which such SNP variants are commonly associated.

As more particularly discussed with regard to FIGS. 3 and 4, it will be apparent to persons of ordinary skill in the art that enabling granular access controls in accordance with the teachings of this invention will enable a data seeker who is a clinician or researcher interested in a particular variation on a selected gene (for example, the DIA1 gene that is associated with autism), to inquire into data exclusively with respect to that variant, while simultaneously assuring that such disclosures are being made in accordance with the applicable laws, institutional policies and the affected individual's preferences. Based upon these granular settings, and with the dynamic nature of the system and method, this could be done without needing (and without receiving) any information whatsoever about the remainder of the gene, the area of the chromosome where such gene is located, or any other information pertaining to the genome of the individual, and various permutations of such inquiry patterns. Alternatively, a data seeker could query a collection of SNPs suspected to have significance with regard to a condition or disorder, such as in the present example autism, without accessing any other information. And in yet another alternative example, such granular access could enable selectively controlling access to certain areas of potential variation where revealing information concerning the participant is not desired or permissible. And in yet one other preferred embodiment, as previously described, the use of homomorphic and/or other competing methods of encryption may enable the processing of such access and/or return of results determinations without revealing any information (at least in an unencrypted form) concerning the information as part of the functions performed by the private access bureau.

In a preferred embodiment such designations of areas of inquiry do not reveal any information about the individual genome to which such access controls pertain (i.e., they are not themselves "a viewer" for such genomic information) but rather they are used solely as a means by which to establish who and under what circumstances access is permitted, prohibited, or conditioned upon certain pre-conditions, and/or to submit a targeted inquiry into such portion of the genome. In this case, the controls could be employed to initiate an inquiry before any information is revealed about the individual's genome—for example, to only make available for analysis those segments of genomic information that are relevant to a specific condition or disorder, or a panel of disorders designated by a particular group or organization such as the American Society of Human Genetics (ASHG), The American College of Obstetricians and Gynecologists (ACOG), and others.

Such granular access controls will also be of value to data seekers such as clinicians and/or researchers who "create a 'standing order' that will automatically prompt an attempt to retrieve certain types of materials and information under pre-specified circumstances" as taught in Applicant's prior U.S. Pat. No. 7,028,049, entitled "Standing order database search system and method for internes an intranet application", which matured from U.S. application Ser. No. 09/025,275, filed on Feb. 18, 1998 (the '049 patent). In several non-limiting examples, employing such standing order inquiries for genomic information could enable practitioners to identify individuals with particular genomic characteristics of relevance to prescribing practices that would trigger meaningful alerts, and/or who might be of interest to a clinical trial for which active recruitment was at that time underway.

In an optional embodiment, users could be provided an opportunity within a genomic sequencing results viewer such as a Map Viewer or Chromosome Browser to establish specific privacy controls for a data segment where a variant is revealed (for example, by having the option to click on an icon to enable such enhanced feature). In this optional case, either prospectively before any results are revealed or upon becoming aware that a variant is present, the participant could make the decision whether to treat access to that segment with a different set of access rights than other portions of the information. This could, for example, enable someone with concerns about a topical area such as having a heightened risk of pathogenic variants regarding conditions for which there are no known treatments to limit return of results, or upon becoming aware of a genetic variation they deem inappropriate to being disclosed to others, to expressly limit such result from being accessible to all or particular data seekers. Persons of ordinary skill in the art will readily see the applicability of such flexibility for providing individuals with the options to avoid being informed of matters for which there are no known interventions, and/or enable triggering of such information at a future point in time when interventions (or perhaps clinical trials designed to investigate potential interventions) do become known and/or germane in the opinion of the affected individual or an oversight body for such sorts of matters.

Similarly, in several other non-limiting examples, the individual could elect to make the region with the variant more accessible to another clinician in pursuit of a second opinion, and/or to researchers working on the particular condition or disorder for which such variant is associated in hopes of advancing future treatment modalities by the time such predisposition might be pertinent to the participant in later life. In another non-limiting example, the participant could indicate a willingness to connect with others having a similar variant. As the foregoing examples illustrate, the functionality would be of benefit to addressing the concerns and interests of a participant who favors enabling greater-than-otherwise permissible disclosures, just as much as another who wishes to selectively restrict such access rights; and to the broad population of individuals whom research has shown fall between these two extremes.

The table shown below summarizes the foregoing levels of segmentation that could be provided in one preferred embodiment using data from the most recent build (v142, October 2014) of the dbSNP database. As shown therein, with regard to the DIA1 gene and Chromosome 3 (which have heretofore been used as an example), a total of slightly over 1,050 potential levels of access control are provided at the gene level; and approximately 8.44 million levels account for all currently referenced variants, including those with both known and unknown significance. The following table also indicates that for the entire genome, approximately 26,000 potential levels of access control are provided to the gene level; and approximately 122.8 million if wishing to take into account all presently referenced variants. Based on the NCBI's Variation Viewer, accessible at http://www.ncbi.ni,.nih.gov/variation/, the following potential levels of segmentation are available:

|  | Only the DIA1 gene | Only the q24 band | Chr. 3 Only | Entire Genome |
|---|---|---|---|---|
| Whole genome access | — | — | — | 1 |
| Chromosome level | — | — | 1 | 25 |
| Regions | — | — | 5 | 89 |
| Bands | — | 1 | 21 | ~300 |
| Sub-bands | — | — | 56 | ~580 |
| Genes | 1 | 486 | 1,900 | ~25,000 |
| SNP variants | 1,050 | 242,228 | 8,442,924 | 122,788,469 |

The particular needs and interests of the practitioner will dictate the optimal levels of segmentation for a sponsor to employ in carrying out the principles of the invention. For example, rather than enabling individual access and control over all SNPs or SNP clusters with at least one reported variant in dbSNP, other approaches may reduce the overall numbers of segments materially and still be highly useful. Such approaches could focus only on the SNPs for which there exists reliable evidence of a pathogenic relationship, inclusion in references such as the ClinVar database maintained by the National Center for Biotechnology Information of reports of the relationships among human variations and phenotypes (http://www.ncbi.nlm.nih.gov/clinvar/) and/or (OMIM (Online Mendelian Inheritance in Man; http://omom.org/) database, or whether the number of reported variants exceeds a predetermined percentage threshold so as to focus on the more prominent variants whether or not a pathogenic relationship is yet reported in the literature or such public databases.

Region-based annotations may also be of use pertaining to the annotation of variants based on specific genomic elements other than genes, for example, conserved genomic regions, predicted transcription factor binding sites, predicted microRNA target sites, and predicted stable RNA secondary structures. Persons of ordinary skill in the art recognize that being able to resolve to such regions is important for whole-genome sequencing data, inasmuch as a large number of variants occur outside of protein coding regions, and their functional effects cannot be assessed simply by gene-based access controls. Possessing the capacity for affording segmented access controls over such regions is likely to be of value to prioritizing genetic variants from diverse genomes, and could help expedite scientific discoveries from the massive amounts of data produced from NGS platforms.

In addition to the specific structures, it is deemed preferable to identify collections of two or more such areas of the WGS, which alone or in combination, appear to be associated with a particular disease and disorder, and to treat such collection as a single segment. The designation of such panels by specific phenotypic characteristics or diagnosed conditions or disease could help to empower participants, clinicians, researchers and others having a legitimate reason: (i) to help facilitate and expedite access to such information of interest; (ii) to assert greater control over and/or more effectively limit access to such segments; or (iii) both (i.e., by designating greater access by specific persons or for certain purposes, and little of no access by others). Such selection should preferably balance the parties' respective goals and self-interests, within the bounds of legality, ethical principles, and permitted access, and should be regularly updated to account for the latest information based on research as well as clinical experience.

Such updates could be made in the software or cloud-based implementation illustrated in 106(a), and in the instance involving an integrated circuit as shown in 106(b), could preferably employ the attributes of a field programmable gate array (FPGA) wherein the chip can be reconfigured to account for such updates. Moreover, in a well-ordered system employing the teachings of Applicant's prior '544 patent, such collections do not need to be known at the time that the initial segmentation is implemented, and may be applied at a later date based on creating collections of elements at the level of the private access bureau or search facility that take into account the latest genomic analyses and correlations, thereby extending the prospective utility of genomic data collected years earlier.

Turning next to FIG. 3, a block flow diagram is provided to illustrate the workflow through which the foregoing data segmentation, assignment of related metadata, indexing, encryption, and association with privacy directives can be achieved.

As illustrated therein, such workflow begins at oval 301, which represents the beginning point within the process of aligning, mapping, de-duplicating, and variant calling that is best suited for the particular segment. This point may differ depending on the size and nature of the segment involved, the variability present in the sequencing reads, and based on the type of technology being employed to execute such disclosed processes. Moreover, although illustrated in a sequential order, it will be understood that the particular order for carrying out the process addressed by FIG. 3 may differ based on the segments that will be included, the type of technology that is employed, and other factors that will contribute to making the conduct of the process take place in the manner that is most effective and efficient (i.e., with the least amount of additional time and consuming the least amount of incremental computing resources, while still producing the indicated enhancement to both accessibility and protection through practice of the invention). As indicated by recursive loop 302, regardless of the approach taken, the process illustrated in FIG. 3 will preferably continue until all of the segments that are deemed desirable to be addressed have been subjected to such workflow steps.

Rectangular box 303, entitled "Define the beginning and ending point of the selected segment," illustrates the step of identifying the particular portion of the genomic sequence associated with such selected segment. Rectangular box 304, entitled "Extract (or derive) and save relevant metadata for said segment," involves summarizing, extracting, or calculating with respect to such selected segment various metadata that provide valuable information concerning the raw data but without exposing to the inquirer the actual data to which such metadata pertains. By way of several non-limiting examples, such metadata for the DIA1 gene may consist of a list of any SNPs located within said gene of the individual in which there is observed a variant; and the metadata for chromosome 3 may consist of a list of any genes in which there is observed a variant. Rectangular box 305, entitled "Extract (or derive) and save relevant meta-metadata for said segment," involves summarizing, extracting or calculating with respect to such selected segment meta-metadata (and in some instances even higher levels of abstraction) as more particularly described in relation to FIG. 4 and FIG. 5.

Thus, by way of foregoing non-limiting examples, where such metadata for the DIA1 gene reveals any SNP variants identified during variant calling process 110, meta-metadata element 305 could merely reveal whether or not there are present one or more variants on said DIA1 gene as a binary expression [Y|N], or could indicate the raw number of said variants that are present, or the weighted probability of there being a variant present based on the level of sampling employed, but in each illustrative case without providing any information concerning the particular variant(s). Similarly, where such metadata for Chromosome 3 reveals any genetic variants during the variant calling process 110, meta-metadata element 305 could merely reveal as a binary expression whether or not there are present one or more genes on said chromosome which evidence a variant, or could indicate the number of genes on the chromosome in which a variant is present, or the weighted probability of there being a variant, etcetera, but without indicating which of said genes.

Thus, in such illustrative instances, practicing the principles of this invention would result in a number of advantages. A data seeker who was a clinician seeking merely to ascertain whether a patient in her care had a variant on said DIA1 gene could instantly attain this answer by inquiring of said meta-metadata at the level of single gene access control; and only in the case of an affirmative response need to proceed to the meta-data or more detailed data levels of access, thereby avoiding the risk of incidental findings that are present in the current state of art.

A similar step could in the future be conducted when prescribing any drug for which there is at the time of administration a known role of genetics in drug response. This would open the prospect for these sorts of inquiries to be initiated asynchronously to the time the original test was conducted, thereby opening the prospect for added value being derived from a genomic test conducted for a different purpose, such as a part of NIPT or newborn screening, clinical germline exome or genome sequencing that identify whether any of the 56 genes implicated in various known or expected pathogenic mutations recommended by the American College of Medical Genetics (i.e., the "ACMG-56 variants") are present, a genomic test originally undertaken to diagnose a different presumed indication, as a part of a program such as Illumina's Understanding Your Genome® (UYG) program, or as part of population sequencing, all of which tests are likely to become much more common with the continuing decline in cost of WGS.

In the case of a data seeker who is a researcher conducting an observational study looking for correlations of variations in DIA1 with particular phenotypic characteristics, the information could be attained across thousands or hundreds of thousands of WGS results without any risk to privacy of an individual. Should another researcher seek information concerning a particular SNPs located on said DIA1 gene, said inquiry could be conducted with respect first to the meta-metadata 305 to narrow the inquiry to those exhibiting some variant, and then by inquiring of metadata 304 with respect to merely the subset to which this inquiry was pertinent. Because the invention enables access in this manner without the possibility for re-identification, the ability to inquire of all of the genomes in an entire network, population, or subset thereof, becomes far more feasible than under the current art.

Rectangular box 306, entitled "Derive and assign a GUID for said data, meta- and meta-metadata," illustrates the step of assigning a globally unique identifier to said data, meta-data and meta-metadata. And box 307, entitled "Associate privacy directives with said data, meta- and meta-metadata," teaches associating said assigned GUIDs to the location where the then applicable (i.e., as of the time an inquiry is made of said location) privacy directives pertaining to the individual circumstance may be ascertained, preferably through a web services bureau, thereby enabling the ability to employ the teachings of Applicant's earlier inventions, wherein privacy preferences are associated with different levels of access control, such as only permitting one or more specifically designated data seekers, or groups of data seekers such deeper access rights. By virtue of being associated in this manner in a preferred embodiment of the invention, access decisions respecting such granular data, metadata and meta-metadata need not be static determination, but to the contrary is able to change (and/or be changed) over time should applicable institutional policies, governing jurisdictional law, and/or individual privacy preferences concerning the right to access such information change.

As disclosed in Applicant's '544 patent, it is deemed preferable that in addition to having the option to "Allow" such protected data elements to be shared, and to "Prohibit" the data from being disclosed, a useful third option should also be available (referred to as "Ask Grantor") in the event access is requested by a data seeker, or when a data holder otherwise initiates steps to share the protected data with another party.

In this third option, the grantor is able to express a preference to be notified and permitted to "allow" or "deny" such proposed access or sharing on a case-by-case basis. This provides an important function for the grantor (for example, in the present case, the individual whose genome sequence is revealed in said protected data, the institution holding that sequence or metadata associated with the contents of such sequence, or any other party having a right to assert who may or may not disclose the information to a data seeker).

Providing this option is important because it enables, in effect, a "Maybe" status that protects the information from disclosure until more information is disclosed to the grantor about the data seeker and/or the nature of their interest, for example pertaining to their proposed use, their agreement to remunerate the data holder for such access, and the like. In many cases, the basis for making a decision is unknown (and potentially even unknowable) at the time the bioinformatic information is produced. Thus, even if privacy directives are created at that time, limiting the options regarding how that data will be used and who will be permitted access to it merely to "allow" or "deny" (which depending on context, may be through "Opt-in"/"Opt-out" mechanisms of being included in the network) requires a level of prescience that a number of privacy advocates, medical ethicists, and IRBs deem unreasonable or confiscatory and thereby seek to control by limiting access to just what can be foreseen at the time original acquisition is undertaken. In such instances, the "Ask Grantor" selection enables deferring a decision about data sharing until such time when more information is known about the proposed access, and therefor when a more reasoned decision can indeed be made—one that is much more in accord with Fair Information Practices and high ethical standards—all the while without revealing ones identity to the data seeker (unless this too is deemed to be permissible at the time).

Thus by employing these principles, should any data seekers wish to identify a research cohort for a clinical trial or in the future, to be able to readily locate and notify persons of the applicability of a new treatment protocol designed for individuals with a specific genetic variation, the information concerning how many of that population, for example, are located within 25 miles of a particular study site or clinical practice who exhibit such variant could be readily educed without ever revealing any raw genomic data, any information respecting other portions of the genome, or having any access to contact information for said persons. And at the same time, to the extent permission to do so was either pre-authorized or granted dynamically by such individuals to their contact details, this could facilitate direct contact taking place between the professional and said individual. These same attributes are likely to produce useful information for automated decision support systems used in rendering care and prescribing medications.

From an efficiency perspective, the foregoing benefits could be derived without ever needing to survey the entire genome record inasmuch as the only data required to be surveyed would be (a) those participants whose metadata or meta-metadata was affirmative respecting the presence of such data; and (b) those whose privacy permissions enabled that data seeker to access such information. Thus, it will be apparent to one of ordinary skill that a data seeker who additionally was granted private access rights to phenotypic information regarding the affected individual and/or to the individual subject's contact information, could go much deeper with far more efficiency and far greater protections for all individuals within the system than under the current state of art. Such granular access controls would also enable only those data seekers with an inquiry having relevance to the individual to access her information, and would simultaneously minimize the risk of inadvertent or malicious use of such data by anyone else querying the database.

Given the foregoing protections, the opportunity is then presented to open at least such metadata into a searchable index, including in a preferred embodiment a public or quasi-public search index. This is illustrated by rectangular box 308, entitled "Submit such data, metadata and/or meta-metadata to a search index". This would enable more individuals to locate the record holder of such information, opening the door to more collaborations and greater data sharing, while simultaneously improving the privacy of such information.

Rectangular box 309, entitled "Separately encrypt such data, meta- and meta-metadata elements", illustrates that in a preferred embodiment encryption is used to enhance security and privacy protections while data is in transit and while at rest. Additionally, some systems such as Elastic Search permit searching an encrypted index which may also be employed in one preferred embodiment, such that decryption is only enabled for a data seeker to whom such access rights have been expressly granted, either by prior authorization or by using the "Ask Grantor" service, described previously.

In a preferred embodiment, the whole genome 211 would be encrypted using an appropriate encryption technique. In one preferred embodiment, data at rest is encrypted in accordance with standards established by the National Institute of Standards and Technology (NIST), and using the Advanced Encryption Standard (AES) for encryption algorithms known to those persons of ordinary skill in the art of data security. Rectangular box 310, entitled "Compress such data, meta- and meta-metadata elements," illustrates that in a well-ordered system, such information may be compressed at various points in order to reduce system resources. For example, files such as the original FASTQ, BAM or SAM file with are less likely to be frequently accessed may be segmented and subjected to access controls employing the VCF metadata, but compressed, encrypted, and stored in a less accessible storage site such as Amazon Web Services' Glacier storage.

Various strategies are possible with respect to both the data storage location and decryption key management, although it is deemed preferable that data holders retain the data locally or under their control in a public cloud, as well as the key required to decrypt it. As described in the '544 patent, it is preferable that the data holder confirm though a web services call or API to the private access bureau the right (or absence of such right) to employ said decryption key and thereby make such data accessible to a data seeker. And in one preferred embodiment, the data holder would have the right to "break the glass"—meaning to ignore the instruction to "Deny" or alternatively to first seek permission through "Ask Grantor" and to proceed to decrypt and share the information with a data seeker even where express permission is not yet confirmed. In such instance (as is the case in compliant circumstances), the data holder's decision will be recorded in the system's audit log together with a timestamp for when such sharing took place, under whose authority this transpired, and for what reason; and an opportunity will be accorded to the grantor to assert that it such decision was improper, and therefore to pursue appropriate restitution.

Diamond shape 311, entitled "Was that the final segment to be processed?" assures that the foregoing process steps are undertaken until all of the bioinformatic segments that are intended to be identified have been processed, or alternatively until such processing is terminated for an orderly reason. Hence, when the response thereto is "No," recursive loop 302 returns to beginning step 301 for the next segment, and upon such response being "Yes", orderly ends the process, as designated by oval 312. Thus, it will be apparent to persons of ordinary skill in the art that with the advancement of knowledge, Turning now to FIG. 4, a drawing is provided to illustrate the relationship between the data pertaining to an individual segment, metadata pertaining to such data segment; and meta-metadata pertaining to said metadata, the use of encryption protection, and the assignment of globally unique identifiers for such data and metadata elements.

Circle 401, entitled "Data content of selected segment," represents for each segment of the genome the actual data resulting from the data analysis pipeline described in relation to FIGS. 1(a) and 1(b), and reflecting the actual results of the sequencing process. Rectangular box 402(a) illustrates an assigned UUID (Universally Unique Identifier), GUID, Handle, DOI® (Digital Object Identifier), or the like (collectively or individually referred to herein as a "GUID") for such data content 401. As described with reference to FIG. 2, examples of such selected segment content in one preferred embodiment include the whole genome; each of the chromosomes comprising such genome; each of the arms, regions, bands and sub-bands comprising each such chromosome; each of the genes located in such defined areas; etcetera.

Persons of ordinary skill in the art will recognize that a GUID shown in rectangular box 402(a) is illustrative of a unique identifier for a digital object with a machine and platform independent structure that allows the object and other metadata about the digital object to be identified, accessed and protected. There are several systems for generating and resolving such persistent identifiers, which can be used to enable a distributed computer system to store identifiers and resolve them into the information necessary to locate, access, contact, authenticate, or otherwise make use of the resources to which they pertain. Shaded band 403 indicates that the data to which such GUID 402(a) pertains is optionally compressed (if compression is merited by the size of the data) and encrypted, and thereby protected from disclosure except in accordance with the then current instantiation of one or more relevant privacy directives that are located in the PPMS for said uniquely identified data content.

The lightly colored band 404 entitled "Its metadata" refers to the metadata that is derived or assigned and that is associated with data content 401. While such metadata may contain any number of useful attributes, in one preferred embodiment it minimally contains the identity of the data content about which it pertains (i.e., the segment of the genome to which that data content 401 pertains); the GUID for that data content; and any variants that are known to exist in said content relative to a reference genome. Such metadata may also nest one or more other GUIDs associated with such things as health profile data for the individual to whom such data pertains, and the name and contact details for the individual, which data may or may not be accessible to the data seeker. Rectangular box 405(a) is illustrative of the GUID for such metadata 404; and shaded band 406 illustrates that such metadata is also optionally compressed, encrypted and subjected to access or protection based on the then current instantiation of one or more relevant privacy directives that are located in the PPMS for said uniquely identified [metadata] content.

Lightly colored band 407 entitled "Its meta-metadata" refers to the metadata that is derived or assigned from metadata content 404. While such meta-metadata may contain any number of useful attributes, in one preferred embodiment it minimally contains the identity of the data content about which it pertains (i.e., the segment of the genome to which that metadata content 404 pertains); the GUID for that metadata content; and a binary expression [Y|N] to indicate whether any variants are known to exist in said content relative to a reference genome. As with the metadata, such meta-metadata may also nest one or more other GUIDs associated with other attributes such as the health profile, and general demographic information regarding of the individual and/or what sorts of gatekeepers are available to obtain more detailed levels of access if desired, which data may or may not be accessible to the data seeker. Rectangular box 408(a) is illustrative of the GUID for such meta-metadata 407; and shaded band 409 illustrates that such meta-metadata is also optionally compressed, encrypted and subjected to access or being precluded from access based on the then current instantiation of one or more relevant privacy directives that are located in the PPMS for said uniquely identified [meta-metadata] content.

Dotted rectangles 410, 411 and 412 indicate types of access that may be employed based on the foregoing approach. Depending on the nature of the inquiry and the rights accessible to the data seeker, the data associated with the GUIDs shown therein may pertain to one individual, or to anyone in the database. Rectangle 410, which contains meta-metadata for one or more data elements including 408(a) and similar meta-metadata for 408(b)-408(n), illustrates that without gaining access to actual variant data—much less to actual genomic data—a data seeker with minimal access rights may inquire of, and meaningfully analyze, the meta-metadata to ascertain (for example) the incidence level of whether variants are present in a particular segment of the genome among a population containing "N" records and, depending on the type of meta-metadata associated therewith for health related issues, may be able to estimate whether there appear to be any health issues that are common to the mere fact that some variant being present.

As described previously, this has a number of benefits, for both avoiding wasted resources, ensuring privacy, and identifying the subset of the data for which more revealing access rights may be desired. Dotted rectangle 411, which contains metadata for one or more data elements including 405(a) and similar meta-data for 405(b)-405(n), illustrates that although certain specifics concerning the variants that are present within different segments of genomic data may be accessible for, among other things, analytical and match-making purposes, such uses can still be achieved without revealing actual genomic data or identity. Even for a data seeker with full access rights, such abstractions may be beneficial to reducing incidental findings, triggering automated decision support system algorithms, and further narrowing the data that a data seeker requiring individual person level data must receive to just those individuals who are pertinent to the nature of that data seeker's inquiry. Particularly when used in combination with the "Ask Grantor" functionality enabling dynamic consent, as disclosed in Applicant's '344 and '544 patents, this enables individuals who are wary of excessive disclosure of their genomic information absent understanding the particular nature of the proposed disclosure or contact to be assured that the data seeker is focused on something specific to their genomic characteristics, and therefor much more likely to finding personal value for themselves or their children.

Dotted rectangle 412, which contains actual data content for specific segments of the genome including 402(a) and similar content level access for 402(b)-402(n), provides the benefits that have already been described for data segmentation. Thus, in one non-limiting example, a researcher interested in conducting detailed research on the DIA1 gene, could request access to just this segment across an entire population (with or without access to health related data), and without having access to any of the other genome information or the identity of any individual. Persons of ordinary skill in the art will appreciate that a number of useful combinations and permutations of the features and functions of the disclosed system and method are available to advance the simultaneous goals of maximizing accessibility to meaningful information with maximizing privacy.

As knowledge is advanced, the architecture lends itself to exploring variants and combinations of variants associated with particular health issues or predisposition to issues. As the cost of sequencing declines, it becomes increasingly possible to sequence large databases of collections such as dried bloodspot samples from the nation's newborn screening over several decades, and to provide individuals to whom such samples pertain to control the accessibility of results and to supply health profile information that can jumpstart the personalized medicine initiative. Similarly, using the high processing speed that is possible with the integrated circuit chip 106(b), it may be feasible to re-analyze large numbers of existing exome and genome sequences, and applying the principles of this invention to make this already assembled data useful to advancing the precision medicine initiative, and establish a baseline against which future sequence information can be analyzed. Given the privacy protective nature of the approach, this may be able to be pursued with IRB and ethics board approval using existing consent language that promises information will remain anonymous whereas it is known that whole genome sequencing in the absence of such protections cannot. Further, the use of the systems and methods describe enable any individual to whom such information pertains a path to reclaim and assert dynamic consent rights to limit or further extend such accessibility.

As greater insights are attained, this knowledge can be used to target the combinations of genomic segments that are subjected to inquiry—for example various panels focusing on the objective of specific diagnostic purposes (e.g., diagnosing a disease or potential predisposition thereto; clinical interpretation (e.g., looking for markers that represent a disease variant); or isolating whether an individual should be included or excluded as a prospect for various clinical trials or specific treatment approaches, and other such purposes). And correspondingly, such knowledge may be used to mask from accessibility the segments associated with a particular disease state, potential or genetic malformation to protect the privacy of the individual or to avoid disclosing information that is not desired at that time.

Persons of ordinary skill in the art will understand the importance in developing such metadata and meta-metadata expressions, that parties practicing the invention employ, where possible, applicable standards for genomic data, including with respect to platform information, controlled vocabulary, normalization algorithms, data quality standards, and metadata standards. A number of important initiatives are underway to develop and promote such standards, including the Genomic Standards Consortium, http://gensc.org/; the Global Alliance for Genomics and Health (GA4GH), http://genomicsandhealth.org/; and the NIH Big Data to Knowledge focus on community-based data and metadata standards, http://bd2k.nih.gov/about_bd2k.html#areas.

Figure 5A:
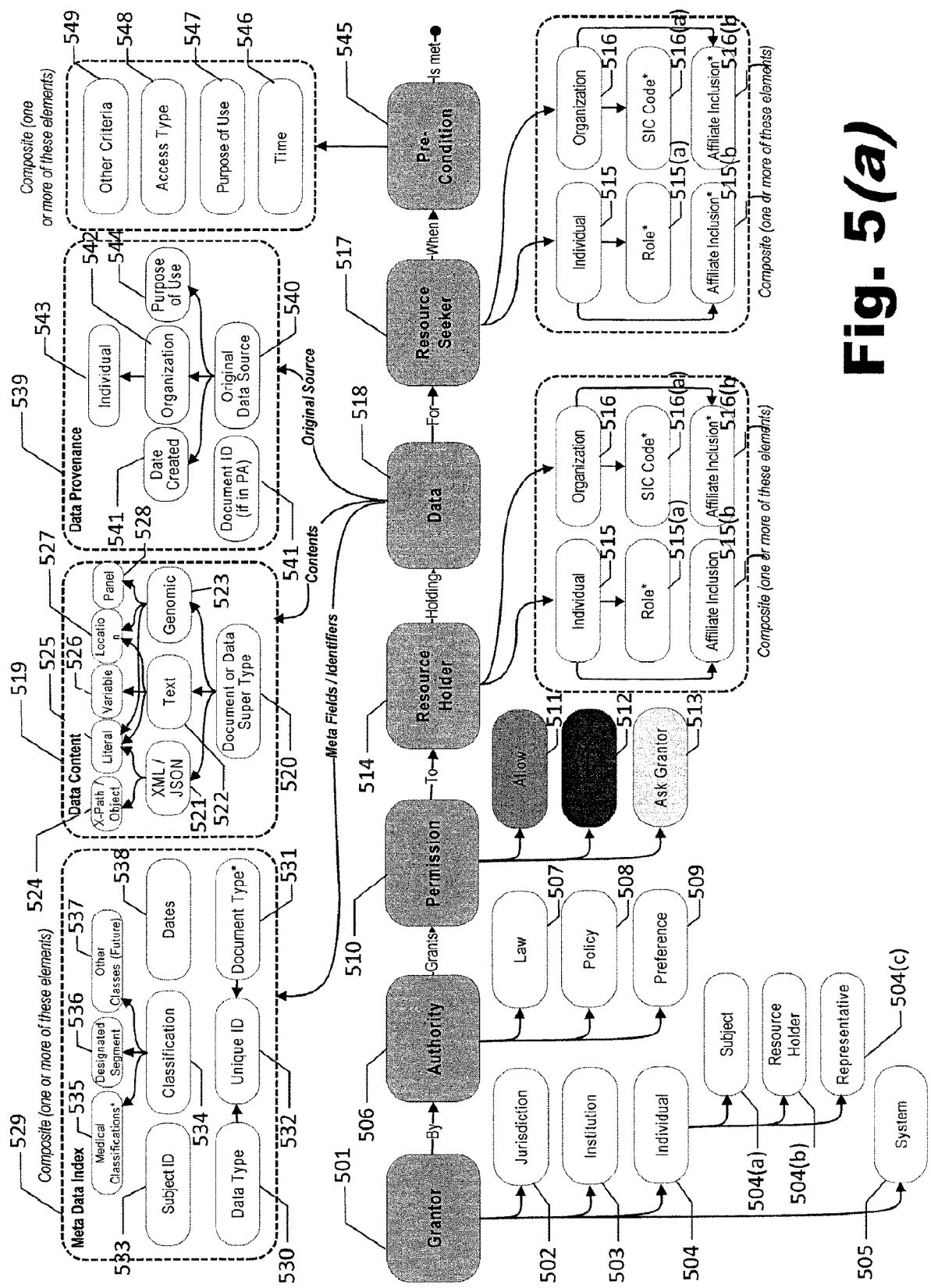
FIG. 5, consisting of subparts 5(a)-5(d), is a series of drawings showing an ontology for expressing privacy directives associated with such data and various levels of metadata respecting the granular segments of bioinformatic data in accordance with the teachings of the invention, and several examples illustrating its use.
Figure 5B:
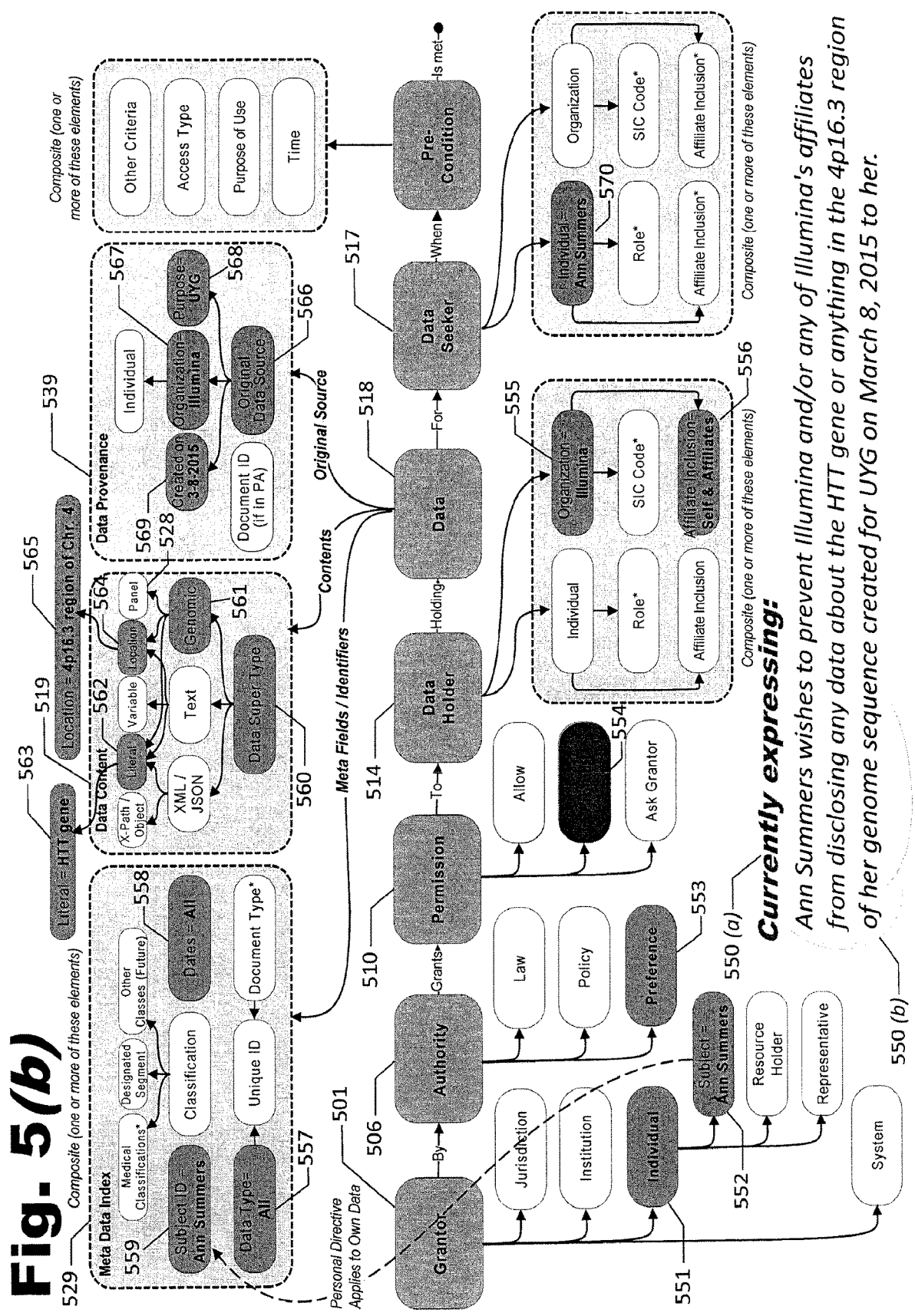

Turning next to FIG. 5(a), an illustrative ontological schema is presented for use in expressing privacy directives associated with such segmented bioinformatic data and the various levels of metadata described herein. Such schema amplifies on Applicant's prior '985 application, which teaches the following illustrative ontological expression for communicating privacy preferences (such terms being defined therein and incorporated herein by this reference):

<Grantor> by <authority> sets <designated action> affecting <record holder> holding <protected data> for <record seeker> when <pre-condition> is met FIG. 5(a) amplifies on such terms, as previously defined by Applicant, and extends certain aspects of said ontology to address genomic information and/or specifically identified segments thereof, as taught with respect to FIGS. 2, 3 and 4 hereof. The subparts of shaded rectangle 501, which is entitled "Grantor", illustrate the categories of grantors in a preferred embodiment. As shown, these include jurisdiction 502, including any level from local to international body whose laws or statutes govern data sharing and/or access; institution 503, which includes any entity whose policies address such matters; individual 504, which includes individuals capable of establishing preferences for data sharing and/or access by virtue of being the subject of the data 504(a), themselves being the resource holder 504(b), or a representative 504(c) for said subject of the data or individual resource holder; and system 505, whose rules affect data sharing practices.

Shaded box 506, which is entitled "Authority," illustrates the legal right or power invoked by the grantor in asserting a privacy-related directive, and may assist in determining the priority of said directive should there be multiple conflicting directives to consider. As shown, these include laws and statutory provisions 507 with respect to jurisdictions; policies 508 with regard to institutions; preferences 509 with respect to individuals; and processing rules (although not illustrated) for the system. Shaded box 510, entitled "Permission," illustrates the delegated action that a privacy directive (i.e., a law, policy, preference or rule) applies to the protected data or data element. As described throughout this application and in Applicant's prior disclosures, three such actions are provided in a preferred embodiment of the invention. The first of these "Allows" the data to be shared 511, and depending on context, may be used interchangeably with "Permit" and "Accept." The second of these "Prohibits" the data from being shared 512, and depending on context is interchangeable with "Prevent," "Decline" and "Deny". And the third is to "Ask Grantor" 513, in which event it is requested that the record holder ask the grantor, which depending on context may also appear as "Ask Me," "Unclear" or "Snooze."

Shaded box 514, which is entitled "Resource holder", corresponds to the record holder; and as the name implies is the holder of the protected data to which the directive applies. As illustrated, the ontology defines resource holders as individuals 515; organizations 516; groups of individuals and/or organizations; roles fulfilled by such individuals 515(a), line of business or SIC code in which such organizations perform 516(a); affiliations within which such individuals and/or organizations are identified 515(b) and 516(b), respectively; and/or any combinations of these elements. Shaded box 517, which is entitled "Resource seeker", relates to the record seeker identified in Applicant's '985 application, and as the name implies is the individual or organization requesting the data (or to which the data holder proposes to share it). As shown, the ontology uses the same constrained elements to define data seekers as for data holders.

Shaded box 518, which is entitled "Data" refers to the protected data (at whatever level of granularity is specified) held by the data holder 514 and sought by the data seeker 517. In a preferred embodiment, said protected data includes three elements, respectively focusing on the content 519 of the protected data; metadata 520 that describe it; and its provenance (i.e., the data's origin) 521.

The most direct means for identifying the data 518 to be addressed by a privacy directive is based on its actual content 519, which in one embodiment can be resolved based on the applicable schema for the document or data super-type 520 (e.g., XML, Text, PDF, Image, BAM, SAM, VCF, etc.) in which data 518 occurs. In FIG. 5(a), we illustrate how this is accomplished based on several widely used document and data super-types employed for bioinformatic data, including XML/JSON 521, Text 522, and Genomic 523. XML (Extensible Markup Language) is the W3C standard defining a set of rules for encoding documents in a format that is both human-readable and machine-readable, and may be either stated in X-path (XML Path Language), or the literal element name. JSON (JavaScript Object Notation) is a similar syntax for storing and exchanging data that is considered by many to be an easier-to-use alternative to XML; and that like XML, uses text that is both human-readable and can be read and used as a data format by any programming language, and may be either stated as an Object, or the literal element name. Accordingly use of XML/JSON 521, correspondingly resolve to X-Path/Object 524, depending on the syntax, or in either case the literal content 525. These schemas are illustrative only and do not preclude use of others.

Another approach to identifying such data content 519 is based on text 522, which as illustrated in FIG. 5(a) includes ascribing such content by its literal content 525, its use as a variable 526, or by the location 527 where such text is situated.

The third non-limiting example of a useful schema is based on genomic data super-type 523, which can preferably resolve unambiguously to the granular segments of bioinformatic data of a genome. Various non-limiting illustrative examples of such segmentation that may be useful in practicing the principles of the disclosed system, method and apparatus are described with regard to FIG. 2, such segments preferably being articulated through one of the more commonly-employed semantic systems for expressing and annotating genomic data.

Illustrative examples of how information from such semantic systems are employed within one optional embodiment include describing the data based on that structure's location 527, its literal name 525, or a panel 528 within which such genomic data segment is contained. Such "panels" may include, for example, collections of granular segments of bioinformatic data such as: {variants} of {known significance} to {condition} {name}; {arrangements} of {suspected relevance} to {phenotype} {characteristic}; {combinations} of {possible relevance} to {the effectiveness} of {drug compound}; and the like. In a preferred embodiment, such panels may be useful in establishing various meta-metadata expressions as more particularly described with regard to FIG. 4 hereof.

In one optional embodiment, said panels are defined through reference to a "current panel descriptor" that can be updated as information concerning the relevance of various genomic elements is ascertained over time with regard to the topic of said panel. In such optional embodiment, searching for a panel would refer first to the most up-to-date enumeration of the elements that should be included therein, and then these elements—identified, for example, by their literal name 525 or location 527—would be returned to said panel-based query. It will be apparent to those of ordinary skill in the art that the advantage of employing this approach is that the panel definition at the time the genome was sequenced may not be nearly as maturely articulated as a decade later when the same inquiry was conducted, and yet if the newer panel descriptor were to be applied to inquire of such panel, then the individual elements that comprise such query results would be in accord with the latest scientific knowledge rather than being out-of-date were the panel to be a static object.

Another illustrative approach that may be useful in identifying data 518 to be addressed in a privacy directive is based on various meta fields and/or identifiers 529 that may be included in a meta data index. Such meta fields 529 describe the data using a "label-like" approach, e.g. the label on the outside of a sealed envelope; whereas the contents approach 519 is based on the data content that is enclosed therein. This approach is particularly useful for private information because, in a well-ordered system, it permits data 518 to be subjected to privacy directives without disclosing the data content 519 to anyone other than an intended recipient. As shown, various illustrative forms of meta data fields include data type 530, document type 531, and unique ID 532.

Persons of ordinary skill in the art of healthcare information systems will recognize that a number of standards and specifications exist for such elements, some of the more widely embraced being by HL7, ISO and CDISC, for defining the kind of data that can be included in a field and/or representing its abstract semantics using standard controlled language in human-readable and/or machine readable form. The topic of globally unique IDs has already been described and is also widely know to those of ordinary skill in the art without undue experimentation, as is the process of expressing the content of such standards based meta data as an unique ID that is accessible given proper access privileges.

The subject of such data may also be represented by a unique ID 533, and in one optional embodiment such ID may be associated with other IDs for said individual to support collecting pertinent data and de-duplicating records about the same person held by various resource holders.

Classifications 534 are another useful form of meta data, and may refer to an element, a class of elements, or aggregation of elements and/or classes. These include medical classification, or medical coding systems 535, which are frequently used to transform descriptions of medical symptoms, diagnoses, laboratory results, medications, procedures, topography, treatments, and the like into universal medical code numbers. These include both country specific standards and international classification systems, and include both statistical and nomenclature classifications.

Persons of ordinary skill in the art are aware that such meta data may be used to describe the type of data, for example "a diagnosis" without revealing the content, and designate that such value is protected in accordance with a particular privacy directive. Designated segments 536, and other classes 537 are also included to illustrate that such systems is intended to be both flexible and extensible. Dates 538 may also be used to identify dates of care, medical encounters, natural events, and the like. Similar to panels, as described previously, such classifications may optionally be dynamically directed through a current panel descriptor that would enable, for example, all of the data elements considered to be "Personal Health Identifiers" (or PHI) to be addressed through a single directive, and enable a grantor to revise its definition of PHI over time and for such revision to be immediately applicable even to data that was acquired well before such change occurred.

Another useful aspect of the data 518 that is preferably addressed is the provenance 539, which is generally understood to be information about the entities, activities, and people involved in producing the data. Such information is useful to form assessments about the quality, reliability, or trustworthiness of the data, and in certain cases how it should be interpreted and/or analytically handled, as well as its reproducibility. The W3C has a Provenance Working Group, whose proceedings and recommendations may be useful in this component part of the ontology. For more information, refer to http://www.w3.org/TR/prov-overview/.

In one optional embodiment, provenance included the original data source 540 and/or a document ID 541 for any data 518 originating from the system itself. The original data source 540 may be further resolved based on the date such data 518 was created 541, the organization where it originated 542 and the individual within such organization 543 responsible for its creation, as well as the purpose for which it was created 544, all of which attributes may among other uses, be of relevance in expressing the applicability of certain laws 507, policies 508 and/or preferences 509.

In one optional embodiment, such provenance 539 component of the ontology may be employed to capture certain information associated with any such data 518 being disclosed to a resource seeker 517. For example, this could include the individual 515, entity 516, or application under direction of one of such individuals, entities or affiliates thereof, accessing such data 518; the date and time on which this event transpired; the location of access; a verification from the computer being used for such process of the machine ID, data and time, and geo-location of the access; the purpose of use indicated by said person for accessing such data 518; and an affirmation or representation as may, from time to time be deemed advisable to carrying out the objects of the invention. Without limitation, these include reporting to the audit service 611, establishing the basis for the payment service distributions 640.

Pre-condition 545 refers to other factors accompanying the directive that can be used to help determine the correct data sharing or data protection decision. By way of various non-limiting examples, such pre-conditions may include applicable time period 546 (e.g., on date X, during period from X to Y, etc.); the purpose of use or reason for access 547 (e.g., provision of care including clinician-order fulfillment, medical research, clinical trial, referral of care, reporting back to referring clinician, etc.); the type of access 548 to such data 518 by said data seeker 517 (i.e., as more particularly described in relation to FIG. 7, which discloses an illustrative user interface for specifying such accessibility preferences); and Other Criteria 549. Pre-condition 545 may also include Boolean combinations of these sorts of conditions or factors.

By way of further illustration and not limitation, such Other Criteria 549 may also include pre-conditions including selections and level of identity proofing and/or minimum authentication requirement placed on the resource seeker 517; state of consciousness or mental faculty of the subject 533 to whom data 518 applies (e.g., unconscious, incapacitated, unsound mind, etc.); the availability of said subject 533 (or their designated agent) for consultation (e.g., unable to contact by various methods for some period of time); a limit on number of accesses (e.g., one time only, up to three times, etc.); and the like. In addition, pre-conditions may include explicit requirements for securing prior express consent; the obligation to de-identify data 518 in accordance with HIPAA standards, Common Rule standards, or another jurisdictional standard; geographic areas for which a directive is applicable (e.g., facilities located in the state of New York, residents of any European Union member country, etc.); specific circumstances surrounding highly-sensitive conditions (e.g., AIDS, drug/alcohol use, psychiatric context, etc.); and other conditions embraced by the applicable law 507, policy 508, or preference 509.

As with all of the foregoing elements comprising the ontology, to the extent there is wide agreement on such terminology, it is preferable to use common standards to resolve and express each of such attributes. Such terminologies are well known to those of ordinary skill in the art; and Applicant's '544 patent indicates a number of illustrative examples. Also, as noted within FIG. 5(*a*), composites of these various elements may be used in accordance with the principles of the invention.

FIGS. 5(*b*)-5(*d*) provide several examples of how the ontology described with regard to FIG. 5(*a*) can be employed with respect to an illustrative use case. In a non-limiting example, these figures are based on a particular instance wherein the wishes of an individual about who may have access to certain portions of her information may reflect a number of important nuances. These figures are based on a hypothetical case wherein a subject, whom we refer to as Ann Summers, has a family history that places her at risk of Huntington's disease, a fatal disease for which there is presently no known cure. For the sake of illustration, we assume that she is in her late-20's, single but presently dating someone, currently has no symptoms of the condition, and is just starting out in a promising career.

The Huntington's gene (which is also known as the HTT gene) is unique for a number of reasons, which makes it useful for illustrative purposes. It is a single gene, whose alleles are dominant, meaning that if either parent has the gene then any offspring has a 50/50 chance of also having it. The condition commonly begins to manifest noticeable symptoms between the ages of 35 and 44 years; and according to references cited in Wikipedia, between 33% and 69% of the individuals with the condition experience depression, and 7.3% of those with the disease take their own lives and up to 27% attempt to do so. Moreover, learning of the diagnosis often results in significant feelings of guilt, and because there is no known treatment, the treatment benefits of early diagnosis are questionable. Accordingly, whereas 99% of the individuals expressing symptoms of the disorder and who have a family history of the disease receive a genetic test to confirm a diagnosis, less than 5% of the pre-symptomatic cases currently undergo genetic testing.

While a number of the foregoing characteristics are quite extreme (and the level of certainty is quite high), as scientific knowledge progresses to where similar levels of confidence can be predicted for multi-gene disorders and that take into account protective regions of other genes and such subtleties, it is not unreasonable to anticipate that similar sorts of challenges regarding how to address genomic findings will evoke similar kinds of concerns and opportunities. By practicing the principles of the invention, an individual such as Ann in the hypothetical case has a number of options that are simply not possible under the present state of the art, and that are likely to make genomic testing much more readily acceptable, particularly for large population sequencing where (from an epidemiological sense) some percentage of cases will inevitably be similar to Ms. Summers' case.

FIG. 5(*b*) indicates how an individual who does not wish to know whether or not she tests positive for a risk such as, in this illustration Huntington's disease, may wish to establish her settings. This could be for any number of reasons, such as concern about what a definitive diagnosis could mean for her career, her social relationships, her ability to secure long-term care insurance, and even how her own family would respond or how she'd deal with it. Heading 550(*a*) indicates that the highlighted portion of the illustration is expressing the use case stated in descriptive paragraph 550(*b*). As indicated, the grantor 501 is an individual 551 who is the subject of the data, Ann Summers 552. Ms. Summers, whose authority 506 is based on her personal preference 553, wishes to prohibit 554, the data holder 514, who in the illustrative case is assumed to be a specific organization, Illumina, Inc. 555, and any of its affiliates 556, from disclosing certain data 518. The particular data that is the subject of this directive is any data type 557 on any date 558 of which she is the subject 559 and the content of which is a data super type 560 of genomic information 561, whose literal content 562 is the HTT gene 563 (which pertains to Huntington's disease) and/or whose location 564 is on the short arm of the Chromosome 4 in region 1, band 6 and sub-band 3. This could be accomplished through use of controls such as described with respect to FIGS. 2(*c*)-2(*e*). The ontology also describes the provenance 539 of the data 518 that the directive addresses, namely that the original data source 566 is Illumina, Inc. 567; the purpose that the data was created was participation in the Understanding Your Genome program 568 and that the information was created on March 8, 2015, reflected in oval 569. And finishing the directive, we note that the data seeker 517 to whom the directive pertains is Ms. Summers herself 570.

In accordance with the principles of the invention, another attribute of the invention that could be effectively employed in cases where information about the disorder are not as well defined as in the case of Huntington's disease is the use of Panel setting 528, that in one preferred embodiment might be used in lieu of calling out a specific gene or chromosomal region. The advantage of this alternative approach would be that as scientific knowledge develops, the effect of such designation would apply to the genes and/or chromosomal regions known to be of relevance at the time of a future inquiry (as opposed to being limited to what was known about the genotype to phenotype correlation at the time the privacy directive was created). This feature of the invention is described in relation to FIG. 5(d) below.

Figure 5C:
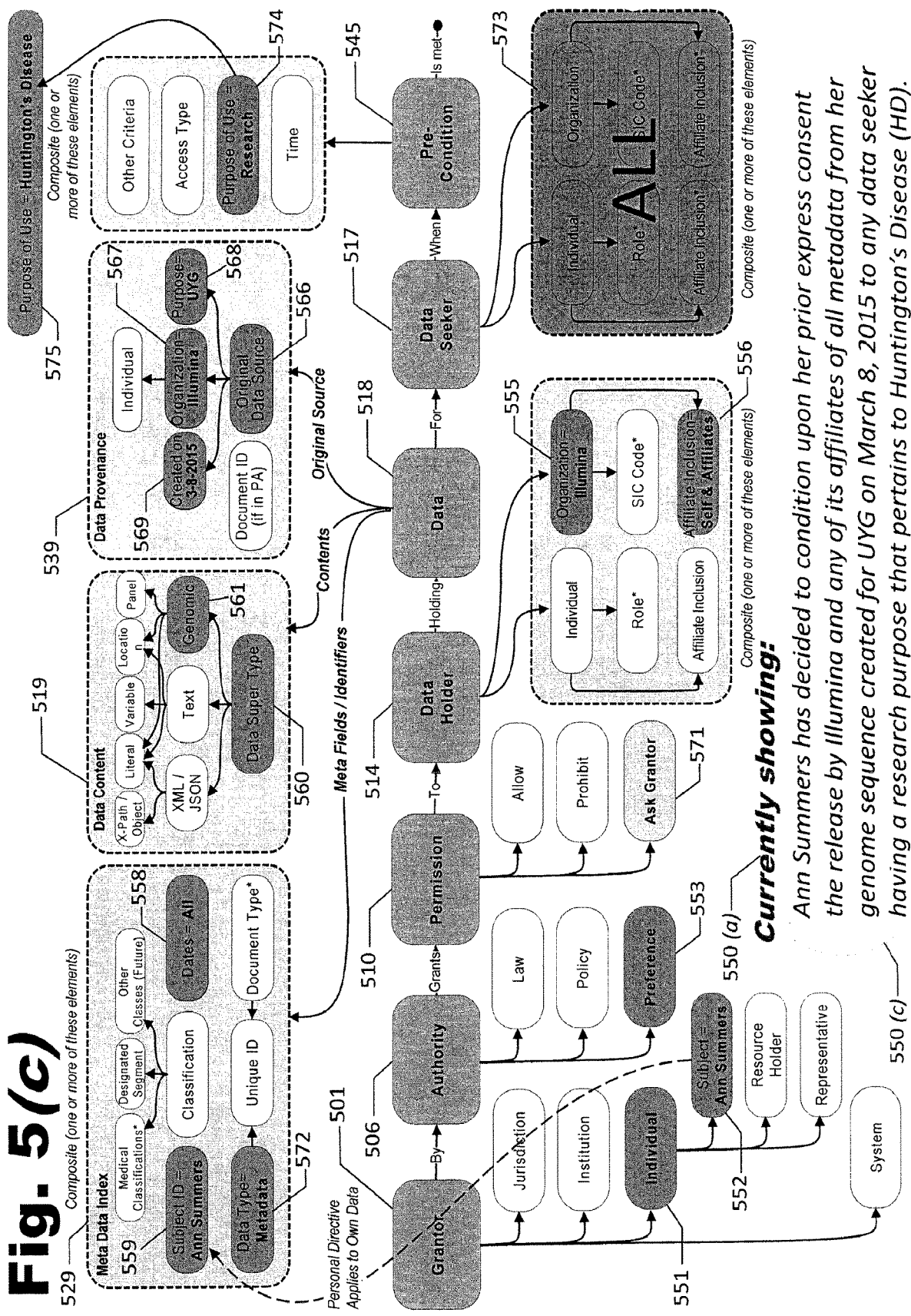

Turning now to FIG. 5(c), a second privacy directive is expressed using the foregoing disclosed ontology to address the anticipated desire by an individual such as Ms. Summers to help advance medical research into the disease affecting her family and that will potentially affect her in the hypothetical case, and to hopefully finding a cure to Huntington's disease while at the same time balancing this interest against her wish to assure that she is not inadvertently informed of her own status and/or adversely affected by discrimination related to the condition or her potential to have it. As shown, this goal 550(c) can be achieved by setting her preferred permission 510 to "Ask Grantor" 571; and the data type 518 to "metadata" 572. As described previously, this has the advantage of not revealing the actual genomic sequence, but instead merely metadata regarding it. This may be more appropriate given the breadth of her intended disclosure, which in this case is assumed to be to any data seekers 573 subject to the pre-condition 545 that the purpose of their research 574 is Huntington's disease 575. Thus, in carrying out the principles of the invention, such a setting would permit Ms. Summers (while remaining anonymous) to learn about each research project and researcher expressing interest in obtaining her data, and upon that basis to be able to decide whether or not she wished to grant them such access.

Figure 5D:
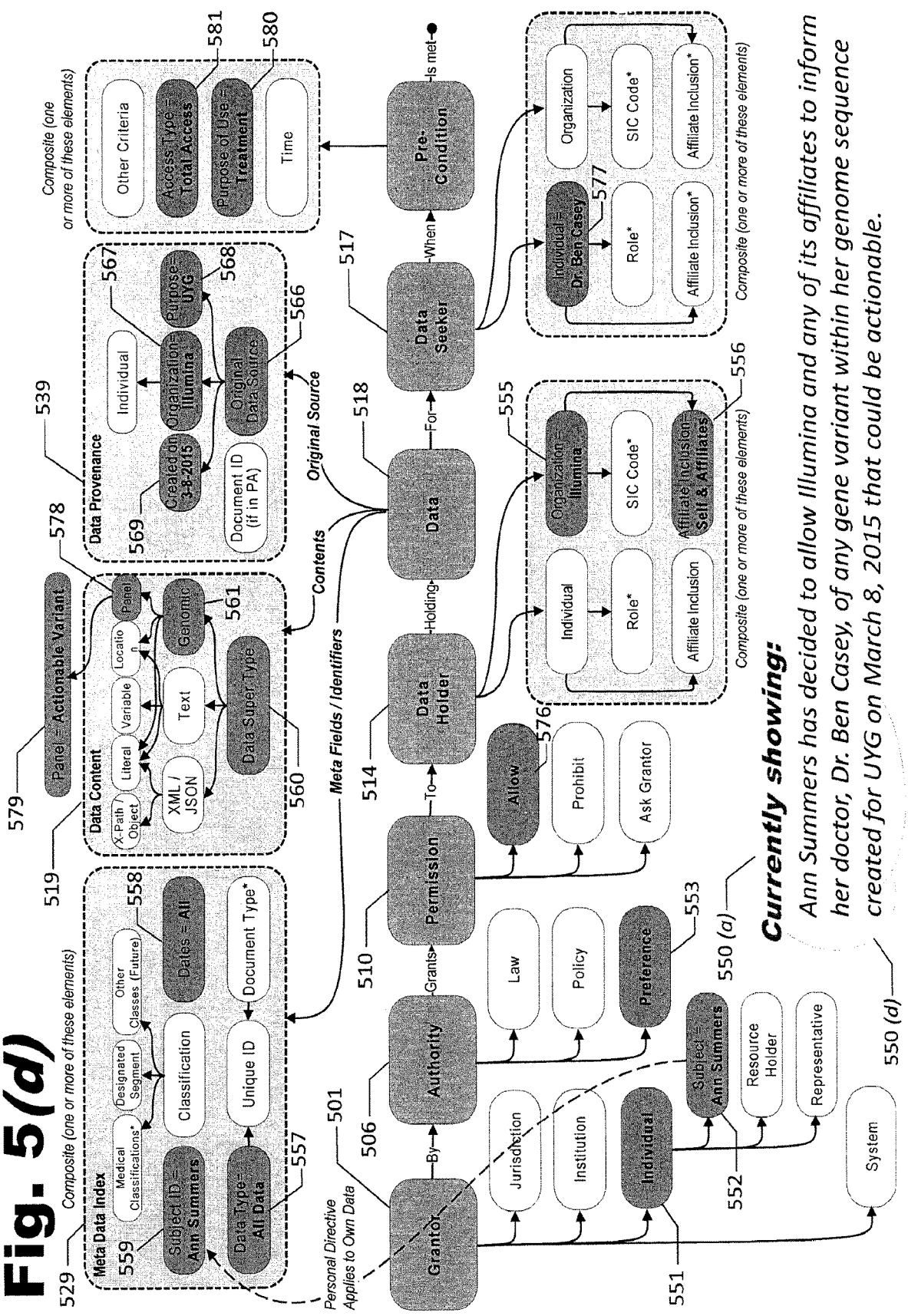

FIG. 5(d) focuses on another seemingly reasonable objective that an individual such as Ms. Summers is likely to have, namely that she be aware of any actionable information that her WGS result provides. In this regard, she is interested not only about potential future Huntington's breakthroughs, but also about anything else that might affect her proper care. She knows that this will become even more important as she thinks about a family of her own someday to ensure that if she is carries an excessive number of CAG repeats on the HTT gene that she and her spouse can consider fertility options at the appropriate time. In order to address these considerations, she wishes to allow her personal doctor to know about any actionable data, and counts on him to decide whether or not to inform her, and when he feels it becomes critical to do so. FIG. 5(d) shows a third privacy directive employing the ontology to express goal 550(d). This is accomplished by setting her preferred permission 510 to "Allow" 576 her physician, Dr. Ben Casey 577 to access all of her data 557 that is, at the time part of panel 578 that is considered to be "actionable" 579 for treatment related purposes 580.

Given the extensive amount of research taking place in the genomics field, and with the cost of WGS and NGS dropping dramatically, the amount of actionable information is likely to change rapidly. By practicing the principles of the invention and using the panels 578 setting, an inquiry by her doctor at some future date such as the timing of her periodic physical exams may reveal that something which was not recognized as being actionable at the time her genome was sequenced has become actionable (or alternatively, something that was actionable but for someone who was older or facing different conditions such as the potential of becoming pregnant) might dictate a different decision being made from information that was known at the time she was originally sequenced, but that was not pertinent to her under the prior conditions.

Her doctor may be assisted in keeping track of such updates through establishing a "standing order" inquiry respecting Ms. Summers, as described in Applicant's '049 patent, and her willingness to grant to such physician "total access," as described with respect to setting 706 in relation to FIG. 7 hereof.

Figure 6:
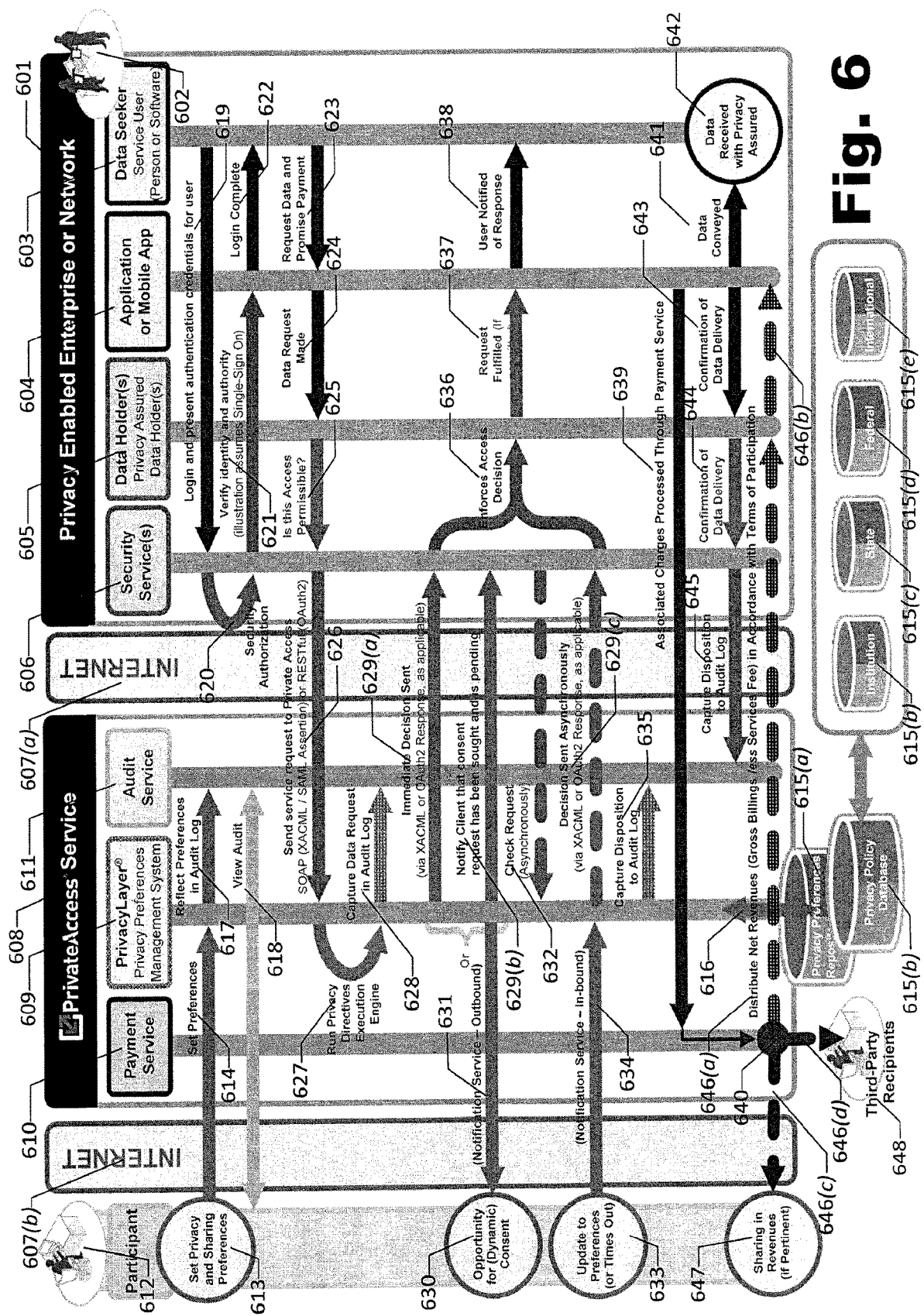
FIG. 6 is a sequence diagram showing the interaction between a party requesting data from a privacy-enabled system, the private access bureau, and the participant for controlling the release of information by an enterprise or privacy-enabled device in accordance with the teachings of the invention.

Turning next to FIG. 6, an updated sequence of services and API calls is illustrated for the purposes of carrying out the teachings of the invention. FIG. 6 represents an update to Applicant's previous disclosure of such activities in FIG. 5 of Applicant's '544 patent and the corresponding description. As explained previously, in one preferred embodiment, the services of the private access bureau are exposed as integration profiles via stateless, reusable Enterprise Service Bus (ESB) services developed as adapters.

FIG. 6 shows the relationship in one preferred embodiment between a privacy-enabled enterprise or network 601, comprised of a data seeker 602 (whose activities are illustrated therein by rectangular box and vertical line 603 for either a person, a software algorithm or application), and who through a browser-based interface, application or mobile app 604, is in contact with one (or perhaps multiple) data holder(s) 605. Said application 604 may be an integral part of a data holder's systems, or an independent service such as a search engine or application operated by one or more other parties who function as an intermediary for locating information held by said data holder or a group comprised of multiple data holders (in an non-limiting example, several medical centers, pharmaceutical firms, testing laboratories and various registries) 605. As shown, said party (or parties) also includes security service(s) 606.

Said enterprise or network 601 is in communication over the Internet or intranet 607(a) with the private access service 608. As shown, the private access service includes the privacy preference management system, which is also referred to variously as the PPMS or PrivacyLayer®, 609, a payment service 610, and audit service, 611. As shown, the private access service preferably employs multiple binding adapters to accommodate multiple profiles and bindings, i.e., SOAP over HTTPS, REST-full services, XML over HTTPs, and newer technologies that supplant these in the future. All API calls are secured using industry standard patterns such as WS-Trust, SAML and XACML, enforcing message authenticity, integrity and confidentiality.

The illustrative API call sequence shows participant 612 setting 613 privacy and sharing preferences 614 from any standards-based Web browser or Web-enabled mobile device connected via network 607(b), such as the Internet, to the privacy preference management system (PPMS) component 609 of the private access bureau 608. As previously described in conjunction with Applicant's '544 patent, such privacy preferences 613 can be for an individual participant such as a patient or their legally designated representative or proxy.

Said participant 612 can also be the appropriately authorized party representing any other "grantor" including, but not limited to an enterprise such as a laboratory or physician practice that generated the data initially, an institution who is the data holder such as a medical center, research enterprise or insurer; or a jurisdiction such as a local government, state, federal or international body having some level of authority with respect to individual persons' health related data. Entries made by such individual participants are retained in a privacy preferences repository database 615(a), corresponding to 1206 of FIG. 4 of Applicant's '544 patent, which as shown therein and illustrated here by two-way arrow 616, is connected to the PPMS.

The PPMS is also connected via two-way arrow 616 to privacy policy database 615(b), which in turn contains policy directives, preferably stated in the ontology described with respect to FIG. 5 above or other machine computable form, reflecting institutional policies (including but not necessarily limited to pricing policies) 615(c), State or provincial law 615(d), Federal or national law 615(e), and international standards and treaties 615(f). This architecture is intentionally extensible in order to enabling the private access bureau to accommodate other laws, rules, regulations, policies, or charges responsive to other applicable bodies such as regional, county, city, trade affiliations and the like; institutions whose earlier services in generating, interpreting or analyzing intermediate products added to the value of the data; affinity groups, and other individuals who are entitled to some rights or share in proceeds, if any.

Audit service 611 is updated 617 for the set preferences event 614. Such audit service 611 included within the private access bureau 608 includes an audit database. This service provides the ability, at any time, for the participant 612 to login to the private access bureau and view 618 an audit history of events affecting data for which he or she is the data subject, or covered by the policies he or she administers. To the extent possible, this preferably includes privacy preference settings, authorizations, requests for access, and access to or sharing of the bioinformatic data segments from any privacy-enabled system or privacy-assured application. Additionally, such participants 612 can preferably subscribe to receive alerts based on updates to the audit service 611 that affect the data and/or records of such data subject.

A data seeker 602 logs in 619 and authenticates as an authorized user of a privacy-enabled system of the application or mobile app 604 within a privacy-enabled network 601, including data holder 605. The security service 606 employs standard security practices 620 to verify the identity and authority 621 of the data seeker. This standard practice is, in a preferred embodiment, assisted through the use of a single-sign-on (SSO) protocol such as OpenID to authorize such use, whereupon if successful a message is sent to the data seeker indicating that login is complete 622.

Data seeker 602 then requests data 623 using the application or service 604, and promises to pay for such receipt of information, if applicable. Such payment may take any form, including without limitation a transactional fee, an ongoing subscription fee, or by consenting to a privacy policy that permits the display of advertising in conjunction with such search and/or retrieval functions. Said data request 623 is conveyed as a data request 624 to the actual data holder 605. Before responding to such request for access to said data (or in the case that the application is a search engine or its equivalent, before presenting responding to a request for search results that are responsive to a search inquiry), the data holder 605 inquires whether such access is permissible 625. As part of the security service 606 responding to such inquiry, said service preferably sends a service request to the PPMS 609 using an XACML-based message including a SAML assertion (if SOAP based messaging is employed) or using RESTful exchange through an OAuth2 protocol-based API 626.

Upon receipt by the private access bureau 608 of such inquiry, the PPMS 609 runs the privacy directives execution engine 627 generally in the manner described with regard to the operation of the private access bureau 608 in the '544 patent, the description of which is incorporated herein as though set forth in full herein. The system captures the data request event 628 in audit service 611; and if the inquiry is capable of being answered immediately based on the database contents of the privacy preferences database 615(a) and/or privacy policy database 615(b), responds to security service 606 for data holder 605 via an XACML statement or OAuth2 response 629(a) with the applicable privacy directive.

Alternatively, if the request is not capable of being answered without input by the data subject (or another grantor, as applicable), then a notice of its processing status having been pended 629(b) is communicated to the security service 606 for record holder 605, and a request for express consent 630 is sent 631 across network 607(b) to said participant 612. Audit service 611 is simultaneously updated so that in the event data holder 605 wishes to check the status 632 of the decision, this information is available to said data holder 605 across network 607(a) from audit service 611. Subsequently, when participant 612 consents or declines 633 to permit the action proposed in the manner described in detail in Applicant's '544 patent (or the time allotted for such decision transpires thereby triggering an automated response in accordance with a rule in contemplation of such passage of time without any response), this response (or the automated action taken in the absence thereof) updates 634 and two-way arrow 616 the privacy preferences repository database 615(a), asynchronously communicates a privacy directive 629(c) to the security service 606 for data holder 605 via an XACML statement or OAuth2 response, as applicable, over network 607(a), and updates the audit service 635 reflecting such action.

Irrespective of whether the response is immediate, indicated by arrow 629(a), or asynchronous as represented by dashed arrow 629(c), security service 606 enforces the action in accordance with said directive or by permitting the data holder to "break the glass" and thereby ignore said directive, each illustrated by arrow 636. On this basis, the request by data seeker 602 to receive said data is fulfilled 637, either directly from data holder 605 or through application 604, which notifies 638 data seeker 602 of the availability of the requested data, if applicable, or alternatively notifies the data seeker that the request cannot be fulfilled, if access was denied or simply was incapable of being resolved to the satisfaction of said data holder's policies. The associated charges, if any, for such access are in a preferred embodiment processed 639 through the payment service 610, with the proceeds (net of a service charge) 640 queued for distribution by said payment service 610.

The requested data is then conveyed 641 to the data seeker, thereby fulfilling 642 its prior request 623. Confirmation of the delivery of such data conveyed to the data holder 643, the security service 644, and recorded in a capture disposition event 645 update to the audit service 611. In accordance with the terms of participation and/or institutional policies of the data holder, the net revenues 640 from the payment made by the data seeker (if any) are distributed 646(a)-(d) by the payment service 610 to the data holder 605, and application or service 604, participant(s) 647, and any third parties 648, for example as a donation on said participant's behalf to a health-related nonprofit favored by the participant.

FIG. 7, which consists of nine subparts, presents an illustrative user interface for intuitively establishing preferences in one preferred embodiment regarding the right to analyze, discover, view, use, export, and link bioinformatic data including genomic data with other de-identified and personally identifiable health information and contact details for the individual to whom each of such element(s) pertain.

Figure 7A:
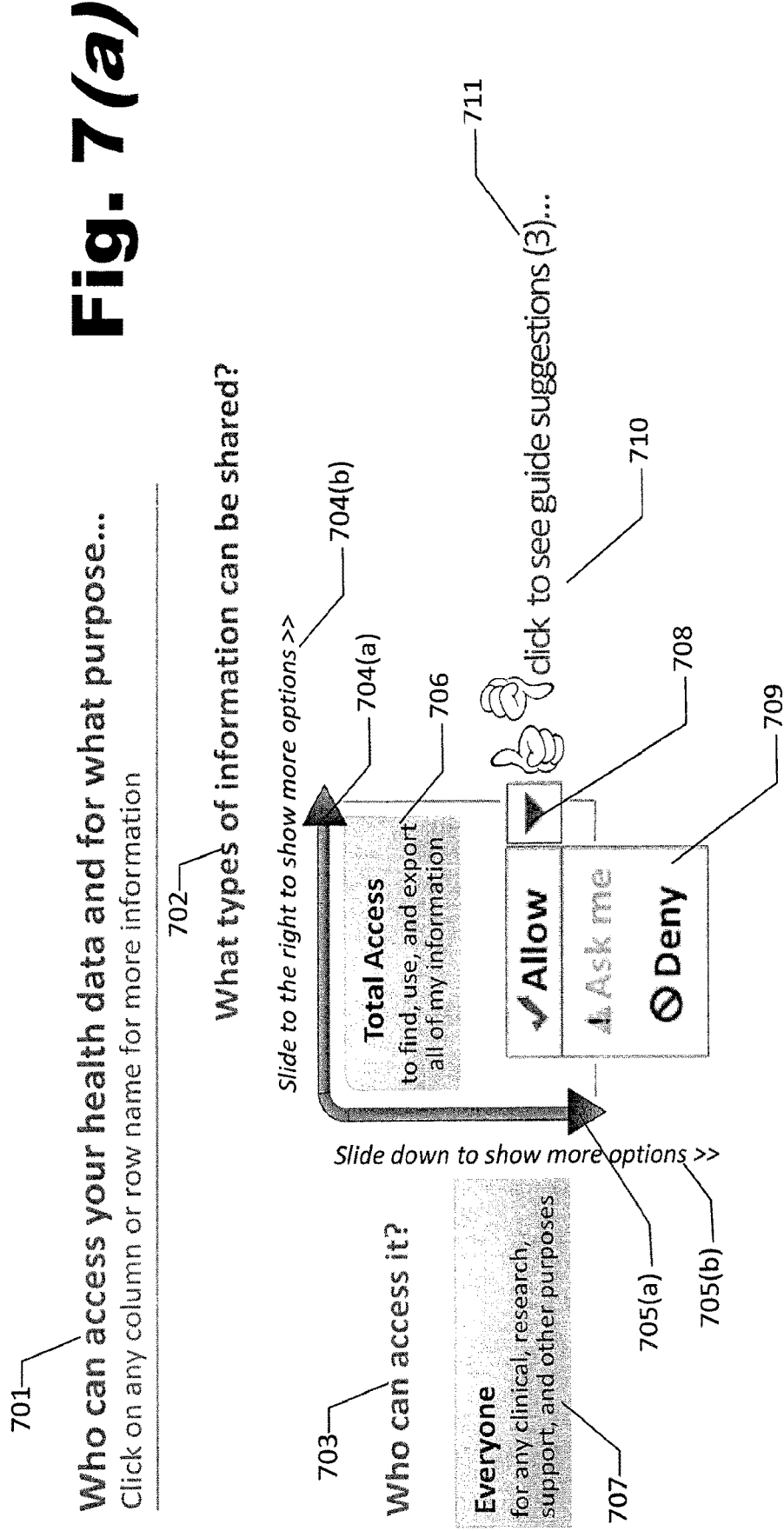
FIG. 7, consisting of subparts 7(a)-7(i), is a series of illustrative user interface designs for intuitively establishing preferences regarding the right to analyze, discover, view, use, export, and link bioinformatic data including genomic data with other health information and contact details for the individual to whom each of such element(s) pertain.
Figure 7E:
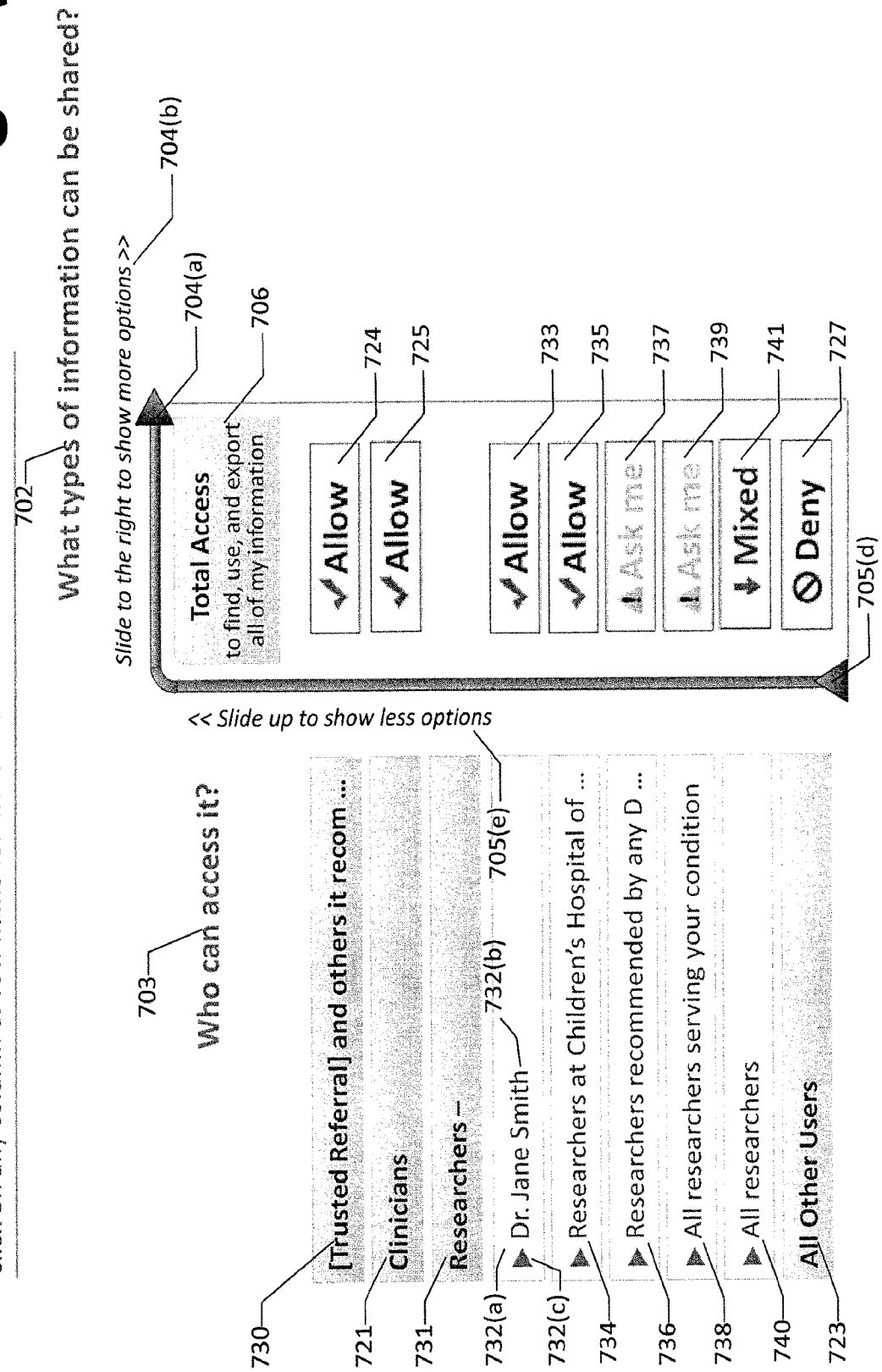
Figure 7F:
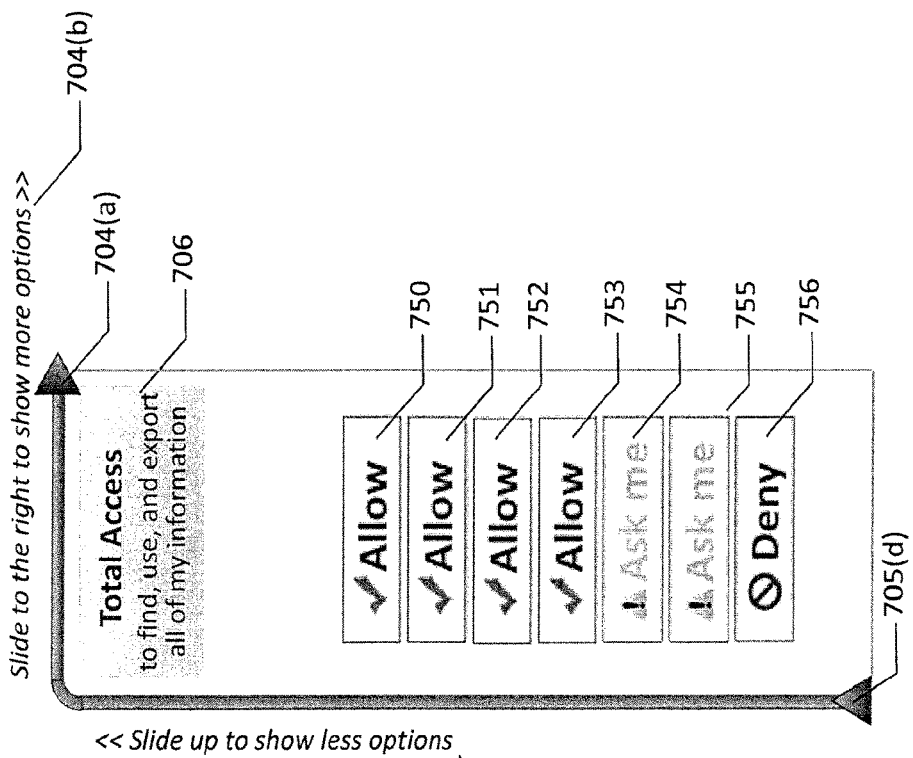
Figure 7H:
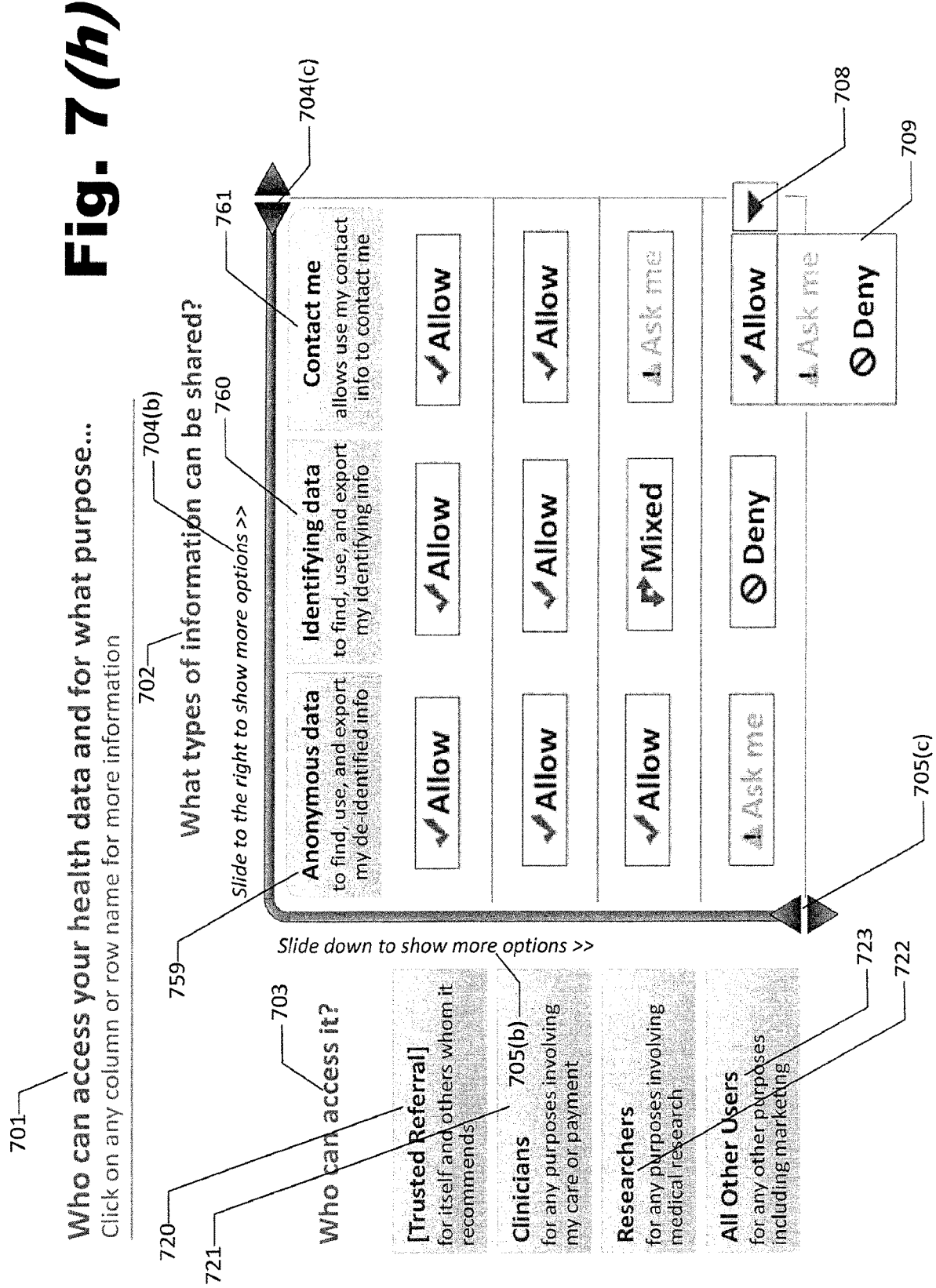

FIG. 7(a) provides an illustrative drawing of a user interface for expressing one's preferences respecting the question "Who can access your health data and for what purpose" 701. A table of configuration preferences is shown, the horizontal axis 702 of which addresses the types of information, and the vertical axis 703 of which addresses who can access that information, and the intersection of such columns represents the particular preference expressed for such information. Persons of ordinary skill in the art will understand that each of such selections represents a preference of use within the ontology illustrated with reference to FIG. 5 and, among other things, of use in operating a private access bureau to carry out the principles of this invention and the '544 patent.

In one preferred embodiment, such horizontal axis 702 can be widened by sliding handle 704(*a*) in the direction indicated and reinforced by message 704(*b*), thereby making accessible to the user increasingly more granular selection options. Similarly, vertical axis 703 can be elongated by sliding handle 705(*a*) in the direction indicated and reinforced by message 705(*b*), thereby making accessible to the user increasingly more granular selection alternatives. In both cases, sliding handles 704(*a*) and 705(*a*) in the opposing direction would "fold in" such granular options into broader statements encompassing such underlying granularity. Accordingly, as shown in FIG. 7(*h*), in an optional embodiment, such slider handles change form to 704(*c*) and 705(*c*) to reflect that the slider may be moved in either direction; and change to yet a third form as illustrated by 705(*d*) in FIG. 7(*e*) to reflect that the axis has reached its most granular extreme, which is reinforced by the accompanied message 705(*e*).

FIG. 7(*a*) shows said table in its most constricted form, what simply presents such selections in the form of a 1-by-1 table. As shown, the sole column 706 in such table, entitled "Total Access", in combination with the sole row 707, entitled "Everyone", allows a user to specify a privacy preference that would apply to the ability for all of his or her information to be found, used and exported by "everyone" for any clinical, research, support and/or other purposes, including marketing. As illustrated, such selection can be made by clicking on arrow 708 to reveal in a preferred embodiment three selection options 709, respectively corresponding to permission options 511, 512 and 513 illustrated in FIG. 5(*a*) hereof.

Based on the foregoing description, it should be readily apparent that by selecting "Allow" (in turn corresponding to permission option 511) using pull-down list 709, this user is indicating her wish to make all of her information accessible to everyone. And were this selection to be made, then sliding handles 704(*a*) or 705(*a*) in the direction designed to open the granular selections comprising such broad declaration would reveal "Allow" as the setting for all such revealed cells. Employing the principles of the invention, changing one such cell to "Ask me" or "Deny" would take precedence for that selection but all of the other cells would remain in their original "Allow" state, as more particularly described with respect to FIG. 7(*e*), below.

In a preferred embodiment, such selection options are accompanied by a link 710 to suggestions for setting one's privacy preferences made by "guides", as more particularly discussed in Applicant's previous '544 patent. In one preferred embodiment, such message would display the number of such guide recommendations 711 that are available to assist the system user. Such assistance by knowledgeable individuals can be useful to helping reduce a sense of overwhelm and/or frustration that may otherwise occur with granular controls, while simultaneously avoiding the system's design being coercive for a particular outcome. Access to such guide suggestions, which may optionally include the opportunity to view video interviews, read quotes and materials, and view (and if acceptable adopt) a template supplied by the guide as a beginning point for the system user, may be very helpful in assuring that the selection is meaningful and perhaps more comprehensive than if each individual must think through each selection without access to such assistance from trustworthy persons.

Turning next to FIG. 7(*b*), an illustration is provided to indicate the consequence of a user selecting the "Deny" option from pull-down list 709 of FIG. 7(*a*). As shown therein, the privacy preference to "Deny" 712 indicates the individual's wish to deny access to all of their information to everyone (i.e., to make such information not accessible by anyone). In this instance, the illustration depicts that in a preferred embodiment, the system would automatically compare such preference to the database of jurisdictional laws and institutional policies and identify if a "superior right" under applicable law is present that could render such preference unavailing. In such instances—and in the case of the illustrative example shown—the action taken would cause a symbol 713 to appear on the face of such selection, and by this means inform the user that her selection conflicts with another setting that takes precedence and could result in her preference being disregarded.

In the case of the illustrative drawing shown in FIG. 7(*b*), selecting "Deny" for all data (at least for users in the United States) would trigger such a symbol 713 in the event the data holder was a Covered Entity (as defined in HIPPA). This is because under HIPAA, a Covered Entity can share certain health data (including personally identifying health data) for "treatment", "payment" or "operations" purposes without the authorization of the individual (and irrespective of the individual's express wishes to the contrary). Message 714 preferably accompanies and summarizes the meaning of symbol 713, and includes a link 715 for individuals wishing more details.

While not shown in such illustrative drawings, it will be readily understood that such explanation may include a link to the applicable statutes and/or policies that prompted such alert 713, and may provide a means (such as "Express your views to your Congressional representatives") for interested persons. In this case, it would most likely also explain the institution's policies that might be less broad than the law, for example to honor such wishes except in certain limited circumstances. And in a preferred embodiment, such information would explain that should the law subsequently change in such a way that the individual's preference were to take precedence over the law, then the data holder would abide by such change in applicable law. Persons of ordinary skill in the art will readily appreciate that the foregoing is illustrative of one of the benefits of the invention, in providing transparency and placing accountability where it rests, and in automatically enabling a privacy-assured system to at all times be in accord with the latest instantiation of applicable laws, institutional policies and/or personal preferences, which will materially reduce the costs and disruption created to account for such changes under current state of the art in access control technology and compliance systems.

FIG. 7(*c*) shows how, in a well-ordered system, the user interface can intuitively indicate to the use that variability exists within the hidden (i.e., more granular selections). In one preferred embodiment, "Mixed" display 716 appears, and includes an arrow 717 pointing in the direction of the table in which the granular settings are not all the same. The first time that such "Mixed" display 716 appears, in a preferred embodiment it would be accompanied by an explanatory message 718. This message would preferably appear each time a "Mixed" display appears unless and until the user places a check in checkbox 719 to indicate that the message need not appear in the future.

FIG. 7(*d*) shows how the user interface responds when a user clicks on the "Mixed" cell 716 in FIG. 7(*c*). As shown, that selection results in the table opening in the direction of arrow 717 in logical increments to reveal such granularity and the corresponding settings for each, and as reflected by the repositioning of slider handle 705(*a*). In one optional embodiment, the first logical expansion in such vertical direction is to reveal the four major groups comprised within the "Everyone" classification 707 (shown in the preceding three sub-parts). In this case, the next level of detail selected by a system designer employing the principles of the invention could reveal, for example, a category entitled "[Trusted Referral]" 720, and explained in the accompanying text to relate to both the entity or person itself as well as others whom it recommends.

It will be apparent to persons of ordinary skill in the art that "Trusted Referral" may, depending on context, pertain to a support group, medical center, charitable organization, or individual (such as a provider) who suggested the user employ the system and thus in one preferred system listing this referral and their recommendations first helps to ensure that the focus of the user's activity is principally whatever brought them to be using the system. Other categories of users comprising "Everybody" are "Clinicians" 721, referring to anyone involved in the individual's care and/or the payment therefor; "Researchers"722, containing anyone conducting medical research; and "All Other Uses" 723, containing everyone else for any other purpose, including marketing. As shown, the corresponding settings for each of these groups, 724-727 respectively, is also revealed.

In a preferred embodiment, the user would have the option to click on a cell, which would open arrow tab 708 and revise the selection using pull-down list 709, as explained with respect to FIG. 7(*a*). As shown, whenever a selection is being modified, in an optional embodiment, a message 728 is displayed to indicate that one or more other users have expressed comments about the particular selection. In one preferred embodiment, this message could indicate the number of comments 729(*a*) regarding a particular selection, and whether those comments tend to agree or disagree with the proposed setting, as reflected in 729(*b*) and 729(*c*), respectively. Such use of ratings and comments by other users is described in Applicant's prior '544 patent, to help inform such selections.

In other fields such as telecommunications, software programming, retail, finance, entertainment, media and advertising, a number of large group collaboration technologies have been successfully employed to employ the "wisdom of the crowd" to issues involving choice. The cover story in the Jun. 20, 2005 issue of *Business Week*, entitled "The Power of Us: Mass Collaboration on the Internet is Shaking Up Business," provides a discussion of this trend toward "mass collaboration" and describes the trend toward using a variety of Internet-based technologies to enable companies and industries to "tap into the collective intelligence of employees, customers and outsiders."

A number of patents have been directed to such systems of the prior art, including U.S. Pat. No. 6,189,029 to Fuerst, entitled "Web Survey Tool Builder and Result Compiler"; U.S. Pat. No. 6,457,045 to Hanson et al, entitled "System and Method for Group Choice Making"; and U.S. Pat. No. 6,801,900 to Lloyd, entitled "System and Method for Online Dispute Resolution". Additionally, those of ordinary skill in the art will recognize that a number of technologies help enable such services. In addition to explicit ratings, these include collaborative filtering techniques to generate personal recommendations based upon explicit ratings, as well as "content-based" filtering techniques that extract key concepts and automate the categorization, cross-referencing, hypertext linking and/or presentation of such information. Another technology is "content mining," which automatically analyzes text and other unstructured content to make intelligent decisions and recommendations. And yet another technique involves the use of "implicit ratings" based on specific actions of participants and which are, in turn, used to provide recommendations based on peer group categorization but without resorting to explicit ratings.

Well conceived implementations employing these and other related network-based technologies are broadly understood as increasingly providing a way "of turning self-interest into social benefit—and real economic value [through an] 'architecture of participation,' so it's easy for people to do their own thing . . . [but where] those actions can be pooled into something useful to many." The June 2005 *Business Week* article describes capabilities like the seller ratings on eBay, song ratings on Yahoo! and millions of customer-generated product reviews on Amazon.com, eOpinions.com and a multitude of similar services—all of which, at their core, "help decide hits and duds"—as being examples of the power of such technologies in action.

Other than as disclosed in Applicants prior '544 patent, these sorts of technologies have not heretofore been proposed nor applied to the field of setting privacy preferences. As shown in FIG. 7(*d*), such facilities can be intuitively integrated into the user interface so as to assist individuals looking to consider a particular action. For example, in several non-limiting illustrations, particular organizations, specific individuals and/or proposed uses of data may be voted up or down based on reputation scores. Similarly, it may be useful for individuals who are affected by a particular disorder to designated segments of the bioinformatic data such as a gene that bears closer scrutiny by anyone with a certain family or health history and describe the value of opening up the information to a greater number of data seekers or one data seeker in particular. Or in other cases, persons who are concerned about the potential for misuse by particular groups may wish to explain the importance of protecting certain information from being discovered. In one preferred embodiment of the invention, such crowd-sourcing techniques respecting selections would be employed as a supplement to the foregoing described guide recommendations, and may be turned on or off (and/or filtered to select from whom comments are accessible) from the user's general preferences, or as a result of placing a check in checkbox 719.

FIG. 7(*d*) also illustrates that as the level of granularity increases, in one preferred embodiment, the user interface automatically creates groups of the successively more granular selections into logical groups under a single columnar heading or row title. Such groups could be created on the fly, or alternatively be pre-authored and programmed to display when applicable so that such groups appear and thereby help avoid overwhelming end users. "Mixed" indicator 726 illustrates the use of such a designation to indicate that additional variability is present within the more detailed settings that comprise the "Researchers" category. Clicking on this selection opens in the direction (or as applicable, the directions) shown by arrow 717 to reveal such granular selections until they resolve to an expression for which the three primary preferences apply for any further granularity available in the setting. Accordingly, should all of the underlying granularity be made a single setting, then the display for the next higher level of abstraction would return to whatever level was applicable to all of the granular detail.

FIG. 7(*e*) illustrates the effect of selecting "Mixed" 726 in FIG. 7(*d*). As shown therein, row 730—which corresponds to row 720 shown in FIG. 7(*d*)—reminds the user that the row pertains to preferences for the referring entity and any other persons or entities that it recommends. And as shown in FIG. 7(*d*), the setting for everyone in this category is "Allow", which is reflected in cell 724. Similarly, "Clinicians", which are reflected by 721 and corresponding "Allow" selection 725, are repeated from FIG. 7(*d*). But at this deeper level of granularity, the "Researchers" heading 731 replaces the corresponding "aggregation" function provided by 721 in FIG. 7(*d*) and now lists at the next most granular level any persons or entities that comprise the (in this illustrative case) researchers category. In one preferred embodiment, the display of granular results may be implemented using an accordion-style user interface, were such detailed users list opens upon clicking on 721 in FIG. 7(*d*), and where clicking on title 731 closes the list and returns to prior view (i.e., in this case with "Mixed" revealed). However, if the user changes all of the selections shown to "Allow" for example, then upon clicking title 731, item 726 would thereafter display "Allow" to indicate such uniformity of settings below.

In a preferred embodiment, the settings are listed in the order from least granular to most granular. Thus, as shown, the first setting 732(*a*) is for an individual researcher 732(*b*), and includes a traditional file tree drop down icon 732(*c*) in the event the user wishes to set any further granularity. In this illustrative case, the icon is shown in its closed state, because there are no more granular settings, and any uses of the information by the indicated researcher for any medical research purpose are set to "Allow", and thus can be represented in the aggregation thereof 733.

By way of non-limiting example, if the user had elected to approve access for this researcher only for a specified purpose such as a particular clinical trial or study, then caption 733 would continue to display as "Allow" but by opening the file tree drop down icon, the name of that particular study would appear as the intended purpose for such allowed access; and if otherwise silent, then with regard to all other research purposes, the next less granular setting in which such researcher was included as a member would apply. For example if Dr. Smith were a Researcher at Children's Hospital of [Named Place] shown as row 734, then the setting of "Allow" indicated in 735 would apply. The same would be the case if she were a researcher recommended by the [Trusted Entity] 730. However, if she were not a member of either one of these groups, but instead included in the "Researchers recommended by any [other credible organization's] list of preferred researchers" 736, or a "Researcher serving one of the conditions listed in the user's health profile" 738, then "Ask Me" would apply on account of setting 737 or 739, respectively.

Certain aspects of the foregoing User Interface design principles may be observed in practice within websites currently employing Applicant's earlier teachings in this regard, including any Platform for Engaging Everyone Responsibly (or PEER) sites sponsored by Genetic Alliance as of the date of filing this application. However, other novel aspects, including use of the "Mixed" selections, slider-based access to increasingly granular settings, and in relation to displaying genomic data extend such earlier approaches to address particular requirements for segmented bioinformatic data as addressed herein.

FIG. 7(*e*) also illustrates the continued use of the "Mixed" setting 741 in relation to the "All researchers" category 740, thereby showing how particular data elements can be controlled through the user interface at increasingly granular levels for use in accordance with the ontology illustrated in FIG. 5. FIG. 7(*f*) shows the effect of clicking on "Mixed" setting 741 in the previous drawing. As shown, the file tree indicator 742 is now turned in a downward direction, thereby revealing granular details for such things as basic demographic information 743, symptoms data 744, diagnosis information 745, data regarding treatments 746, laboratory test results 747, genetic data 748, and psychiatric evaluation report 749. Each of these data elements is accompanied by the user's corresponding privacy preference selection setting, 750-756. Additionally, clicking on "Add more" link 757 enables the user to designate further data segments she wishes to establish, and the access controls therefor. Persons of ordinary skill in the art will recognize that by clicking on any of the data elements shown, the next more detailed file tree level can be revealed, for applying or reviewing the selected privacy preference selection, and will appreciate the manner in which this user interface can be used to review and/or edit selections made for specific genomic segments and/or metadata associated therewith, as described in relation to FIG. 2, and/or specific redactions as described in relation to FIG. 2 of Applicant's '554 patent.

FIGS. 7(*g*) and 7(*h*) illustrate use of the "Mixed" setting 716 to designate that variability exists along both axes of the improved user interface, contrasted with the one-dimensional variability previously described in connection with FIG. 7(*c*). As shown, arrow 758 indicates that variability exists along both the horizontal and vertical sliders. In one non-limiting example, clicking on this setting results in opening the 3-by-4 cell matrix shown in FIG. 7(*h*). As shown therein, the same principles that have been described in relation to extending the vertical axis preferably apply with respect to expanding the horizontal axis. While it is up to the system designer to select the best methods for such expression, in one preferred embodiment, similar to how sliding handle 705(*c*) downward reveals logical groups of successively more granular elements to the extent necessary to represent the user's preferences respecting which resource seekers, preferably as defined in connection shaded box 517 (of FIG. 5) may access particular data (or data elements) as defined in connection with shaded box 518 for what purposes of use 545, so too may sliding handle 704(*c*) to the right extend the types of data and accessibility types thereof in logical groups of successively more granular access types 548 and FIG. 7(*i*) hereof.

FIG. 7(*h*) provides one non-limiting example of such one preferred approach. As shown, clicking on "Mixed" setting 716 (or alternatively sliding handle 704(*a*) to the right) initially reveals three columns as the first logical sub-group from Total Access 706 of FIG. 7(*g*). These pertain to finding, using and exporting de-identified data, within the column entitled "Anonymous Data"759; finding, using and exporting identifying information, within the column entitled "Identifying Data" 760; and permitting use of contact information to make contact, within the third column entitled "Contact me"761. Persons of ordinary skill in the art will recognize by use of the term "de-identified data" that this pertains to complying with the standard for de-identifying data in accordance with HIPAA or the Common Rule, and while the term "anonymous" is not used in such U.S. statutes, it is employed herein simply to convey the essence of data that is devoid of such identifying information, and may be replaced with another caption that is more easily understood by system users should another title prove to be more useful at the literacy level of the intended users. Accordingly, for the purpose of this disclosure, "anonymous" refers to data that have been de-identified or anonymized in accordance with the law and/or other regulations applicable to the jurisdiction where the technology is deployed.

FIG. 7(*i*) provides a description of possible sub-classes for the foregoing three columnar categories. As illustrated by the class and sub-class tree indicating one optional semantic approach to defining such data type and accessibility type granularity spanning from the types with the lowest privacy-related implications to the greatest. As shown therein, these move from "Total Access" 706, to the three sub-categories 759-761 described in relation to FIG. 7(*h*). In one optional sub-group, "Anonymous Data" 759 may be broken into two sub-classes, "Find/Analyze" 762, in which such de-identified data may be indexed, analyzed and viewed; and "Use/Export" 763, wherein such de-identified data may be both used and exported. In turn, at the next most granular levels of data accessibility, deconstructing "Find/Analyze" 762 into three foundational components entails authorizing such anonymous information to be indexed 764; permitting such data to be analyzed within grouped data 765 (i.e., without ever having row level or and separately permitting the data to be viewed (for example in row level data extracts and/or in search results 766. Also as shown, at such next more granular level, deconstructing "Use/Export" 763 is comprised of permitting use of anonymous information, entitled "Use" 767; allowing so called "Limited Export" 768 focusing on only permitting the data to be exported to another Private Access-enabled system; and "Unlimited Export" 769 of such data to another system—even if it such systems do not employ Private Access.

FIG. 7(*i*) also provides a description of optional sub-classes for "Identifying Data" 760, which may be broken into two higher level sub-classes, "Find/Analyze" 770, in which such identifying information may be indexed, analyzed and viewed; and "Link/Use/Export" 771, wherein such identifying information may be both linked to the de-identified data 759, used and exported. In turn, at the next most granular levels of data accessibility, deconstructing "Find/Analyze" 770 can be into three foundational components. These entail authorizing such identifying information to be indexed 772; permitting such data to be analyzed within grouped data 773 (i.e., without ever having row level or and separately permitting the identifying data to be viewed); and allowing such information to be viewed 774, for example in row level data extracts and/or in search results.

Also as shown, the higher order category "Link/Use/Export" 771 may be deconstructed into five possible granular details. In one preferred embodiment, these include permitting the linking of the identifying information with de-identified data, entitled "Permitted Linking" 775; allowing so called "Limited Use" 776, which entails usage of the identifying information to conduct an activity but wherein no permission is granted to disclose such identifying information in the final results from such activity; "Limited Export" 777, wherein the data may be exported to another Private Access-enabled system; "Unrestricted Use" 778, wherein the identity may be revealed as part of the permitted use; and "Unrestricted Export" 779 of such identifying information to any system—even if it such systems do not employ Private Access.

Persons of ordinary skills in the art will appreciate that the foregoing semantic classes and sub-classes are arbitrary and employed principally for illustrative purposes only, and not to restrict or artificially limit the scope of the invention. As such, other semantic ontologies for purposes of use 547 and/or accessibility type 548, respectively described in relation to FIG. 5 hereof, may be employed in lieu of the foregoing in accordance with the principles hereof.

It should also be apparent that while each of the features illustrated in the accompanying drawings and the foregoing description are attractive and add to the usefulness of the invention, all of such foregoing features are not required in order to practice the principles of the invention and thus many are optional. Additionally, although the disclosure hereof has been made by way of examples and description of preferred embodiments, it will be evident that various adaptations and modifications may be employed without departing from the spirit and scope thereof.

A key issue in genome interpretation and ascertaining meaning for variants of unknown significance (VUS) is attaining better access to the subject's medical and family history, as well as associated environmental factors. At present, such correlations are impeded by significant "siloing"of information, which result from a number of factors. Some of these are regulatory in nature, arising from obligations imposed under law on data holders. Other impediments have to do with practical disincentives to sharing information, the control over which may produce a competitive advantage to the holder. Others arise from the heterogeneity of technologies and large variations in semantic representations employed across the industry, which are in turn promulgated to some degree by purpose of use, and in other cases by competition among hardware, software and data collection vendors. Nevertheless, in many cases, the difficulties arise from the growing recognition that with access to enough information—even fully de-identified data, and particularly longitudinal data—can become identifying in nature.

While for illustrative purposes, the foregoing system of segmenting and controlling the flow of sensitive information has been described principally in relation to genomic data, many of the disclosed features and principles will also be useful to enhancing the privacy and enabling broad sharing of other forms of bioinformatic data and other forms of sensitive data. For example, including survey data commonly held in registries, clinical observations and data based on interactions with providers commonly held in electronic health records (EHR) systems, and data acquired through active and passive monitoring through mobile devices and other systems designed to collect detailed data about the individual.

All of such instances and the like (including without limitation respecting personal educational information, financial data, e-government based information, and smart grid-based data) are expressly included in the foregoing disclosures; and persons of ordinary skill in the art will be able to extend the teachings of this disclosure to such further forms of sensitive data without undue experimentation or modification in the basic teachings. Moreover, by doing so, it will be apparent to persons of ordinary skill in the art that incorporating all of such information together with the individual's genomic data and comprehensive longitudinal health record under a common, inherently consumer-centric means of enabling greater accessibility and enhanced privacy protection that cuts across the silos in which such raw data is today represents extraordinary promise to realizing the optimal conditions for assuring and maintaining trust, accelerating the Precision Medicine Initiative, and the shared benefit capable of being derived from similar sorts of initiatives throughout the world.

The terms and expressions employed herein have been used as terms of description and not of limitation; and thus, there is no intent of excluding equivalents, but on the contrary it is intended to cover any and all equivalents that may be employed without departing from the spirit and scope of this disclosure.

What is claimed is:

1. A system for selectively designating segments of bioinformatics data of a genome in an electronic document comprising:
   (a) at least one computer configured to receive from a party wishing to designate segments of bioinformatics data, selected directives of a set of selectable access control directives, wherein said bioinformatics data is metadata concerning variants identified within the sub-bands of the chromosomes, and said designated segments are metadata indicating, for each of said chromosomal sub-bands, the name of the gene located within said single chromosomal sub-band wherein a variant is identified;
   (b) receive a command from the person to whom said bioinformatics data pertains or said person's designated representative designating said segments of said electronic document so as to identify at least one portion of said bioinformatics data to be subject to access control;
   (c) present a set of selectable access control directives defining conditions for access to said at least one portion of said metadata;
   (d) receive selected directives of said set of selectable access control directives; and
   (e) impose access control of said at least one portion of said metadata in accordance with said conditions in response to receiving said selective access control directives.

2. The system of claim 1, wherein said set of selectable access control directives defining conditions for access to said at least one portion of said bioinformatic data minimally consists of allow access to at least one portion of said bioinformatics data, prohibit access to said at least one portion of said bioinformatic data, and query the person to whom said bioinformatic data pertains (or that person's designated representative) for direction as to whether to allow or prohibit said proposed access.

3. The system of claim 1, wherein said at least one computer is further configured to present a privacy menu on a document viewing user interface.

4. The system of claim 3, wherein said at least one computer is further configured to receive mouse clicks on said privacy menu to identify selected directives.

5. The system of claim 1, wherein said bioinformatics data of a genome and said designated segments are the genes and SNPs suspected to be associated with a particular symptom, medical sign, or relevance to drug responsiveness.

6. The system of claim 5, wherein said bioinformatic data is metadata concerning variants identified within any of said genes or SNPs that are suspected to be associated with a particular symptom, medical sign, or relevance to drug responsiveness and said designated segments are the said metadata indicating for each of said symptom, medical sign, or relevance to drug responsiveness, the name of the genes and/or SNPs that are affected and the name of any variants located within said one or more genes or SNPs wherein at least one variant is identified.

7. The system of claim 5, wherein said bioinformatics data is meta-metadata concerning whether any variants are identified within any of the genes or SNPs that are suspected to be associated with a particular symptom, medical sign, or relevance to drug responsiveness, and said designated segments are the said meta-metadata indicating in a binary expression, for each one of said symptom, medical sign, or relevance to drug responsiveness, whether there is at least a gene or SNP where a variant is identified.

8. A system for selectively designating segments of bioinformatics data of a genome in an electronic document comprising:
   (a) at least one computer configured to receive from a party wishing to designate segments of bioinformatics data, selected directives of a set of selectable access control directives, wherein said bioinformatics data is meta-metadata concerning whether any variants are identified within sub-bands of the chromosomes, and said designated segments are meta-metadata indicating, in a binary expression for each said chromosomal sub-band, whether there is at least one gene within said single chromosomal sub-band wherein a variant is identified;
   (b) receive a command from the person to whom said bioinformatics data pertains or said person's designated representative designating said segments of said electronic document so as to identify at least one portion of said bioinformatics data to be subject to access contro;
   (c) present a set of selectable access control directives defining conditions for access to said at least one portion of said metadata;
   (d) receive selected directives of said set of selectable access control directives; and
   (e) impose access control of said at least one portion of said metadata in accordance with said conditions in response to receiving said selective access control directives.

9. A system for selectively designating segments of bioinformatics data of a genome or exome in an electronic document comprising:
   (a) at least one computer configured to receive from a party wishing to designate segments of bioinformatics data, selected directives of a set of selectable access control directives, wherein said bioinformatics data is meta-metadata concerning whether any variants are identified within said genes, and said designated segments are the said meta-metadata indicating, in a binary expression for each one of said genes, whether there is at least one variant identified;
   (b) receive a command from the person to whom said bioinformatics data pertains or said person's designated representative designating said segments of said electronic document so as to identify at least one portion of said bioinformatics data to be subject to access control;
   (c) present a set of selectable access control directives defining conditions for access to said at least one portion of said metadata;
   (d) receive selected directives of said set of selectable access control directives; and
   (e) impose access control of said at least one portion of said metadata in accordance with said conditions in response to receiving said selective access control directives.

10. A system for selectively designating segments of bioinformatics data of a genome or exome in an electronic document comprising:
   (a) at least one computer configured to receive from a party wishing to designate segments of bioinformatics data, selected directives of a set of selectable access control directives, wherein said bioinformatics data is meta-metadata concerning whether any variants are identified within said base pairs, and said designated segments are meta-metadata indicating, in a binary expression for each one of said SNPs, whether there is at least one variant identified;

(b) receive a command from the person to whom said bioinformatics data pertains or said person's designated representative designating said segments of said electronic document so as to identify at least one portion of said bioinformatics data to be subject to access control;

(c) present a set of selectable access control directives defining conditions for access to said at least one portion of said metadata;

(d) receive selected directives of said set of selectable access control directives; and (e) impose access control of said at least one portion of said metadata in accordance with said conditions in response to receiving said selective access control directives.

11. A system for selectively designating segments of bioinformatics data of a genome or exome in an electronic document comprising:

(a) at least one computer configured to receive from a party wishing to designate segments of bioinformatics data, selected directives of a set of selectable access control directives, wherein said bioinformatics data is meta-metadata concerning whether any variants are identified within any of the genes or SNPs that are suspected to be associated with a particular medical diagnosis, condition or disorder, and said designated segments are the said meta-metadata indicating in a binary expression for each one of said diagnosis, condition or disorder, whether there is at least one gene or SNP where a variant is identified;

(b) receive a command from the person to whom said bioinformatics data pertains or said person's designated representative designating said segments of said electronic document so as to identify at least one portion of said bioinformatics data to be subject to access control;

(c) present a set of selectable access control directives defining conditions for access to said at least one portion of said metadata;

(d) receive selected directives of said set of selectable access control directives; and (e) impose access control of said at least one portion of said metadata in accordance with said conditions in response to receiving said selective access control directives.

* * * * *